US005756343A

United States Patent [19]
Wu et al.

[11] Patent Number: 5,756,343
[45] Date of Patent: May 26, 1998

[54] CELL STRESS TRANSCRIPTIONAL FACTORS

[75] Inventors: Carl Wu; Joachim Clos, both of Bethesda; J. Timothy Westwood, Rockville; Sridhar Rabindran, Silver Spring, all of Md.

[73] Assignee: The United States of America as represented by the Department of Health and Human Services, Washington, D.C.

[21] Appl. No.: 178,477

[22] Filed: Jan. 7, 1994

Related U.S. Application Data

[62] Division of Ser. No. 617,910, Nov. 26, 1990, abandoned.

[51] Int. Cl.[6] .............................. C12N 1/21; C12N 15/12; C12N 15/63

[52] U.S. Cl. .................... 435/252.3; 536/23.1; 536/23.5; 435/320.1; 435/172.3; 435/252.33; 435/254.11; 435/325; 435/363; 935/9; 935/10; 935/29; 935/72; 935/69; 935/70

[58] Field of Search ................................ 536/23.1, 23.5; 435/91.1, 91.2, 91.4, 172.3, 252.33, 252.3, 245.12, 320.1, 325, 348, 349, 350, 351, 352, 353, 354, 365, 366, 254.11

[56] References Cited

U.S. PATENT DOCUMENTS

5,137,805  8/1992  Kingston et al. .......................... 435/6

OTHER PUBLICATIONS

Abdella, P.M.; Smith, P.K.; and Royer, G.P. "A New Cleavable Reagent for Cross-linking and Reversible Immobilization of Proteins." Biochem. Biophys. Research Communications 87 (3): 734–742, 1979.

Burnett, W.N. "Western Blotting": Electrophoretic Transfer of Proteins from Sodium Dodicyl Sulfate–Poly Acrylamide Gels to Unmodified Nitrocellulose and Radiographic Detection with Antibody and Radioiodinated Protein A. Analytical Biochemistry 112:195–203, 1981.

Kingston, R.E.; Schuetz, T.J.; and Larin, Z. "Heat–Induceble Human Factor that Binds to a Human Hsp70 Promoter." Mol. Cell. Biol. 7(4): 1530–1534, 1987.

Larson, J.S.; Schuetz, T.J.; and Kingston, R.E. "Activation in vitro of Sequence–Specific DNA Binding by a Human Regulatory Factor", Nature 335: 372–375, 1988.

Perisic, O.; Xiao, H.; and Lis, J.T. "Stable Binding of Drosophila Heat Shock Factor to Head–to–Head and Tail–to–Tail Repeats of a Conserved 5 bp Recognition Unit." Cell 59:797–806, 1989.

Schuetz, T.J.; Gallo, G.J.; Sheldon, L.; and Tempst, P. "Isolation of a cDNA for HSF2: Evidence for Two Heat Shock Factors in Humans," Proc. Natl. Acad. Sci. USA 88: 6911–6915, 1991.

Sorger, P.K. and Nelson, H.C.M. "Trimerization of a Yeast Transcriptional Activator via a Coiled–Coil Motif." Cell 59: 807–813, 1989.

Andersson, L.O.; Borg, H.; and Mikaelsson, M. "Molecular Weight Estimations of Protein by Electrophoresis in Polyacrylamide Gels of Graded Porosity." FEBS Letters 20(2): 199–201, 1972.

Watson et al. 1987, in: Molecular Biology Of The Gene, Fourth Edtion, Benjamin/Cummings Publ. co., Menlo Park, CA p. 313.

*Primary Examiner*—Christopher S. F. Low
*Attorney, Agent, or Firm*—Morgan & Finnegan, L.L.P.

[57] ABSTRACT

The present invention relates to DNA sequence coding for part or all of the heat shock transcription factor or heat shock factor (HSF) proteins derived from humans and Drosophila, and the proteins encoded by these sequences.

The present invention also includes methods for detecting HSF in a biological sample. The presence of HSF in the nucleus of a cell can be detected with specific anti-HSF antibody reagents. The presence of such HSF proteins in the nucleus indicates a stressed condition including diseases. Furthermore, the presence of multimeric HSF in the crude or fractionated cell extract is indicative of a stressed state.

15 Claims, 28 Drawing Sheets

FIG. 1A

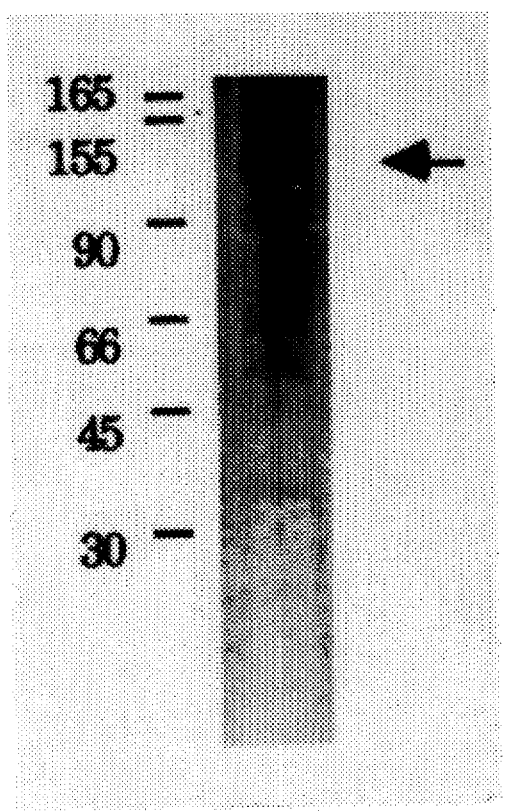

FIG. 1B peptide 16:   Ala-Val-Gln-Phe-Lys peptide 23:   Asp-Gly-Gln-Ser/Met-Phe-Val-Ile-Gln-Asn-Ala-
              Gln-Phe-Ala peptide 27:   Lys-Val-Gln-Leu-Met-Ile-Asn-Asn-Thr-Pro-Glu-
              $\begin{array}{c}\phantom{TT}\;C\phantom{CA}\;C\phantom{GT}\;C\phantom{GA}\;G\phantom{TAC}\phantom{TA}\;G\\3'TT\;CA\;GT\;GA\;TAC\;TA\;TT-5'\\\phantom{TT}\;T\phantom{CA}\;G\phantom{GT}\;T\phantom{GA}\;C\phantom{TAC}\phantom{TA}\;A\end{array}$   oligo 27
              Ile-Asp-Arg peptide 29:   Phe-Ser-Ala-Met-Lys-Gln-Glu-Asn-Gly-Val-Leu
              oligo 27 $\begin{array}{c}\phantom{TAC}\;C\phantom{TT}\;C\phantom{GT}\;C\phantom{CT}\;G\phantom{TT}\;C\\3'-TAC\;TT\;GT\;CT\;TT\;CT\;CA-5'\\\phantom{TAC}\;T\phantom{TT}\;T\phantom{GT}\;T\phantom{CT}\;A\phantom{TT}\;T\end{array}$ peptide 32:   Phe-Ala-X -Asn-Phe-Asp-Val-Pro-Thr-Asn-Ser-
              X -Leu-Leu-Asp-Ala-Asn-Gln-Ala peptide 39:   Ile-Thr-Ser-Ile-Asp-Asn-Gly-Gly

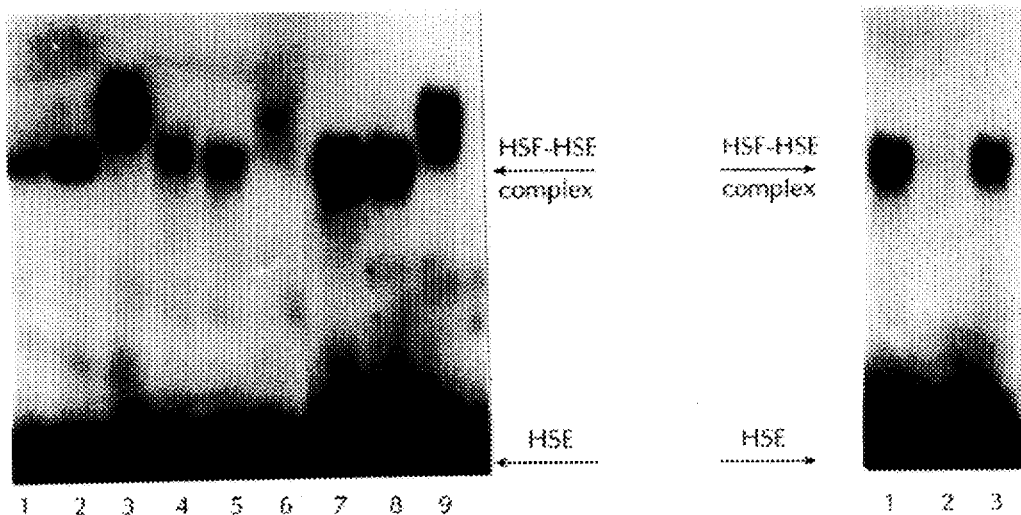

HOMOLOGY REGION A

```
DROSOPHILA  45   GVPAFLAKLW RLVDDADTNR LICWTKDGQS FVIQNQAQFA KELLPLNYKH  94
YEAST      171   SRPAFVNKLW SMLNDDSNTK LIQWAEDGKS FIVTNREEFV HQILPKYFKH 220

95   NNMASFIRQL NMYGFHKITS IDNGGLRFDR DEI.EFSHPF FKRNSPFLLD 143
           221   SNFASFVRQL NMYGWHKVQD VKSGSIQSSS DDKWQFENEN FIRGREDLLE 270

144   QIKR.KISNN KNGDDKGLVK PEAMSKI... .......... ..........  169
           271   KIIRQKGSSN NHNSPSGNGN PANGSNIPLD NAAGSNNSNN NISSSNSFFN 320
```

HOMOLOGY REGION B

```
DROSOPHILA 170   ...LTDVKVM R.......GR QDNLDSRFSA MKQ....... ..........  192
YEAST      321   HGHLLQGKTL RLMNEANLGD KNDVTAILGE LEQIKYNQLA ISKDLLRINK 370

193   ENEVLWREIA SLRQKHAKQQ QIVNKLIQFL ITIV...QPS RNMSGV     235
           371   DNELLWQENM MARERHRTQQ QALEKMFRFL TSIVPHLDPKMIMDGL         416
```

HOMOLOGY REGION C

```
DROSOPHILA 273   EELLDEVMNP SPAGYTAASH YDQESVSPPA VERPRSNMSI SSH        315
YEAST      673   NSNMESAVNV NSPGFNLQDY LTGESNSPNS VHSVPSNGSG STP        715
```

HOMOLOGY REGION D

```
DROSOPHILA 456   EPENSSGLMD LMTPANDLYS VNFISEDMPT DIFEDALLPD GVEEAAKLDQ 505
YEAST      733   QGENGSGLTP FLTVDDHTLN DNNTSEG.ST RVSPDIKFSA S..ENTKVSD 779
```

```
DROS.HSF    87  ILPLNYKHNNMASFIRQLNMYGFHKITSIDNGGL  120
YEAST HSF  213  ILPKYFKHSNFASFVRQLNMYGWHKVQDVKSGSI  236

SIGMA 32   253  LQEILADRYGVSAERVRQLEKNAMKKLRAAIEA   284
SIGMA 70   573  LEEMGKQFDVTRERIRQIEAKALRKLRHPSRSEV  606
```

FIG. 9B

```
            abcdefgabcdefgabcdefgabcdefgabcd    cdefgabcdefgabcdefga    gabcdefgabc
DROS.HSF   ◆                    ◆         ◆    ◆              ◇ ◆                ◇
166-MSKILTDVKVMRGRQDNLDSRFSAMKQENEVLWREIASLRQKHAKQQQIVNKLIQFLITIVQPSRNMSGVKRHVQLM-242
     ◇       ◇       ◇      ◇              ◇         ◇       ◇     ◇
344-VTAILGELEQIKYNQLAISKDLLRINKDNELLWQENMMARERHRTQQQALEKMFRFLTSIVPHLDPKMIMDGLGDPK-420
YEAST HSF
```

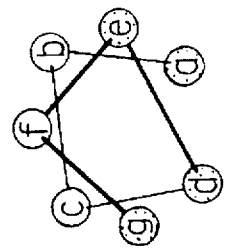

FIG. 9D

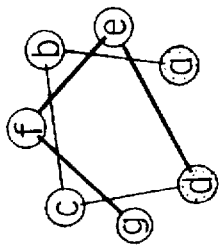

FIG. 9C

```
-159 CGGGCCCGTTGCAAGATGGCGGCGGCCATGCTGGGCCCCGGGGCTGTGTGTGCGCAGCGG -100
 -99 GCGGCGGCGCGGCCCGGAAGGCTGGCGCGGCGACGGCGTTAGCCCGGCCCTCGGCCCCTC  -40
                                              M  D  L  P  V  G  P    7
  -39 TTTGCGGCCGCTCCCTCCGCCTATTCCCTCCTTGCTCGAGATGGATCTGCCCGTGGGCCC   20
       G  A  A  G  P  S  N  V  P  A  F  L  T  K  L  W  T  L  V  S   27
   21 CGGCGCGGCGGGGCCCAGCAACGTCCCGGCCTTCCTGACCAAGCTGTGGACCCTCGTGAG   80
       D  P  D  T  D  A  L  I  C  W  S  P  S  G  N  S  F  H  V  F   47
   81 CGACCCGGACACCGACGCGCTCATCTGCTGGAGCCCGAGCGGGAACAGCTTCCACGTGTT  140
       D  Q  G  Q  F  A  K  E  V  L  P  K  Y  F  K  H  N  N  M  A   67
  141 CGACCAGGGCCAGTTTGCCAAGGAGGTGCTGCCCAAGTACTTCAAGCACAACAACATGGC  200
       S  F  V  R  Q  L  N  M  Y  G  F  R  K  V  V  H  I  E  Q  G   87
  201 CAGCTTCGTGCGGCAGCTCAACATGTATGGCTTCCGGAAAGTGGTCCACATCGAGCAGGG  260
       G  L  V  K  P  E  R  D  D  T  E  F  Q  H  P  C  F  L  R  G  107
  261 CGGCCTGGTCAAGCCAGAGAGAGACGACACGGAGTTCCAGCACCCATGCTTCCTGCGTGG  320
       Q  E  Q  L  L  E  N  I  K  R  K  V  T  S  V  S  T  L  K  S  127
  321 CCAGGAGCAGCTCCTTGAGAACATCAAGAGGAAAGTGACCAGTGTGTCCACCCTGAAGAG  380
       E  D  I  K  I  R  Q  D  S  V  T  K  L  L  T  D  V  Q  L  H  147
  381 TGAAGACATAAAGATCCGCCAGGACAGCGTCACCAAGCTGCTGACGGACGTGCAGCTGAT  440
       K  G  K  Q  E  C  M  D  S  K  L  L  A  M  K  H  E  N  E  A  167
  441 GAAGGGGAAGCAGGAGTGCATGGACTCCAAGCTCCTGGCCATGAAGCATGAGAATGAGGC  500
       L  W  R  E  V  A  S  L  R  Q  K  H  A  Q  Q  K  V  V  N  187
  501 TCTGTGGCGGGAGGTGGCCAGCCTTCGGCAGAAGCATGCCCAGCAACAGAAAGTCGTCAA  560
       K  L  I  Q  F  L  I  S  L  V  Q  S  N  R  I  L  G  V  K  R  207
  561 CAAGCTCATTCAGTTCCTGATCTCACTGGTGCAGTCAAACCGGATCCTGGGGGTGAAGAG  620
       K  I  P  L  M  L  N  D  S  G  S  A  H  S  M  P  K  Y  S  R  227
  621 AAAGATCCCCCTGATGCTGAACGACAGTGGCTCAGCACATTCCATGCCCAAGTATAGCCG  680
       Q  F  S  L  E  H  V  H  G  S  G  P  Y  S  A  P  S  P  A  Y  247
  681 GCAGTTCTCCCTGGAGCACGTCCACGGCTCGGGCCCCTACTCGGCCCCCTCCCCAGCCTA  740
       S  S  S  S  L  Y  A  P  D  A  V  A  S  S  G  P  I  I  S  D  267
  741 CAGCAGCTCCAGCCTCTACGCCCCTGATGCTGTGGCCAGCTCTGGACCCATCATCTCCGA  800
       I  T  E  L  A  P  A  S  P  M  A  S  P  G  G  S  I  D  E  R  287
  801 CATCACCGAGCTGGCTCCTGCCAGCCCCATGGCCTCCCCCGGCGGGAGCATAGACGAGAG  860
       P  L  S  S  S  P  L  V  R  V  K  E  E  P  P  S  P  P  Q  S  307
  861 GCCCCTATCCAGCAGCCCCCTGGTGCGTGTCAAGGAGGAGCCCCCCAGCCCGCCTCAGAG  920
```

FIG. 13A

```
308  P   R   V   E   E   A   S   P   G   R   P   S   S   V   D   T   L   L   S   P   327
921  CCCCCGGGTAGAGGAGGCGAGTCCCGGGCGCCCATCTTCCGTGGACACCCTCTTGTCCCC  980

328  T   A   L   I   D   S   I   L   R   E   S   E   P   A   P   A   S   V   T   A   347
981  GACCGCCCTCATTGACTCCATCCTGCGGGAGAGTGAACCTGCCCCCGCCTCCGTCACAGC 1040

348  L   T   D   A   R   G   H   T   D   T   E   G   R   P   P   S   P   P   P   T   367
1041 CCTCACGGACGCCAGGGGCCACACGGACACCGAGGGCCGGCCTCCCTCCCCCCGCCCAC  1100

368  S   T   P   E   K   C   L   S   V   A   C   L   D   K   N   E   L   S   D   H   387
1101 CTCCACCCCTGAAAAGTGCCTCAGCGTAGCCTGCCTGGACAAGAATGAGCTCAGTGACCA 1160

388  L   D   A   M   D   S   N   L   D   N   L   Q   T   M   L   S   S   H   G   F   407
1161 CTTGGATGCTATGGACTCCAACCTGGATAACCTGCAGACCATGCTGAGCAGCCACGGCTT 1220

408  S   V   D   T   S   A   L   L   D   L   F   S   P   S   V   T   V   P   D   M   427
1221 CAGCGTGGACACCAGTGCCCTGCTGGACCTGTTCAGCCCCTCGGTGACCGTGCCCGACAT 1280

428  S   L   P   D   L   D   S   S   L   A   S   I   Q   E   L   L   S   P   Q   E   447
1281 GAGCCTGCCTGACCTTGACAGCAGCCTGGCCAGTATCCAAGAGCTCCTGTCTCCCCAGGA 1340

448  P   P   R   P   P   E   A   E   N   S   S   P   D   S   G   K   Q   L   V   H   467
1341 GCCCCCCAGGCCTCCCGAGGCAGAGAACAGCAGCCCGGATTCAGGGAAGCAGCTGGTGCA 1400

468  Y   T   A   Q   P   L   F   L   L   D   P   G   S   V   D   T   G   S   N   D   487
1401 CTACACAGCGCAGCCGCTGTTCCTGCTGGACCCCGGCTCCGTGGACACCGGGAGCAACGA 1460

488  L   P   V   L   F   E   L   G   E   G   S   Y   F   S   E   G   D   G   F   A   507
1461 CCTGCCGGTGCTGTTTGAGCTGGGAGAGGGCTCCTACTTCTCCGAAGGGGACGGCTTCGC 1520

508  E   D   P   T   I   S   L   L   T   G   S   E   P   P   K   A   K   D   P   T   527
1521 CGAGGACCCCACCATCTCCCTGCTGACAGGCTCGGAGCCTCCCAAAGCCAAGGACCCCAC 1580

547
528  V   S   *
1581 TGTCTCCTAGAGGCCCCGGAGGAGCTGGGCCAGCCGCCCACCCCCACCCCCAGTGCAGGG 1640

1641 CTGGTCTTGGGGAGGCAGGGCAGCCTCGCGGTCTTGGGCACTGGTGGGTCGGCCGCCATA 1700
1701 GCCCCAGTAGGACAAACGGGCTCGGGTCTGGGCAGCACCTCTGGTCAGGAGGGTCACCCT 1760
1761 GGCCTGCCAGTCTGCCTTCCCCCAACCCCGTGTCCTGTGGTTTGGTTGGGGCTTCACAGC 1820
1821 CACACCTGGACTGACCCTGCAGGTTGTTCATAGTCAGAATTGTATTTTGGATTTTTACAC 1880
1881 AACTGTCCCGTTCCCCGCTCCACAGAGATACACAGATATATACACACAGTGGATGGACGG 1940
1941 ACAAGACAGGCAGAGATCTATAAACAGACAGGCTCTAAAAAAAAAAAAAAAAAAAA     1996
```

FIG. 13B

CELL STRESS TRANSCRIPTIONAL FACTORS

This is a divisional of application Ser. No. 07/617,910, filed on Nov. 26, 1990, now abandoned.

BACKGROUND OF THE INVENTION

1. Field of the Invention

The present invention relates to novel heat shock transcriptional activators or heat shock factors (HSF) and to polynucleotides encoding such factors. The present invention pertains in particular to Drosophila and human heat shock factors, polynucleotides encoding the same, and antibodies made to natural and recombinant HSFs.

2. Background Information

All organisms respond to elevated environmental temperatures and a variety of environmental stresses by rapidly activating the expression of a group of proteins referred to as heat shock or stress proteins. Although the functions of heat shock proteins have remained obscure for many years since the discovery of the phenomenon by Ritossa (1962), *Experientia*, 18, 571-573, recent studies suggest a central role for heat shock-induced proteins and their constitutive counterparts in mediating protein-protein interactions, protein folding and the transport of proteins across membranes (reviewed by Morimoto et al, 1990, Stress proteins in biology and medicine. Cold Spring Harbor Laboratory Press. 1–36). The synthesis of heat shock proteins is subject to both transcription and post-transcriptional control in eukaryotic cells (reviewed by Craig, 1985, *Crit. Rev. Biochem.*, 18, 239–280; Lindquist, 1986, Ann. Rev. Biochem., 55, 1151–1191). Heat shock-inducible transcription is mediated by a positive control element, the heat shock element (HSE), defined as three repeats of a 5-nucleotide [_GAA__] module, arranged in alternating orientation (Pelham, 1982, *Cell*, 30, 517–528; Amin et al, 1988, *Mol Cell. Biol* 8, 3761–3769; Xiao and Lis, 1988, *Science*, 239, 1139–1142). Multiple copies of the HSE are found upstream of all eukaryotes heat shock genes.

A heat shock activator protein or heat shock transcription factor now generally termed heat shock factor (HSF), binds to HSEs and activates transcription of heat shock genes. (Wu, 1984a, *Nature*, 309, 229–234, 1984b; Parker and Topol, 1984, *Cell*, 36, 357–369; Topol et al, 1985, *Cell*, 42, 527–537). Although the sequence of the HSE has been highly conserved in evolution, HSF purified from yeast, Drosophila, and human cells differ in molecular size (150 kD, 110 kD and 83 kD, respectively; Sorger and Pelham, 1987, *EMBO J*, 6, 3035–3041; Wu et al, 1987, *Science*, 238, 1247–1253; Goldenberg et al, 1988 *J. Biol. Chem.* 263, 19734–19739). Yeast and higher eukaryotes also differ in the regulation of HSF activity. In yeast, HSF bound constitutively to the HSE apparently stimulates transcription when phosphorylated under heat shock conditions. In Drosophila and vertebrate cells, HSF is unable to bind to the HSE unless the cells are heat shocked (for a review, see Wu et al, 1990, In: Stress proteins in biology and medicine. Cold Spring Harbor Laboratory Press. 429–442). The heat-inducible binding of HSF appears to be a major regulatory step in the pathway to heat shock gene activation in higher eukaryotes.

The induction and reversal of HSF binding activity in vivo does not require new protein synthesis (Zimarino and Wu, 1987, *Nature*, 327, 727–730; Kingston et al, 1987, *Mol. Cell. Biol.*, 7, 1530–1534; Zamarino et al, 1990a). In addition, HSF extracted from nonshocked cell cytosol can be activated in vitro by heat (Larson et al, 1988, *Nature*, 335, 372–375), low pH (Mosser et al, 1990, *Proc. Natl. Acad. Sci U.S.A.*, 87, 3748–3752), and by interaction with antibodies raised to the active form of HSF (Zimarino et al, 1990b, *Science*, 249, 546–549). These results suggest that the pre-existent, inactive form of HSF present in the cell cytosol can assume the active conformation without an enzymatic modification of protein structure, translocate to cell nucleus and activate heat shock protein.

The present invention relates to the structure and function of novel human and Drosophila heat shock factor (HSF) proteins and the DNA sequences that encode these proteins. In particular, the present invention relates to Drosophila and human HSF proteins produced in *E. coli* and *Xenopus* oocytes and their specific DNA binding activities with and without heat shock induction.

BRIEF DESCRIPTION OF THE DRAWINGS

FIGS. 1A and B show the purification of Drosophila HSF and microsequencing of HSF peptides. (A) SDS gel electrophoresis and silver staining of a HSF preparation from Drosophila Schneider Line 2 cells. 5% of the purified HSF fraction was electrophoresed on a 10% polyacrylamide gel. (B) Amino acid sequences of six peptides obtained by tryptic digestion of purified HSF. (see SEQ ID NOS:8, 9, 10, 11, 12 and 13) Oligo 27 (SEQ ID NO:38) and oligo 29 (SEQ ID NO:39) are two degenerate sequences (boxed), deduced from the amino acids under which they are aligned. The sequences represent the coding strand. Valine, leucine, and isoleucine codons of oligo 27 were chosen in accordance with the codon bias of Drosophila. All other codons are fully degenerate.

FIGS. 2A, 2B-1, 2B-2, 2B-3, and 2C represent the cloning and sequence analysis of Drosophila HSF. (A) Schematic representation of seven HSF cDNA clones aligned with reference to the reconstructed full-length HSF cDNA clone. HSF 302, 307, and 312 were isolated from an oligo dT-primed cDNA library, and HSF 407, 409, 410, and 412 were isolated from a random-primed cDNA library. The open bar represents the 2073 nt HSF open reading frame. (B) Nucleotide sequence of the HSF cDNA and predicted amino acid sequence. (see SEQ ID NOS:42 and 2) The entire DNA sequence presented has been sequenced at least twice, from overlapping cDNA clones. Start and stop codons, and a polyadenylation signal are highlighted by reverse print. Two single restriction sites (StuI, and ApaI) that were used for generation of 3' deletion mutants are noted. Sequences in the open reading frame that match the sequences of the six HSF tryptic peptides listed in FIG. 1B are boxed. (C) In situ hybridization of digoxigenin-substituted HSF DNA (coding sequences) to Drosophila salivary gland polytene chromosomes. The cytologicalocus of hybridization (55A), is indicated by the arrow.

FIGS. 3A, 3B, 3C-1, 3C-2, and 3D show the DNA-binding activity of recombinant Drosophila HSF. (A) Gel mobility shift analysis of natural and recombinant HSF. Cytoplasmic extracts from unshocked SL-2 cells (lanes 1–3), and HSF translated in vitro at 25° C. or 30° C. (lanes 4–9) were subjected to in vitro heat shock for 10 min at 34° C. or kept at 0° C. Prior to gel shift analysis, samples in lanes 3, 6, and 9 were incubated at room temperature with a 1:60 dilution of polyclonal serum raised against the national HSF protein purified from Drosophila cells (Zimarinoet al., 1990 *Science* 249, 546–549). Identical translations of anti-sense HSF RNA showed no DNA binding activity. (B) Gel mobility shift assay of HSF translated in vitro at 30° C., in the absence of competitor DNA (lane 1), with a 40-fold excess of unlabeled HSE (lane 2) or a similar excess of synthetic DNA from the hsp70 gene, positions +40 to +80 (lane 3). (C) DNase I protection analysis. Recombinant HSF extracted from *E. coli* was incubated with 5' $^{32}$P-labeled hsp70 promoter DNA, digested with DNase I, and analyzed by electrophoresis on a 8% sequencing gel (left panel; non-coding strand)or 6% (right panel; coding strand) sequencing gel. Amounts of HSF used for each reaction are indicated. The total protein concentration in all samples was normalized by the addition of extracts of bacteria transformed with the expression vector alone. The lanes marked A,C,G,T are dideoxy-sequencing reactions. (D) Nucleotide sequence of the hsp70 promoter from position −185 to +10. (see SEQ ID NOS:3 and 41) The sequences in lower case are from the plasmid vector. Three upstream HSEs and the TATA sequence are boxes. The start site and direction of transcription are indicated. Brackets indicate sequences protected by the recombinant HSF. There is a clear DNase I footprint on both strands over the two proximal HSEs, and some protection on the coding strand also occurs on the third HSE (position −174 to −186), the non-coding strand of which was not analyzed.

FIGS. 8A and 8B show the sequence comparison of Drosophila and yeast HSF. (A) Dot matrix plot of conserved amino acids between Drosophila HSF (horizontal) and yeast HSF (vertical), using the UWGCG sequence analysis programs Compare (window/stringency 30/17) and Dotplot. (B) Amino acid alignment of conserved regions A–D, using the UWGCG sequence analysis program BestFit, with default parameters. (SEQ ID NOS: 4, 5, 6, 14, 15, 16, 17, 18, 19, 20, 21, 22, 23 and 24) Vertical lines indicate amino acid identities. (:)indicates similar amino acids, according to Dayhoff as normalized by Gribskov and Burgess (1986). Conserved regions A–D are shaded. There are sequence similarities that extend beyond the somewhat arbitrary boundaries imposed on each conserved region.

FIGS. 9A to 9D show the comparison of the DNA binding domains of Drosophila HSF, yeast HSF, $\sigma^{32}$ and $\sigma^{70}$, and the comparison of the hydrophobic amino acid heptad repeats in Drosophila HSF and yeast HSF. (A) Alignment of protein sequences conserved between Drosophila HSF, yeast HSF, $\sigma^{32}$, and $\sigma^{70}$. Similar residues are boxed. The first helix of the putative helix-turn-helix motif of $\sigma^{32}$ starts at L-253, the turn at G-261, and the second (recognition) helix at A-264, the three residues comprising the turn are boxed. The Drosophila HSF sequence shows 27% identity/46% similarity to the $\sigma^{32}$ sequence in the block of 26 amino acids. (see SEQ ID NOS:25, 26, 27 and 28) (B) Comparison of the heptad repeats of hydrophobic amino acids found in Drosophila and yeast HSF sequences. (see SEQ ID NOS:29 and 30) The two sequences are aligned without gaps using conserved region B as defined by the Bestfit sequence analysis program as the starting frame of alignment. The repeats are made up of hydrophobic residues at positions a (open diamonds) and d (filled diamonds), in the nomenclature for coiled-coils (a b c d e f g)$_n$. The small diamonds represent a third array of hydrophobic residues positioned out of register by one residue from the second array. Heptad repeats of the yeast HSF sequence are taken from Sorger and Nelson (1989). Backbone illustration of hypothetical packing of α-helices are shown with the positions of hydrophobic residues stippled.

FIGS. 13A–B show the sequence analysis of human HSF reconstructed from overlapping cDNA clones. The sequence of the human HSF clone is shown along with the amino acid sequence. (see SEQ ID NOS:31 and 32) The entire clone has been sequenced at least twice from two or more independent overlapping clones. Numbering of the nucleotide sequence is from A of the presumptive initiating AUG codon. The stop codon UAG is indicated by *. Note that a stop codon is not present upstream of the presumptive initiating AUG, so that those sequences, and the amino acids they encode including sequencing farther upstream not yet identified, may be part of the natural HSF protein.

Control extracts (lane 1) and extracts from cells expressing human HSF (lane 2) were analyzed by electrophoresis on SDS-polyacrylamide gels and stained with Coomassie Blue R250. The arrow indicates recombinant human HSF. Molecular weight markers indicated on the left are: phosphorylase b (94,000), bovine serum albumin (67,000), and ovalbumin (43,000).

Figure 15A:
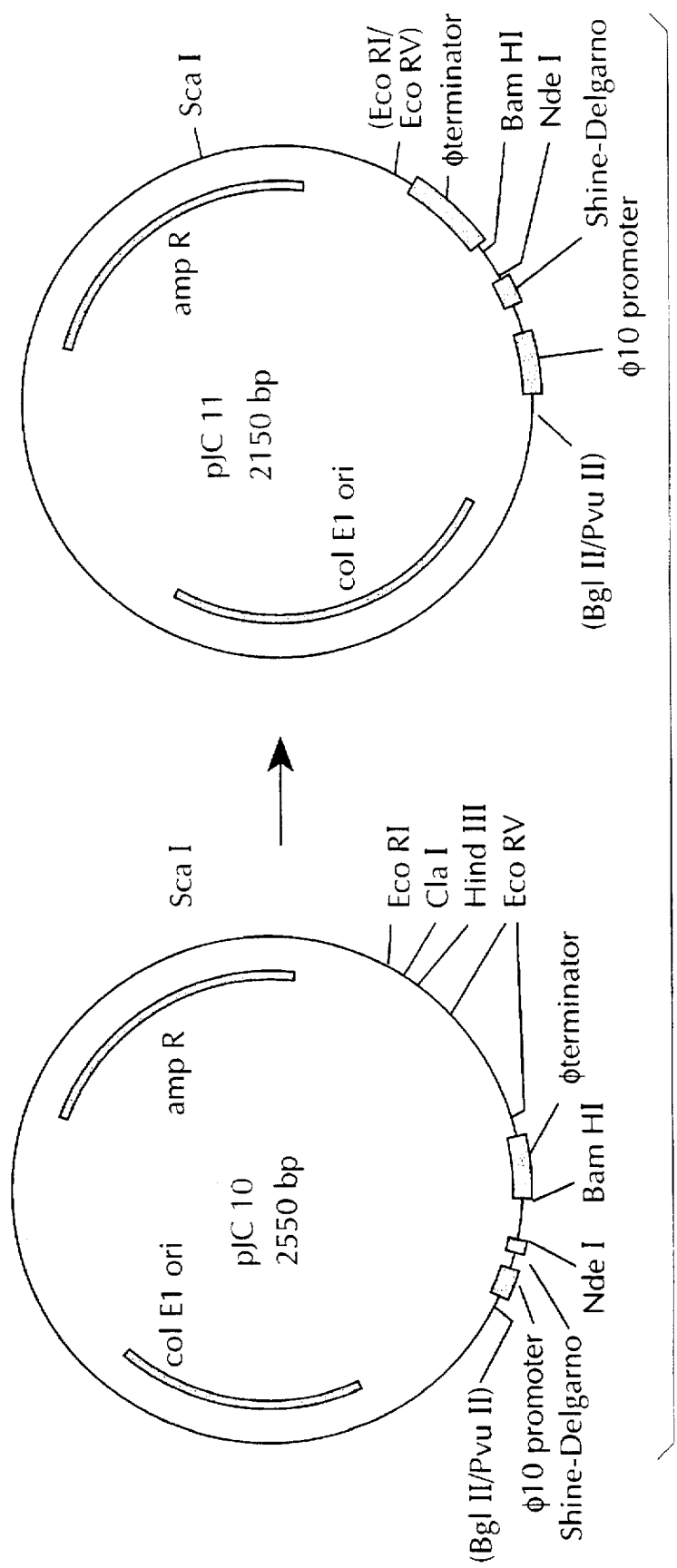
Figures 1, 15B:
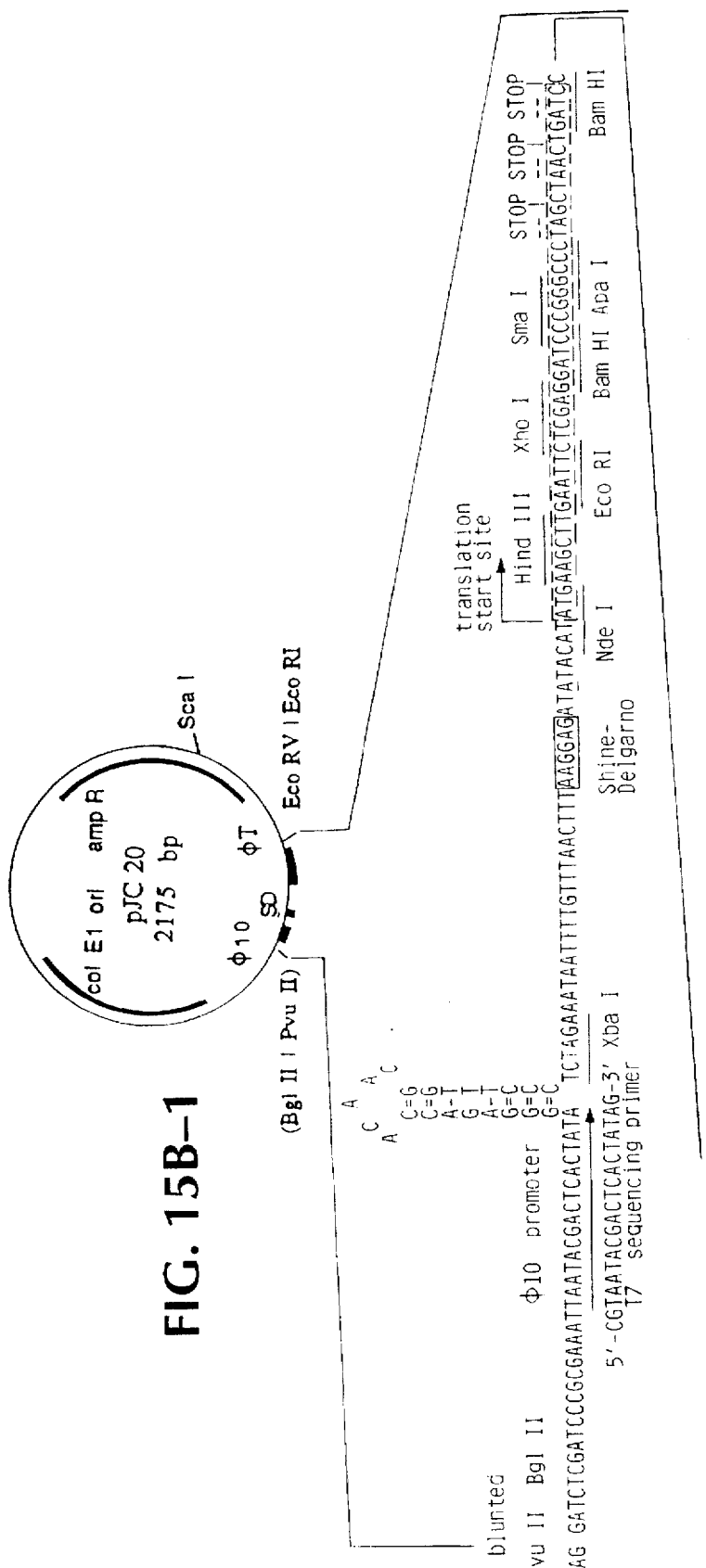

FIG. 15(A) shows the construction of vector pJC10 and pJC11. pJC10 (Clos et al., 1990, Cell 63) was cleaved with Eco RI and Eco RV. The recessive ends were filled in with Klenow enzyme and relegated. The resulting vector, pLC 11, does not contain the sites for Eco RI, Eco RV, Hind III, Cla I, and Nhe I downstream of the terminator. FIG. 15(B) shows the construction of the vector pJC20. pJC 11 was cleaved with Nde I and Ban HI and a synthetic oligonucleotide (shaded) was inserted which contains the new multiple cloning site and stop codons in all three reading frames. pJC20 is the vector used for the expression of huHSF open reading frame. (see SEQ ID NOS:33, 34, 35 and 36)

Figure 16:
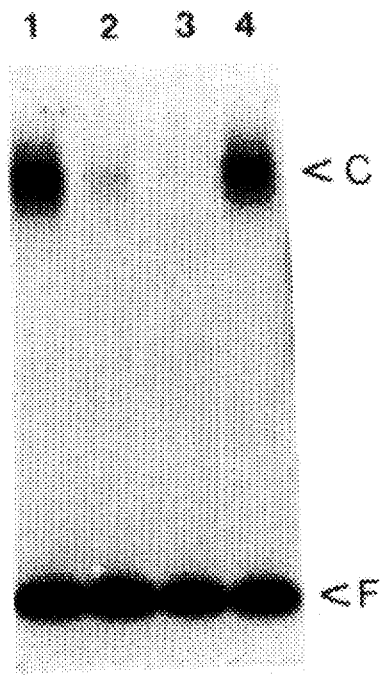

FIG. 16 shows gel mobility shift assay with recombinant HuHSF. Extracts prepared from bacterial cells expressing HuHSF were incubated with 10 fmoles $^{32}$P labelled oligonucleotide containing a synthetic HSE. The reaction mix contained in 10 μl: 10 mM Tris, pH 8, 1 mM EDTA, 1 μg E. coli DNA, 1 μg pdN5, 10 μg tRNA. After incubation at room temperature for 10 minutes, the reaction was loaded onto a 1% agarose-0.5× TBE gel, blotted onto DEAE paper, and autoradiographed. The positions of free DNA (F) and the protein-DNA complex (C) are indicated on the figure. Reactions were carried out in the absence of unlabelled competitor DNA (lane 1), in the presence of 50 fold excess of two different oligonucleotides containing HSEs (lanes 2,3) or with a similar amount of an unrelated oligonucleotide (lane 4). Control extracts prepared in parallel from cells not expressing HuHSF did not produce a mobility shift.

Figures 1, 17A:
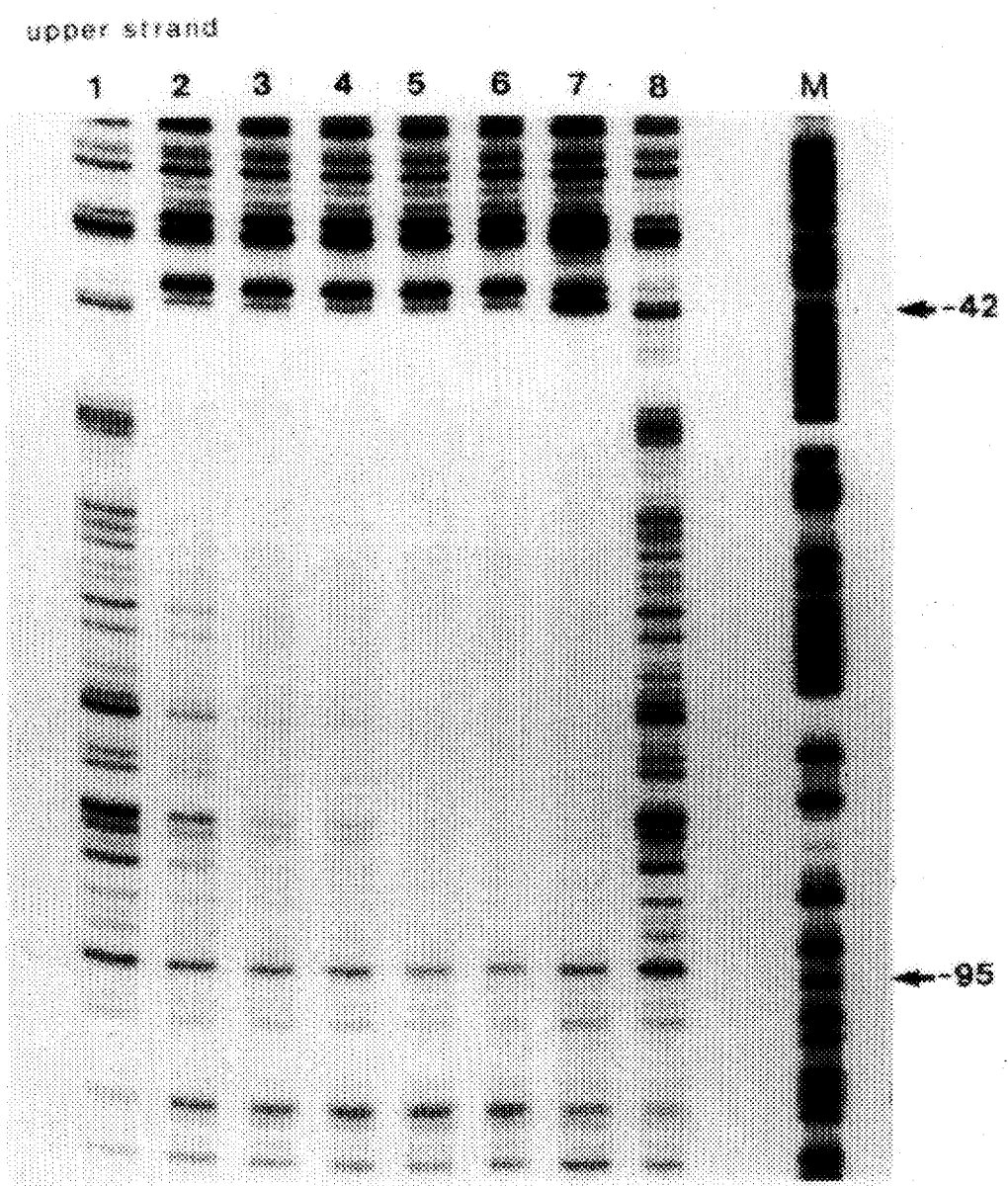
Figures 1, 17B:
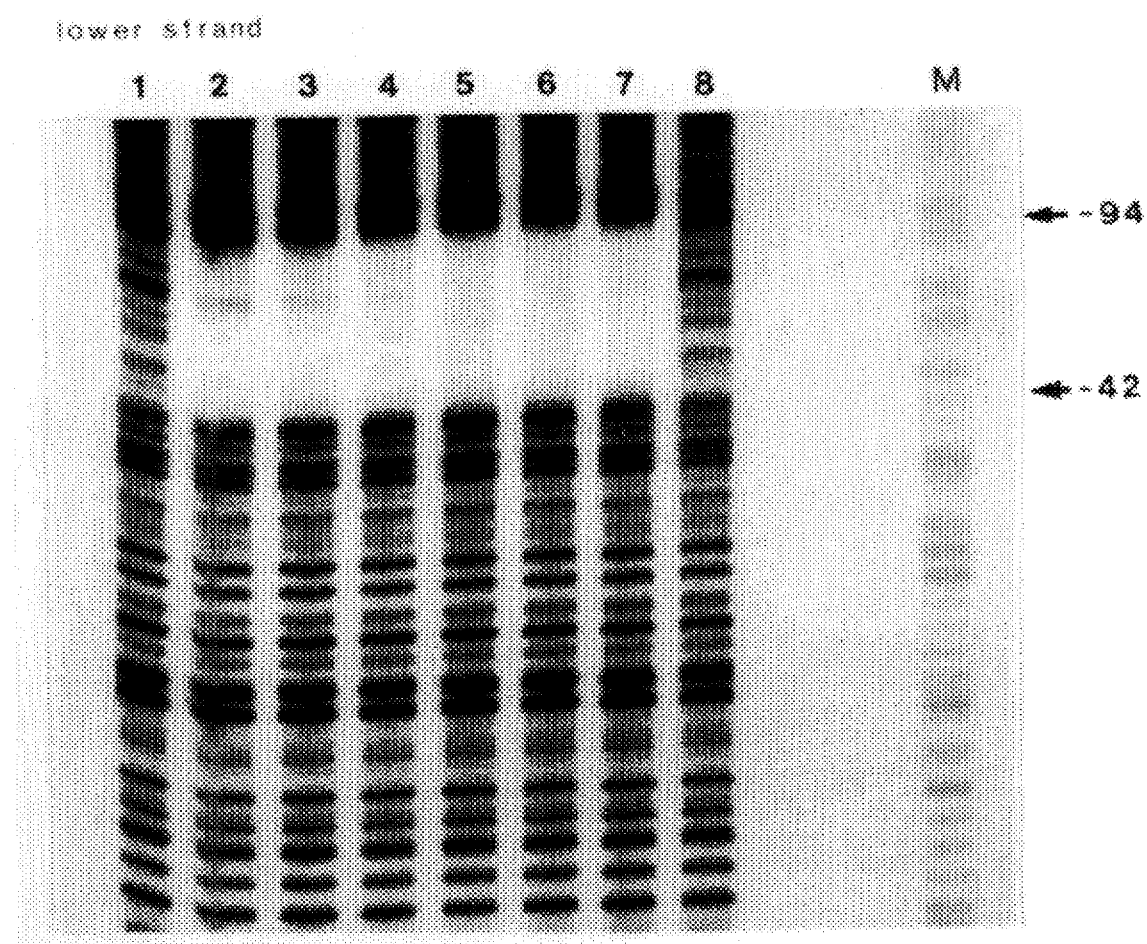
Figures 2, 17A, 17B:
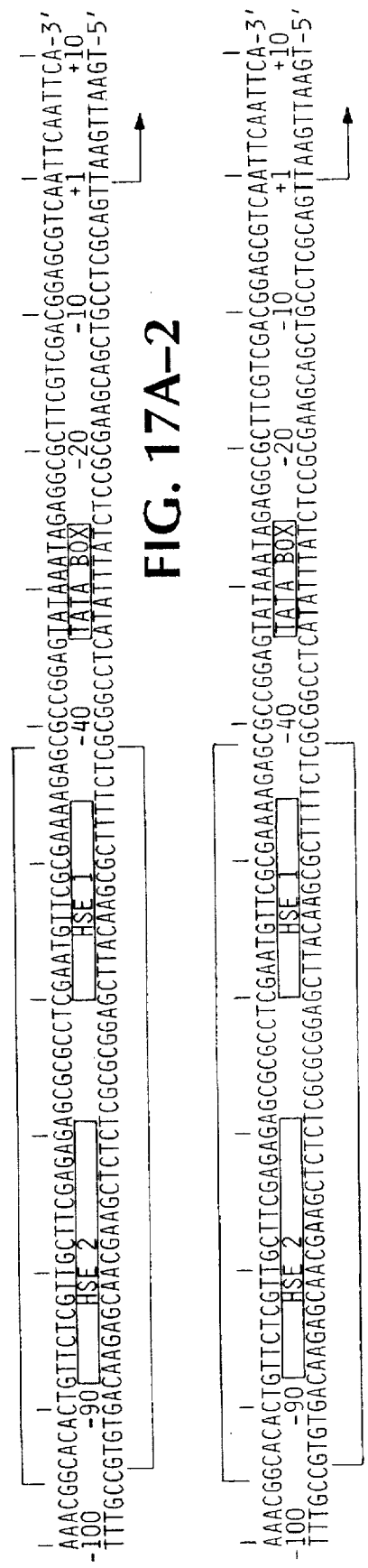

FIG. 17 shows the DNase I protection analysis of recombinant HuHSF. A DNA fragment of the hsp70 gene from position −185 (XhoI) to +295 (AccI) cloned into a Bluescript vector was labelled at either the XhoI site (upper strand) or at the HindIII site (lower strand). Extracts from E. coli cells expressing HUHSF or control cultures were incubated with 5 fmoles of labelled DNA fragments under the same conditions as those used for the mobility shift assay except that the reaction volume was 20 μl. After a 10 minute incubation at room temperature, 1 μl of 100 mM MgCl$_2$ and 0.03 units of DNaseI was added and incubation continued for 1 minutes. The reactions were terminated by addition of 2% SDS-50 mM EDTA; samples were purified by phenol-chloroform, extraction and ethanol precipitation and analyzed on a 8% polyacrylamide-6M urea sequencing gel.

Protection of the DNA fragment on the upper strand is shown in panel a; protection on the lower strand is shown in panel b. Lane 1: Free DNA control, lanes 2 to 6: footprints produced by 0.01, 0.013, 0.02, 0.04, 0.1 μl of extract from cells expressing HuHSF; lane 7: footprint produced by Drosophila HSF; lane 8: 0.1 μl of the control extract. M: sequencing ladder of the appropriate DNA fragment.

Below each panel is shown the nucleotide sequence of the hsp70 promoter from −100 to +10 with TATA box and the two heat shock elements boxed. (see SEQ ID NO:37) The extent of the footprints on each strand is indicated by the bracket. The footprints produced by the human and Drosophila proteins are essentially identical.

Figure 18:
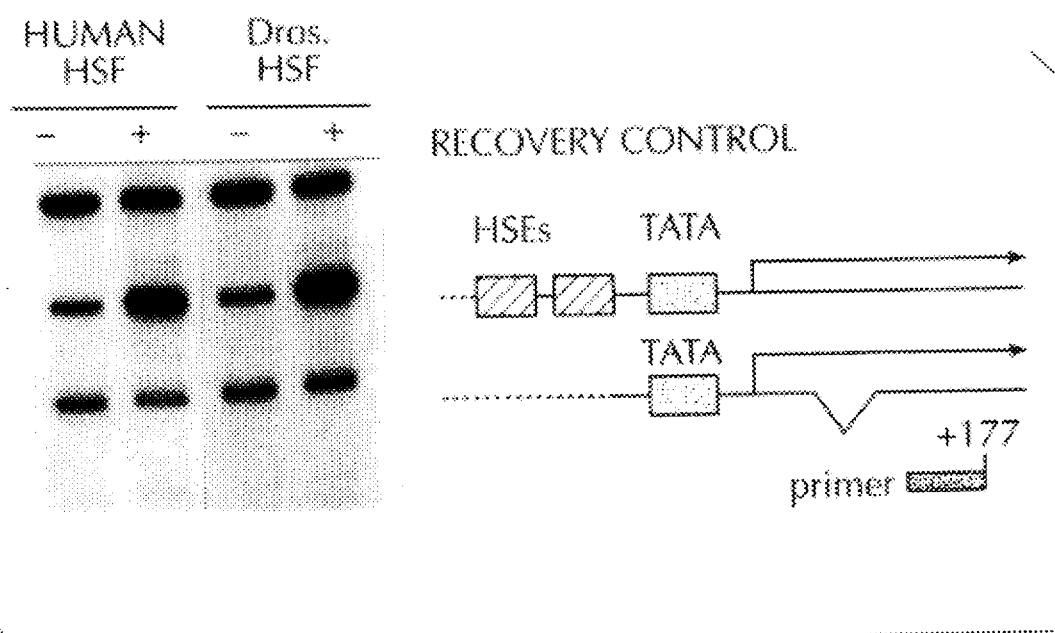

FIG. 18 demonstrates the transcriptional stimulation by recombinant human HUHSF in vitro. Primer extension analysis of RNA synthesized by nonshocked Drosophila embryo transcription extracts supplemented with 0.1 μl of E. coli extract from HUHSF expressing cells (+), or with extract from cells transformed with the expression vector only (−). For comparison, a similar experiment was performed with extracts of E. coli expressing the Drosophila HSF (Dros. HSF) protein. As an internal control for transcription from the template carrying two HSEs, the same template deleted of the HSEs (as well as a 30 bp downstream region) was mixed in the reaction. RNA originating from the template lacking HSEs is thus distinguished by a 30 nt decrease in size. As a further control for RNA recovery, a defined amount of RNA synthesized from a T$_7$ promoter upstream of the hsp70 sequences inserted into pBluescript was introduced into each transcription reaction along with the stop solution. Schematic drawings of the two templates are aligned with the primer extension products of the respective transcripts.

SUMMARY OF THE INVENTION

It is a general object of the present invention to provide segments of DNA molecules which codes for heat shock factor (HSF) proteins derived from Drosophila and human and their encoded proteins.

It is another object of the present invention to provide diagnostic methods for monitoring cells under abnormal stress conditions, including disease, by measuring the accumulation of HSF in the nucleus of stressed cell, or by measuring the multimeric state of HSF.

In one embodiment, the present invention relates to a DNA segment encoding all, or a unique portion, of either Drosophila or human HSF protein.

In another embodiment, the present invention relates to a recombinantly produced protein encoded by all, or a unique portion, of the sequence DNA given in FIG. 2(b) or FIG. 13.

In yet another embodiment the present invention relates to polyclonal and monoclonal antibodies specific for either Drosophila or human HSF proteins.

In a further embodiment, the present invention relates to a recombinant DNA molecule comprising a DNA segment encoding all, or a unique portion, of either Drosophila or human HSF protein and a vector.

In yet a further embodiment, the present invention relates to a host cell stably transformed with the above recombinant DNA molecule in a manner allowing expression of the protein encoded in the recombinant DNA molecule.

In a further embodiment, the present invention relates to a method for the detection of HSF proteins in a cell sample which method comprises contacting an antibody which specifically reacts with HSF protein in the cellular sample under conditions such that an antigen-antibody complex between HSF protein and antibody can occur and detecting the presence or absence of the complex.

The entire contents of all publications mentioned herein are hereby incorporated by reference.

DETAILED DESCRIPTION OF THE INVENTION

The present invention relates, in part, to DNA fragments which encode Drosophila HSF protein. Cloned Drosophila HSF protein has a molecular weight, as determined by the deduced amino acid sequence, of 77,300 daltons, which is lower than the 110,000 daltons measured by SDS-gel electrophoresis.

The invention also relates to recombinant Drosophila HSF protein isolated from E. coil which is characterized by specific DNA binding affinity to heat shock elements (HSE) with or without heat treatment. HSF activity remains constant when HSF is expressed either at low levels or high levels in different expression bacteria systems; thus over expression per se does not lead to activation of heat shock proteins.

The invention also relates to recombinant Drosophila HSF synthesized by in vitro translation in rabbit reticulocyte lysates. Recombinant HSF obtained from rabbit reticulocytes have the same activity as described above.

In another embodiment, the present invention relates to DNA fragments which encode human HSF (HUHSF) protein.

The invention also relates to recombinant HuHSF protein isolated from E. coli. Similar to Drosophila HSF, human HSF expressed in E. coli displays the same maximal affinity to HSE, whether or not heat treatment is given.

The present invention also relates to a recombinant DNA molecule comprising a vector and the above described DNA fragment which encodes for either Drosophila or human HSF proteins or a unique portion thereof. Possible vectors include plasmids, for example, pET 3C (rosenberg et al. 1987, Gene 56, 125–135) and other vectors known in the art that stably transform or transfect host cells with the above described recombinant DNA molecule in a manner which allows expression of Drosophila HSF, human HSF, protein fragments or analogs. Examples of appropriate host cells include prokaryotic and eukaryotic cells depending on the vector used.

In another embodiment, the present invention relates to antibodies (monoclonal and polyclonal) specific for either Drosophila HSF or HUHSF protein. Monospecific polyclonal antiserum of the invention reacts with Drosophila HSF protein. The antibodies of the invention can be prepared using methods known in the art. The antibodies can be bound to a solid support such as, for example, agarose, sepharose, plastic nylon membranes or nitrocellulose. Antibodies can be prepared using recombinant Drosophila HSF, human HSF or unique recombinant portions of either Drosophila HSF or human HSF proteins.

The present invention also relates to the detection of HSF in a sample. The sample can be a clinical specimen such as a cell culture. The presence of HSF in the nucleus of a cell, determinative of abnormal stress or a diseased state, can be detected by contacting a reagent antibody which specifically reacts with the HSF protein with the sample under conditions such that a complex between HSF and antibody can be effected and detected.

Furthermore, the present invention relates to detection of human cells in stressed or unstressed states by staining tissue blood cell samples with anti-HSF antibodies, followed by fluorescent, or enzyme-linked secondary antibody reaction, and microscopic examination to check if the HSF is nuclear (active) or cytoplasmic (inactive).

The present invention also relates to detection of human cells in stressed or unstressed states by determining the multimeric state of human HSF in crude or fractionated human cell extract by, for example nondenaturing gel electrophoresis (pore exclusion limit analysis) or by SDS-PAGE after chemical cross-linking with EGS or similar cross-linking reagents, except glutaraldehyde, and specifically visualizing the multimeric state of HSF by staining Western blots with anti-HSF antibodies, followed by secondary antibody reaction. The stressed stated may be estimated by the amount of large HSF multimers (hexamers) present in the sample being tested.

Moreover, the present invention also includes extending the detection systems described above for measuring stress in any living system.

Another embodiment of the present invention relates to novel uses of Drosophila, human or any metazoan HSF as vehicles or vectors for stress-regulated multimerization (hexamerization) of any other protein or peptide which can be fused to the HSF gene or part of the HSF gene by recombinant DNA techniques. The other protein could be another DNA binding protein, and multimerization of this protein could increase the affinity of the DNA binding, or it could be an enzyme whose potency could be increased, or it could be several different proteins, each fused to one subunit of HSF, leading to a multifunctional protein complex. By previously demonstrating that multimerization of Drosophila HSF is regulated, one may devise a method for creating multimeric complexes of proteins in a regulated manner (i.e. using heat, or any other of the known stress inducers). HSF from any species whose multimerization state is regulated by stress can also be used as such a multimerization vector.

The present invention also includes uses of the Drosophila HSF gene, human HSF gene, or HSE genes from other species, linked to a tissue-general or tissue-specific promoter, and introduced in transgenic mice as a tool for eliciting increased or chronic stress response conditions. Such mice might serve as a biological model for how tisses respond to chronic stress conditions, e.g. by viral infection, chemical, or mechanical stress.

The present invention can also be used to increase expression of other gene products by contransfecting HSF gene together with other genes linked to HSEs.

The invention is described in further detail in the following non-limited Examples.

EXAMPLES

The following materials/protocols are referred to in the Examples that follow.
Purification of Drosophila HSF and Digestion with Trypsin HSF was purified as described in Wu et al, (1987) with one modification. Nuclear extract from heat shocked Schneider line 2 cells was purified by chromatography on Heparin-Sepharose CL-6B (Pharmicia) and two affinity chromatography steps on HSC oligo-Sepharose. The HSF fraction from the second affinity column was then fractioned by reverse phase HPLC on a Aquapore RP 300 ($C_8$) column (2.1×30 mm, Applied Biosystems). HSF was eluted by a 10 ml gradient of 0% to 70% acetonitrile in 0.1% TFA, and 100 µl fractions between 35%–50% acetonitrile were collected in siliconized microcentrifuge tubes. In order to identify fractions containing HSF, 5% of each fraction was dried in vacuo in a centrifugal concentrator (Speedvac, Savant), redissolved in sample buffer, subjected to SDS gel electrophoresis, and stained with silver nitrate. The peak of HSF was eluted in one fraction at 44% acetonitrile. In an independent purification, HSF was prepared to the Mono S step (Wu et al, 1987), followed by chromatography on a 30 µl ProRPC $C_1/C_8$ column (Pharmacia), under conditions similar to those described for the Aquapore column.

The remaining 95% of each of the two purified HSF preparations (each about 4 µg, or 40 pmoles) were digested with trypsin essentially according to Stone et al 1989, Enzymatic digestion of proteins and HPLC peptide isolation in the subnanomole range. In: Techniques in Protein Chemistry, T. Hugli, ed. Academic Press, 377–391, in two separate reactions. The HSF fraction was dried in vacuo and redissolved in 8M urea/0.1M ammonium bicarbonate (pH 8.1) at a concentration of 0.5 µg HSF/µl. After addition of one-tenth volume of 45 mM DTT, the sample was incubated for 15 min at 50° C. and cooled to room temperature. The sample was then incubated for 15 min at room temperature with iodoacetamide (0.1 volumes of 0.1M solution, Sigma), followed by dilution with 3 volumes of 0.1M ammonium bicarbonate. Trypsin (Sequencing Grade, Boehringer Mannheim) was added at a weight ratio of 1:30 trypsin:HSF and the sample was incubated for 24 hrs at 37° C. The tryptic digest was diluted with an equal volume of 10% acetronile, 0.1% TFA and loaded on a Vydac $C_{18}$ reverse phase HPLC column (2.1×150 mm, The nest Group) on a Applied Biosystems Model 130A separations system. Peptides were eluted with a gradient of 0% to 50% acetonitrile in 0.1% TFA and individual peaks were collected onto glass fiber filters. The filters were dried in vacuo and subjected to amino acid sequence analysis on an Applied Biosystems 477A Protein Sequencer coupled to a 120A analyzer.

E. coli Strains and Plasmids Used for Recombinant Drosophila expression

For routine cloning and plasmid amplification the strains X1-1 Blue (STRATAGENE) or DH-5a (BRL) were used.

Lambda gt11, EMBL 3 phage, and their derivatives were propagated in strains Y1090 or LE392, respectively. The strain BL21(DE3) (Studier and Moffatt, 1986,) served as host for bacterial expression of HSF. Subcloning of genomic DNA and cDNA inserts, and reconstruction of the full-length HSF cDNA were performed with pBluescript II KS(+) (Stratgene). pHSF poly A contains HSF cDNA (positions −15 to +2540, combined from pHSF407 and pHSF312, see FIG. 2A) inserted in the EcoRU site of pJC1. pJC1 was constructed by fusing a $(dA)_{100}$ sequence derived from the plasmid pSP65AT (Baum et al, 1988, Dev. Biol., 126, 141–149) between the SmaI and BamHI sites of pBluescript II KS(+). This plasmid allows the transcription of HSF RNA containing a poly A tail, under the control of the $T_3$ RNA polymerase promoter for in vitro translation and microinjection studies. The bacterial expression vector pJC10 was constructed by ligation of the ScaI/BglII (blunted) fragment from pET 3C (Rosenberg et al, 1987, Gene, 56, 125–135) which contains the T7φ10 promoter, translation signals and transcription terminator, plus the 5' half of the ampR region, with the ScaI/PvuII fragment from pBluescript II KS(+), containing the 3' half of the ampR region and the col E1 origin of replication. pJC10 is smaller than pET3 and is a high copy-number plasmid allowing high yields in analytical plasmid preparations. pHSFWT was constructed by creation of a NdeI site at the start codon of the HSF cDNA, and ligation of a NdeI-BamHI HSF fragment to pJC10 (linearized with NdeI and BamHI). The NdeI-BamHI fragment contains 2532 nt of HSF sequences from the initiating AUG codon, plus 16 nt at the 3' end from pBluescript II KS(+). Nested deletion mutants were generated by ExoIII/S1 digestion of pHSFWT cleaved at the StuI and ApaIsites (see FIG. 2C) following the manufacturer's protocol (Pharmacia).

Screening of cDNA Libraries for Drosophila HSF

The Drosophila genomic library in EMBL 3 and the oligo dT-primed cDNA library were gifts from John Tamkun and Jim Kennison. The random-primed cDNA library was a gift of Bernd Hovemann. The genomic library was screened by hybridization with two oligonucleotides, oligo 27 and 29, at 37° C. in 6×SSC. The final wash was done at 48° C. in 3.2M tetramethylammonium chloride (TMA-C1) (Wood et al, 1985, Proc. Natl. Acad. Sci. U.S.A., 82, 1585–1588; Devlin et al, 1988, DNA, 7, 499–507). Plaque hybridization of the cDNA libraries in lambda gt11 was carried out as follows: hybridization and washed at 65° C. in 6×SSC and 0.5×SSC, respectively, using an 1800 bp SalI-EcoRI fragment from genomic clone EMBL 3-104. Twelve cDNA clones were isolated, seven of which were sequenced after subcloning into pBluescript II KS(+).

Screening of cDNA Libraries For Human HSF

Approx. $10^6$ plaques of a human B cell lymphoma cDNA library (gift of L. Staudt, NIH) and a human activated B cell cDNA library (gift of J. Kehrl and A. Fauci, NIH; obtained through L. STaudt, NIH) in the lambda gt11 vector were screened. Three nitrocellulose filter replicas were prepared from each plate containing approx. 50,000 plaques. The replicate filters were screened with the human HSF PCR fragment, labeled with $^{32}$P-dCTP by the random prime procedure, and with two oligonucleotides derived from the sequence of the human HSF PCR fragment, labeled with $^{32}$P-gamma-ATP by the kinase reaction. The sequences of the two oligonucleotides are:

5'GATGTTCTCAAGGAGCTGCTCCTGGC-
CACGCAGGAAGCATGGTGCTGGAA CTCC and

5'AAGCACAACAACATGGCCAGC/TTTCA (See SEQ ID NOS:1 and 7, respectively)

The coordinates of the human HSF PCR fragment sequence are +45 to +513 on the sequence shown in FIG. 13.

Filters were prehybridized with 6×SSC, 5× Denhardt's solution, 0.1% SDS for 1 hr at 65° C., and hybridized with labeled DNA under the same conditions for 12–16 hr. Filters were then rinsed trice with 1×DSD, at 65° C. for 15 min, rinsed briefly in 1×SSC, blotted dry and exposed to X-ray film for approx. 16 hr. Only plaques which gave reaction with all three probes were considered positive. After three rounds of plaque purification, the cDNA inserts were subcloned into the vector pBluescript SK− for sequence determination by the dideoxynucleotide technique.

Preparation of Drosophila HSF RNA and Translation In Vitro

20 µg/ml pHSFpolyA was cleaved with XbaI and incubated for 60 min at 37° C. in a 50 µl volume containing 40 mM Tris-HCl, pH 8.0, 8 mM $MgCl_2$, 5 mM DTT, 4 mM spermicide, 400 mM each of ATP, CTP, UPT, and $m_7G(5')$ ppp(5')Gm, 40 mM GTP, 50 µg/ml BSA, 1000 units/ml of RNase Inhibitor (Boehringer Mannheim) and 40 units/ml of $T_3$ RNA polymerase (Boehringer Mannheim). RNA was extracted with phenol-chloroform, precipitated with ethanol and redissolved in HPLC grade water (Fisher Scientific).

Rabbit reticulocyte lysate (Promega) was treated with Staphylococcus aureus nuclease (Boehringer Mannheim) as directed in Sanbrook et al. Molecular Cloning: A laboratory Manual 1983. 1 µg of in vitro-transcribed HSF RNA was translated for 2 hrs at either 25° C. or 30° C., in a 25 µl volume containing 50% translation lysate, 20 µM of each amino acid, 1000 units/ml RNase Inhibitor, and 0.2 mCi/ml $^{35}$S-methionine (1000 Ci/mmole, DuPont-NEN). Small aliquots of the reaction were subjected to SDS gel electrophoresis and fluorography to verify the translational efficiency and accuracy. The remainder was frozen in liquid nitrogen and stored at −80° C.

Expression and Purification of Recombinant Drosophila HSF in E. coli

BL21(DE3) cells transformed with pHSFWT orits derivatives were grown at 37° C. to $OD_{600}$=0.6 in M9TB/amp medium (10 g Bacto-Tryptone (Difco), 5 g NaCl, 1 g $NH_4Cl$, 3 g $KH_2PO_4$, 6 g $Na_2HPO_4$, 4 g glucose, 1 mM $MgSO_4$, and 50 mg ampicillin/liter). IPTG was added to 0.4 mM, and the cultures were transferred to 18° C. After 40 to 60 min incubation, 40 mg of rifampicin was added to suppress transcription by bacterial RNA polymerase, and incubation was continued at 18° C. overnight, with shaking. Bacteria were pelleted by centrifugation (6000×g, 10 min, at room temperature), and resuspended in 1/100 volume of buffer CB+400 mM KCl (buffer CB: 20 mM HEPES pH 7.6, 1.5 mM $MgCl_2$, 0.1 mM DTT, 2 mM leupeptin, 10% (v/v) glycerol). After disruption by sonication at 100 mW for 2 min (B. Braun), the lysate was incubated for 30 min on ice. The bacterial debris was removed by centrifugation (6000× g, 10 min 4° C.) and the supernatant was diluted 2-fold with buffer CB and centrifuged at 100,000×g at 4° C. for 1 hr. The supernatant containing crude recombinant HSF was frozen in liquid nitrogen and stored at −80° C.

In order to purify recombinant HSF, 40 ml of the crude supernatant was diluted with buffer CB to a KCl concentration of 100 mM and chromatographed on a 20 ml Heparin-Sepharose CL-6B column. HSF was diluted with a linear KCl gradient (100–500 mM) in buffer CB. HSF activity was monitored by gel mobility shift assays and active fractions were diluted to 100 mM KCl with buffer CB. HSF was further chromatographed on a 1 ml Mono Q column (Pharmacia), and eluted with a linear KCl gradient (100–500 mM) in buffer CB. Active fractions contained the 105 kD HSF protein purified to 90% homogeneity, as determine by SDS gel electrophoresis and silver staining. The total protein concentration was 3.5 mg/ml, as determined by a dyebinding assay (Biorad).

Gel Mobility Shift Assay

DNA-binding was monitored by the gel mobility shift assay as described previously (Zimarino and Wu, 1987, *Nature*, 327, 727–730), using a double-stranded, synthetic HSE carrying three [__GAA__] repeats in alternating orientation (Zimarino et al, 1990, *Mol. Cell. Biol.*, 10, 752–759). The DNA was labeled with $^{32}P$ by primer extension as described previously (Wu et al, 1987, *Science*, 238, 1247–1253). For the experiments shown in FIG. 3A, 2 µl samples of protein were mixed with 10 fmole of $^{32}P$-labeled HSE, 2.5 µg of poly (dI-dC) poly (dI-dC), 5 µg yeast tRNA, 0.5 µg of sonicated *E. coli* DNA and 0.5 µg of poly (dN)$_5$ in 10 µl of 10 mM HEPES pH 7.9, 1.5 mM MgCl$_2$, 0.05 mM EDTA, 120 mM NaCl, and 6% glycerol. Samples were incubated on ice for 10 min and electrophoresed on a 1.2% agarose, 0.5×TBE gel. The gel was blotted and dried onto DE 51 paper and autoradiographed.

DNase I Footprinting

DNA fragments labeled with $^{32}P$ at one 5' end were synthesized by the polymerase chain reaction (PCR) using a combination of one 5' labeled oligonucleotide primer and one unlabeled primer. An XhoI-Acc I fragment (positions −185 to +295) from the hsp70 gene promoter (locus 87A) cloned into pBluescript I SK(+) served as template for the PCR. The oligonucleotide primers used were: hsp70 lower stand positions +149 to +177, T$_7$ sequencing primer (Stratagene), hsp70 upper strand positions −140 to −120, and hsp70 lower strand positions +10 to +29. 50 fmoles of the labeled DNA fragment was incubated at room temperature with recombinant HSF extracted from *E. coli* under the same conditions as described for the gel mobility shift assays. After 10 min, DNase I (Pharmacia) was added (300 u/ml) and the incubation was continued for another 2 min. The reaction was stopped by the addition of EDTA and SDS to 10 mM and 1%, respectively, and the DNA was extracted with phenol-chloroform and precipitated with ethanol. Primers that were 5' end-labeled for the polymerase chain reaction were also used for dideoxy sequencing reactions as a reference.

In Vitro Transcription

Two supercoiled plasmid templates were used for in vitro transcription. phsp70(−50)HSE$_2$ carries a modified hsp70 promoter in a pBluescript vector (Stratagen). The modified hsp70 promoter consists of hsp70 (locus 87A) sequences from −90 to +296, in which two upstream HSEs were remodeled according to Xiao and Lis 1988, *Science*, 239, 1139–1142, keeping the natural spacing between the HSEs and the hsp70 TATA box. phsp70(−50) minigene is similar to phs70(−50)HSE$_2$, except for a deletion of a 30 bp, AluI fragment between +41 and +71, and substitution of sequences from −50 to −90 (containing the HSEs) with a synthetic polylinker.

Transcription extracts were prepared from 0–12 hr *D. melanogaster* (Oregon R, P2) embryos (Soeller et al, 1988, *Genes Dev.*, 2, 68–81; Biggin and Tjan, 1988, *Cell*, 53, 699–711). Care was taken not to inadvertently heatshock the embryos. Protein from the ammonium sulfate precipitation step was dialyzed to a conductivity equivalent to HEMG:100 mM KCl and stored in aliquots at −80° C. (HEMG; Soeller et al, 1988). Transcription with crude embryo extracts was performed according to Heberlein et al (1985), *Cell*, 41, 965–977, modified as follows for RNA recovery: after addition of 100 µl stop mix (minus SDS) and 100 µl phenol to the transcription reactions, the samples were mixed in an Eppendorf shaker for 2 min. 100 µl of chloroform:isoamyl alcohol 241 was added and the mixing was repeated. The aqueous phase was transferred to a fresh tube, re-extracted with organic solvent, and nucleic acids were precipitated with ammonium acetate. After thorough washing with 80% ethanol, the pellet was dried in vacuo and dissolved in 9 µl of 250 mM KCl, 2 mM Tris-HCl, pH 7.9, 0.2 mM EDTA. 1 µl of $^{32}P$-labeled primer (hsp70 positions +149 to +177) was added, and the primer was annealed by incubation at 75° C. for 5 min, and at 42° C. for 20 min. After addition of 25 µl of 50 mM Tris-HCl, pH 8.3, 10 mM MgCl$_2$, 5 mM DTT, 1 mM EDTA, 1 mM each dNTP, the primer was extended with 7 units AMV reverse transcriptase (Promega) at 42° C. for 45 min.

Translation of HSF RNA by Microinjection in *Xenopus* oocytes

*Xenopus laevis* females were obtained from Nasco or Xenopus 1. Pieces of ovary were surgically removed and the connective tissue digested with 0.2% collagenase (Sigma type II) in OR-2 medium (Wallace et al, 1973, *J. Exp. Zool.*, 184, 321–334). Stage VI oocytes were incubated for about 12 hours in OR-2 with 1 mM oxaloacetate as exogenous energy source (Eppig and Steckman, 1976, In Vitro, 12, 173–179) before microinjection. All procedures were performed at 16°–18° C., except where indicated.

HSF RNA was adjusted to a concentration of approximately 0.4 ng/nl in injection buffer (90 mM KCl, 15 mM Hepes, pH 7.5). Approximately 25 nl (10 ng) of RNA was injected into each oocyte using a micropipet attached to an adjustable 10 µl Drummond pipettor as described (Westwood, 1988, Abnormal proteins and the induction of heat-shock gene expression. Ph.D. thesis, University of California, Berkeley). After 10 hours, groups of injected *oocytes* were transferred to 1.5 ml microfuge tubes containing approximately 50 µl of OR-2 medium, and heat-shocked at 36° C. for 10 min. Non-shocked *oocytes* were left at 18° C. The medium was removed and the *oocytes* rinsed quickly with 100 µl 0° C. homogenization buffer (50 mM KCl, 10 mM Hepes, pH 7.9, 0.5 mM PMSE, 0.5 mM DTT). Individual *oocytes* were transferred to fresh tubes, and homogenized by repeated pipetting with a micropipettor (10 µl buffer per *oocyte*). The lysate was centrifuged for 5 min at 12,000×g at 4° C., and the supernatent transferred to a fresh tube, avoiding the top lipid layer. Extracts were either frozen in liquid nitrogen or assayed immediately by the gel mobility shift technique (5 µl extract in a 10 µl final volume).

Pore Exclusion Limit Electrophoresis 0.5 µl (2.5 µg) of recombinant HSF purified to the Mono Q step, and high molecular weight marker proteins (Pharmacia #17-0445-01), were electrophoresed on a 4–20% polyacrylamide gradient gel in 0.5×TBE buffer. Electrophoresis was continued for 24 hours the duration of electrophoresis was necessary for proteins to have migrated to their exclusion limit (Andersson et al, 1972, *FEBS Letters*, 20, 199–201).

Size estimation of the HSF-HSE complex was performed by electrophoresis of a mixture of HSF and $^{32}P$-labeled HSE (under standard gel-shift assay conditions) on a 3–12% polyacrylamide gradient gel in 0.5×TBE buffer, as above. The gel was stained with Coomassie Blue, destained, equilibrated in water, dried, and autoradiographed.

Chemical Cross-Linking

2 µg of cloned Drosophila HSF (Mono Q fraction) was incubated with glutaraldehyde or EGS (Pierce) at room temperature for 10 min in 10 µl of 175 mM NaCl, 15 mM Tris-HCl, pH 8.0, 0.1 mM EDTA, and 1.5 MM $MgCl_2$. Reactions were quenched with 30 mM lysine and 1 volume of 2× Laemmli sample buffer. Samples were heated to 95° C. for 5 min; aliquots were separated on a SDS 4–6% polyacrylamide gel without a stacking gel, and silver-stained.

In Situ Hybridization

Preparation of chromosomal squashes for in situ hybridization followed standard procedures (Ashburner, 1989, Drosophila. A Laboratory Manual. Cold Spring Harbor Laboratory Press). The DNA probe was substituted with digoxigenin-dUTP by a random priming reaction, and hybrids were detected according to instructions supplied with the Genius kit (Boehringer Mannheim).

Preparation of Rabbit Polyclonal Antibodies to Cloned Drosophila HSF Protein

Cloned Drosophila HSF purified as described above was used an antigen for immunization. A dose of 500 µg protein per rabbit, mixed with Freund's adjuvant was injected intradermally, followed two booster injections of 250 µg protein each at 3 week-intervals. Serum was collected and stored at −70° C.

Western Blotting of Nondenaturing Polyacrylamide Gradient Gels

After electrophoresis, the gel was incubated in transfer buffer (48 mM Tris, 39 mM glycine) containing 0.25% SDS for 10 min at 75° C. and allowed to cool to room temperature before electroblotting for 4 hr at 100 mA onto an Immobilon P membrane (Millipore) in transfer buffer containing 0.05% SDS, using a Novex semi-dry blotting apparatus. After blotting, the membrane was stained with 0.2% ponceau S (in 3% trichloroacetic acid, 3% sulfosalycic acid), and destained briefly to visualize the molecular weight markers. The membrane was then processed for immunostaining with 1:1000 dilution of rabbit anti-Drosophila HSF polyclonal antibodies and 1:40,000 dilution fo goat anti-rabbit antibody conjugated with alkaline phosphatase, according to manufacturer's instructions (Tropix). A chemiluminescent substrate (Tropix) was employed to visualize the presence of secondary antibody. The membrane was wrapped in Saran wrap and exposed to X-ray film.

EXAMPLE 1
Purification and Microsequencing of Drosophila HSF

Drosophila HSF was purified to about 95% homogeneity by a modification of the procedure described previously (Wu et al. 1987) (FIG. 1A). Two independently-purified, 4 µg preparations of the 110 kD polypeptide were digested with trypsin, and the resulting peptides were subjected to reverse phase liquid chromatography (RPLC). Essentially identical elution profiles were observed for both peptide preparations. Individual HSF peptides were subjected to microsequence analysis, and the amino acid sequence of six peptides that yielded identical sequences in duplicate are shown in FIG. 1B.

EXAMPLE 2
Isolation of cDNA Clones for Drosophila HSF

Figure 2A:
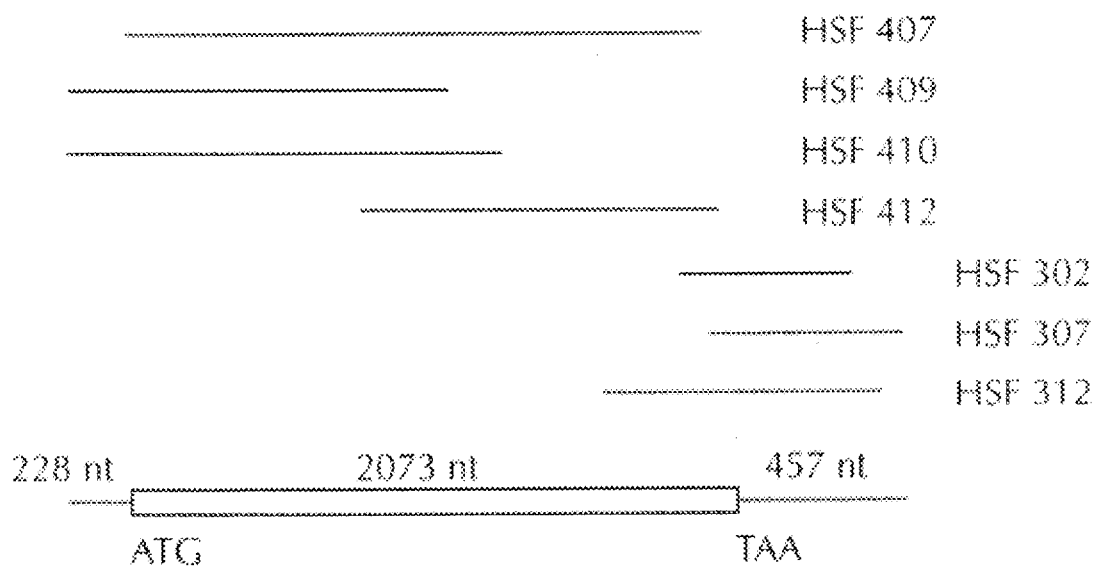

Two 20-mer oligonucleotides with 32-fold degeneracy, based on the predicted nucleotide sequences of HSF peptide 27 and peptide 29 (FIG. 1B), were used to probe a Drosophila genomic library. Initially two genomic DNA clones were identified which contained a common, 1800 nt SalI-EcoRI fragment. This SalI-EcoRI fragment, which hybridized with both oligonucleotide probes, was then used to isolate cDNA clones from a random-primed and an oligo dT-primed cDNA library. The 2.8 kb of HSF cDNA sequence reconstructed from six overlapping cDNA clones reveals a single open reading frame of 691 amino acids (2073 nt) (FIG. 2A). The sequences of all six HSF tryptic peptides within the 691-amino acid open reading frame were located, and thus concluded that this reading frame encodes Drosophila HSF (FIG. 2B). The molecular mass of Drosophila HSF, calculated from the deduced amino acid sequence is 77,300 daltons, significantly lower than the apparent mass of 110,000 daltons measured by SDS gel electrophoresis (Wu et al, 1987). Evidently, Drosophila HSF has an anomalous mobility on SDS gels; a similar anomaly was observed with yeast HSF (Sorger and Pelham, 1988, Cell, 54, 855–864; Wiederrecht et al. 1988, Cell, 54, 841–853). For purposes herein, the molecular size of HSF protein as measured by SDS gel electrophoresis will be used throughout the examples. The Drosophila HSF protein sequence predicts an acidic protein (pI=4.7). The overall distribution of charged residues along the length of the protein sequence is nonuniform: the N-terminal one-third of HSF (amino acids 1–240) is relatively basic (predicted pI=10.25), while the C-terminal two-thirds (amino acids 240–691) is reactively acidic (predicted pI=4.1). In addition, there is an unusual N-terminal cluster of 9 acidic residues in a row (amino acids 18 to 26).

Figure 2C:
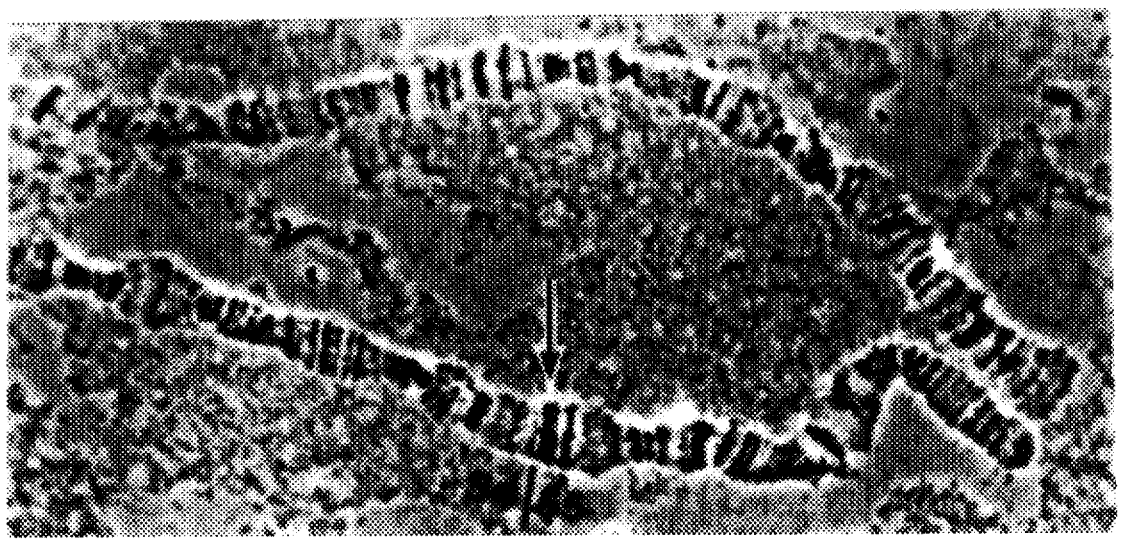
Figure 2B-2:
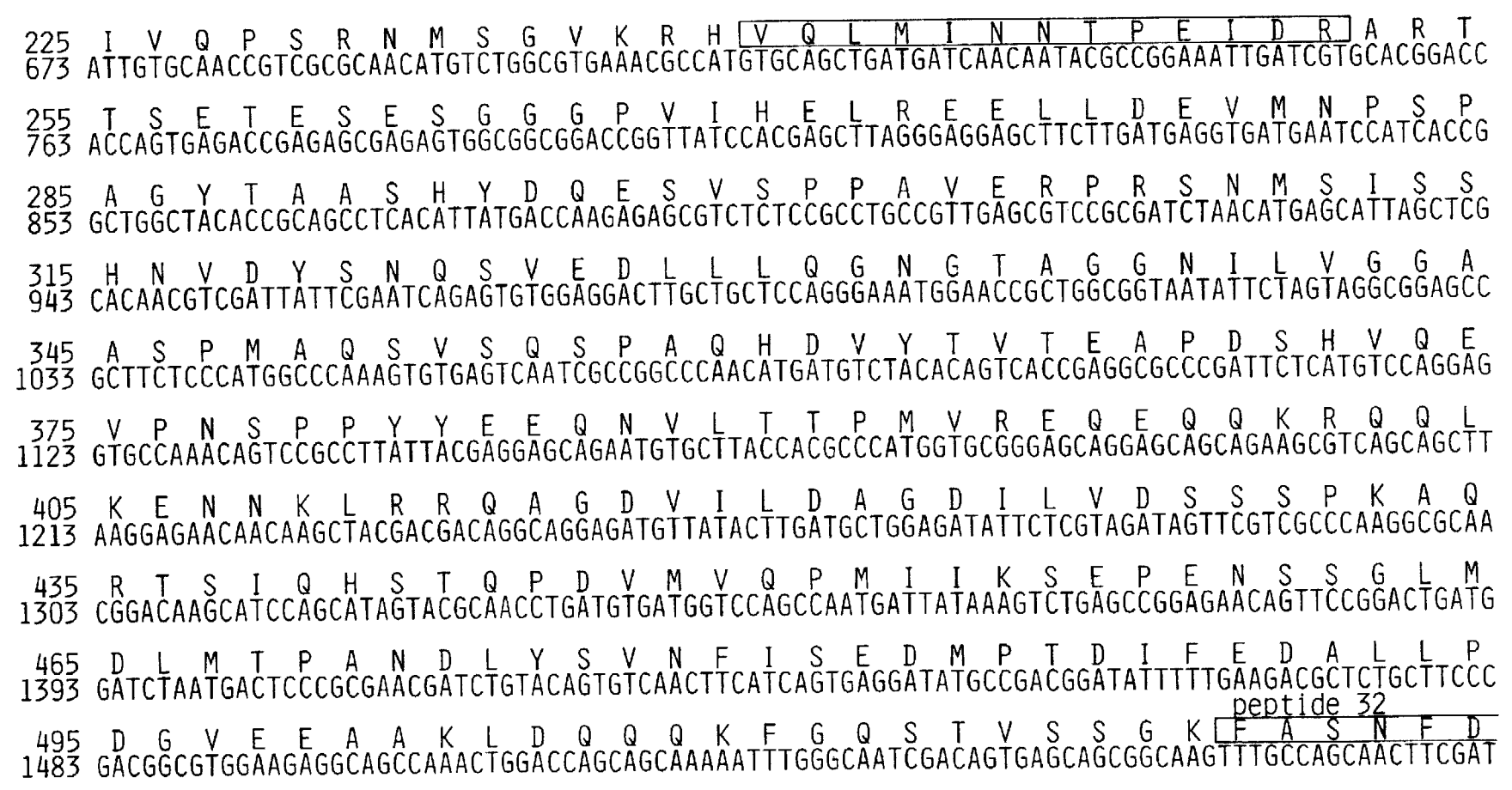

DNA gel blot analysis under standard stringency conditions shows that the Drosophila HSF gene is single-copy. The possible presence of homologous genes that have partial sequence similarity to HSF has not yet been addressed. The Drosophila HSF gene was localized by in situ hybridization to cytological position 55A on the Drosophila polytene chromosome (FIG. 2C).

EXAMPLE 3
DNA Binding Activity of Recombinant Drosophila HSF in the Absence of Heat Shock Naturally occurring HSF extracted from the cytosol of nonshocked Drosophila cells shows a basal affinity for DNA, which can be significantly increased by a direct heat treatment in vitro, or by reaction with polyclonal antibodies raised to the in vivo-activated form of HSF (Zimarino et al. 1990, Science, 249, 546–549; FIG. 3A, lanes 1–3). The slower mobility of the HSF:HSE complex upon anti-HSF treatment is due to the additional binding of antibody. When recombinant HSF was synthesized by in vitro translation in a rabbit reticulocyte lysate at 25° C., or at 30° C., neither heat treatment (34° C.) nor reaction with anti-HSF serum increased HSF affinity for DNA (FIG. 3A, lanes 4–9). The low activity of HSF translated at 25° C. is due to reduced translational efficiency at this temperature. The specific binding of HSF translated in vitro was demonstrated by a DNA competition experiment (FIG. 3B). The constitutive DNA binding activity of HSF synthesized in vitro could be due to an activating substance in the reticulocyte lysate. However, it was found that reticulocyte lysates do not activate HSF when incubated with cytosol from unshocked Drosophila cells.

Figures 1, 3C:
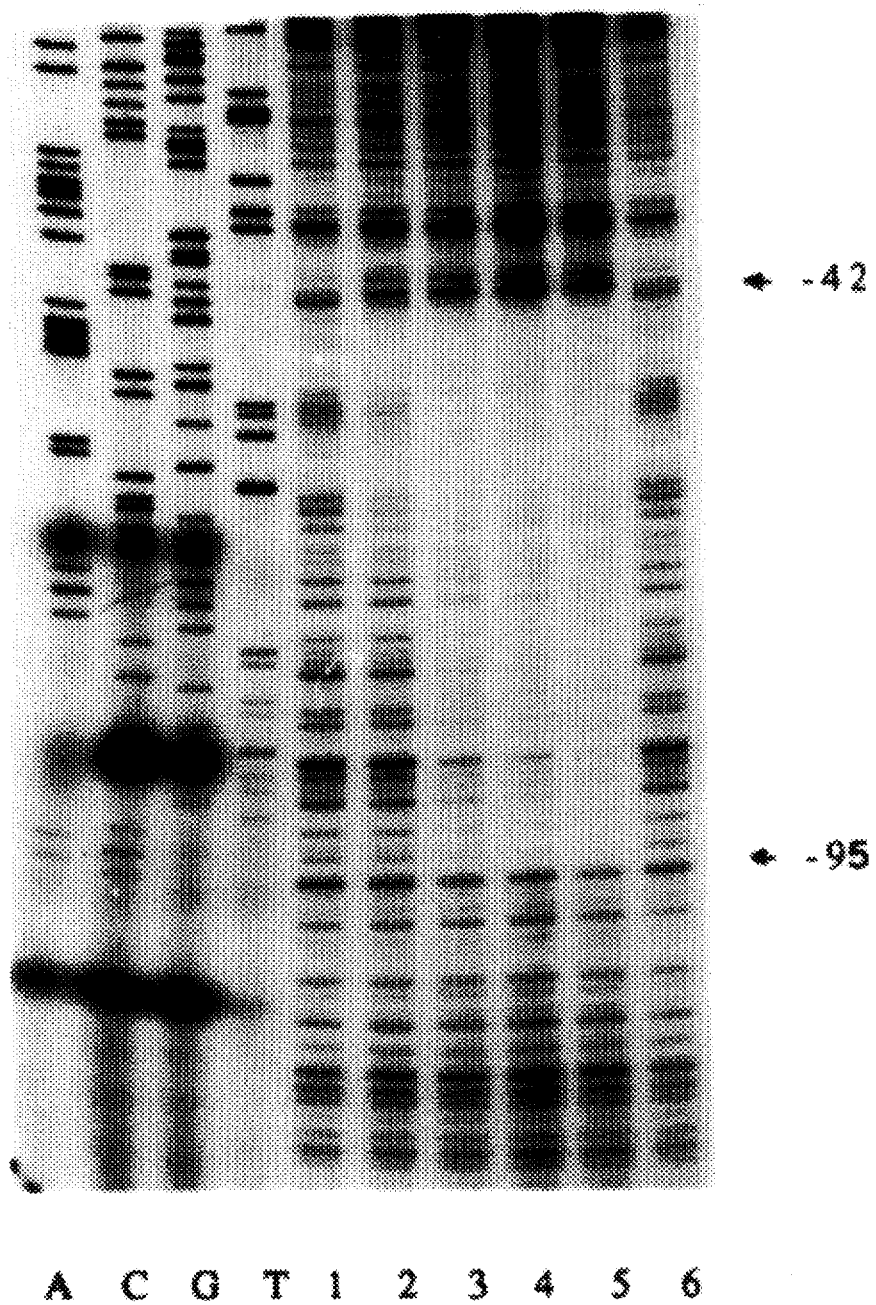
Figures 2, 3C:
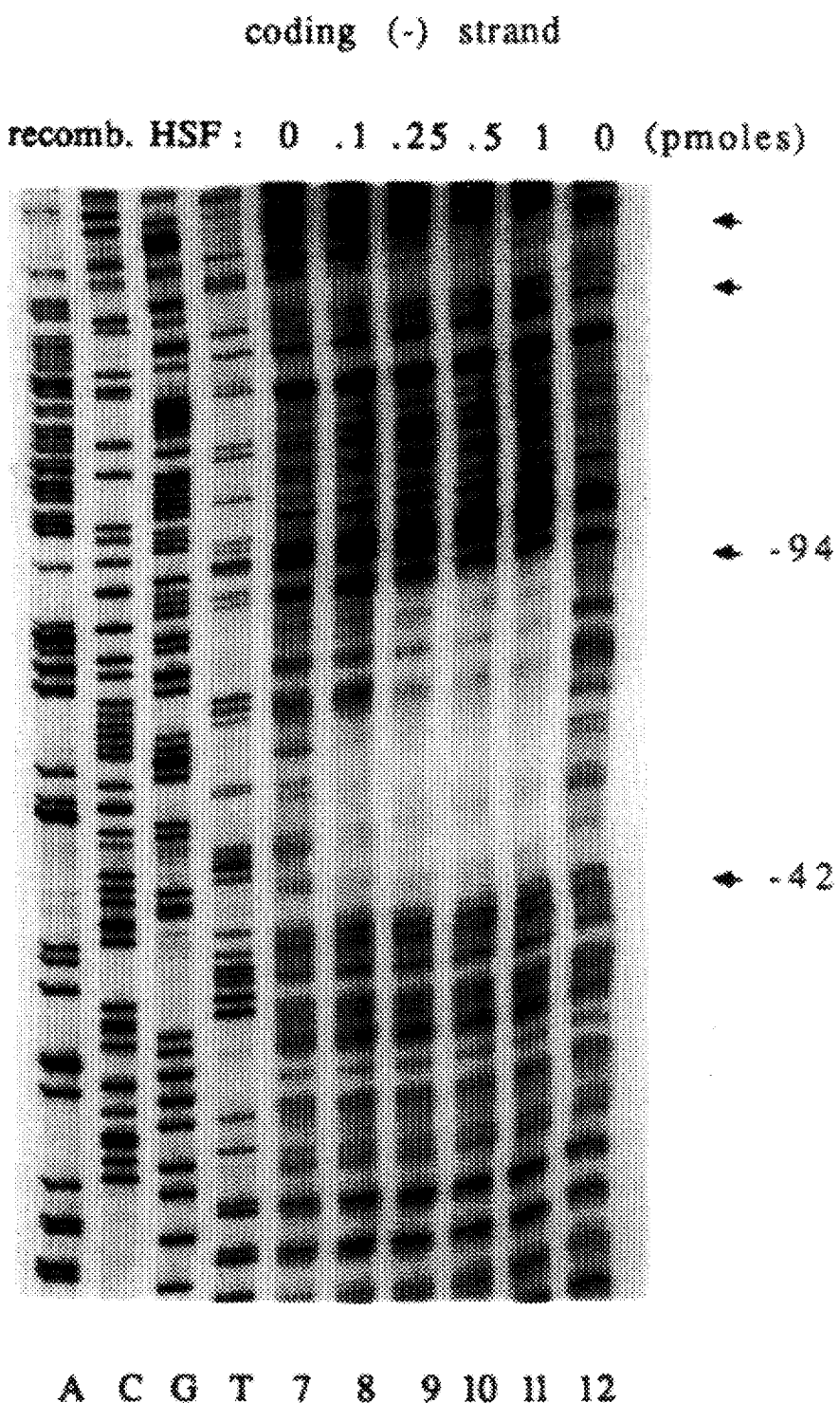
Figure 3D:

HSF was over-expressed in E. coli at 18° C. using the T7 RNA polymerase-dependent expression system (Studier and Moffatt, 1986, J. Mol. Biol., 189, 113–130). Recombinant HSF isolated from E. coli showed maximal DNA binding affinity without heat or anti-HSF treatment; see also FIG. 6C, lanes 3,4). HSF expressed at low levels in bacteria also shown maximal affinity without heat or anti-HSF serum treatment; hence, over-expression per se does not lead to activation. Specific binding of HSF produced in E. coli was confirmed in vitro by a DNase I protection assay, which shows binding to the HSEs upstream of the hsp70 gene (FIGS. 3C, 3D). The DNase I protection pattern is identical to the pattern obtained with natural HSF purified from heat shock Drosophila cells (Wu et al, 1987). The data suggest that recombinant HSF protein synthesized outside the environment of a higher eukaryotic cell has an intrinsic affinity for DNA.

Figure 4:
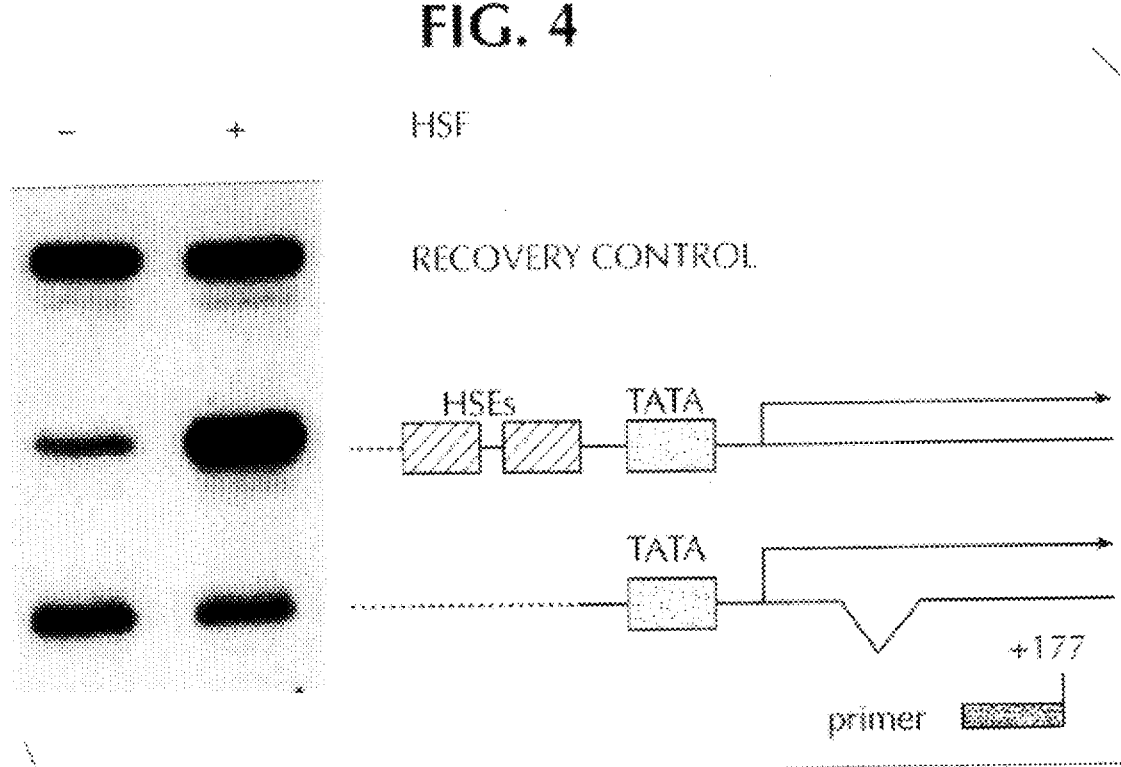
FIG. 4 shows the transcriptional stimulation by recombinant Drosophila HSF in vitro. Primer extension analysis of RNA synthesized by nonshocked Drosophila embryo transcription extracts supplemented with 0.2 µl of *E. coli* extract from HSF expressing cells (+), or with extract from cells transformed with the expression vector only (−). As an internal control for transcription from the template carrying two HSEs, the same template deleted of the HSEs (as well as a 30 bp downstream region) was mixed in the reaction. RNA originating from the template lacking HSEs is thus distinguished by a 30 nt decrease in size. As a further control for RNA recovery, a defined amount of RNA synthesized from a $T_7$ promoter upstream of the hsp70 sequences inserted into pBluescript was introduced into each transcription reaction along with the stop solution. Schematic drawings of the two templates are aligned with the primer extension products of the respective transcripts.

The ability of HSF produced in *E. coli* to function as a transcription factor in an in vitro transcription system derived from Drosophila embryos (Soeller et al, 1988, *Genes Dev.*, 2, 68–81); Biggin and Tjian, 1988, *Cell*, 53, 699–711) was examined next. Addition of the recombinant protein to the transcription extract resulted in a 7-fold increase of transcription from a promoter carrying two HSEs, relative to the transcription from the same promoter lacking HSEs (FIG. 4). Hence, recombinant HSF protein is capable of functioning as a transcription factor in a binding site-dependent manner, apparently without further modification by a heat shock-induced enzymatic activity.

Figure 5:
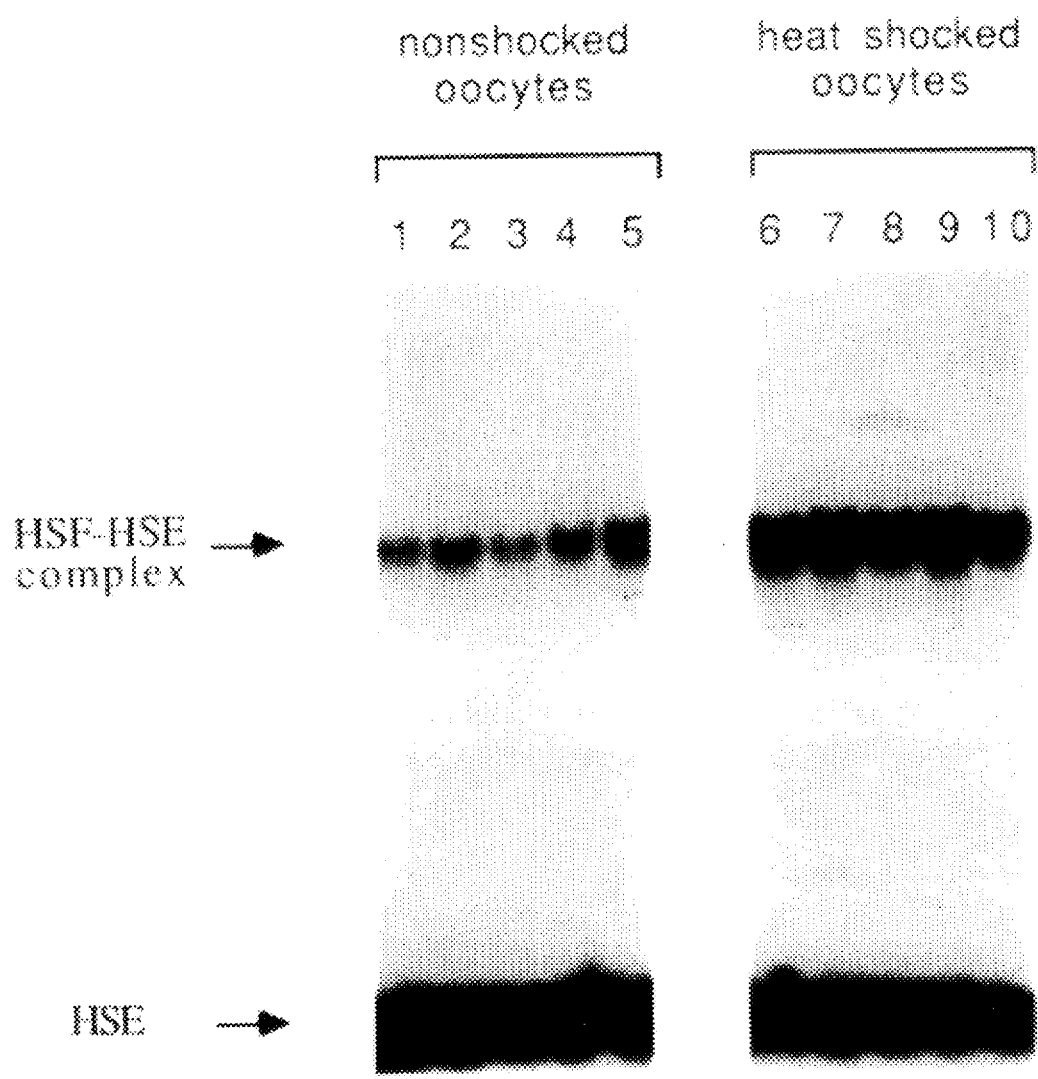
FIG. 5 demonstrates the DNA-binding activity of HSF expressed in *Xenopus oocytes*. Gel mobility shift assay of HSF extracted from individual *oocytes*. Extracts of each of five nonshocked (18° C.) *oocytes* (lanes 1–5), and five heat shocked (36° C., 10 min) *oocytes* (lanes 6–10) were individually analyzed. The positions of the HSF-HSE complex and free HSE are indicated.

EXAMPLE 4
Heat Shock-Inducible DNA Binding Activity of Recombinant Drosophila HSF Expressed in *Xenopus* oocytes Naturally occurring HSF in crude extracts of unshocked Drosophila, Xenopus, and vertebrate cells shows a basal affinity for DNA by in vitro assays, which is increased about 10-fold when cells are induced by heat shock (Zimarino et al, 1990, *Mol. Cell. Biol.*, 10, 752–759). In this example, the activity of recombinant HSF synthesized after microinjection of *Xenopus* oocytes with HSF RNA transcribed in vitro was tested. The endogenous Xenopus HSF is undetectable in these experiments. Although there is some fluctuation in the basal DNA binding activity is of the recombinant protein in crude extracts in individual unshocked *oocytes* (FIG. 5, lanes 1–5), DNA binding activity is insignificantly induced (5-fold, on average) after heatshock for 10 min (FIG. 5, lanes 6–10). The amount of Drosophila HSF protein synthesized in *oocytes* subjected to heatshock was equivalent to the synthesis in control *oocytes*, as determined by $^{35}$S-methionine incorporation and SDS gels electrophoresis. Thus, in contrast to the full DNA binding capacity of HSF synthesized in *E. coli* or in a reticulocyte lysate, the intrinsic affinity of HSF for DNA is suppressed in nonshocked *Xenopus* oocytes. The results suggest that the naturally occurring form of HSF unshocked Drosophila cells is under negative control, which is relieved upon heat shock.

Figure 6A:
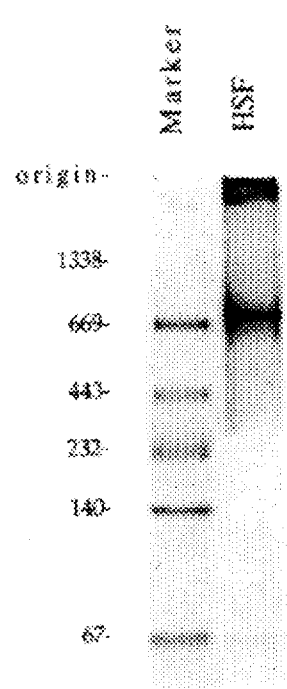
FIGS. 6A, 6B, 6C and 6D show the estimation of the native size of cloned Drosophila HSF. (A) Pore exclusion limit analysis of HSF. Purified, cloned HSF (5 µg/12 µl sample volume) was electrophoresed on a nondenaturing 4–20% polyacrylamide gel until the limit of migration was reached. The gel was stained with Coomassie Blue. The marker lane shows molecular weight markers: thyroglobulin tetramer (1338 kD), thyroglobulin dimer (669 kD), apoferritin (440 kD), catalase (232 kD), lactate dehydrogenase (140 kD) and bovine serum albumin (67 kD). (B) Pore exclusion limit analysis of the HSF:$^{32}$P-HSE complex. 3 µl of Drosophila SL-2 cell cytosol (lanes 1,2) and 0.5 µl of an extract *E. coli* expressing HSF (lanes 3,4) were heat shocked (+) in vitro at 34° C. or incubated at 0° C. (−) for 10 min. The samples were incubated for 10 min with $^{32}$P-labeled HSE tinder standard gel shift conditions, and electrophoresed on a nondenaturing, 3–12% polyacrylamide gradient gel until the limit of migration. The gel was stained with Coomassie Blue, dried and subjected to autoradiography. The positions of marker proteins are indicated. (C) Glutaraldehyde cross-linking of cloned HSF. Purified HSF (2 µg/10 µl) was treated for 5 min at room temperature with glutaraldehyde as indicated. After quenching, about 1 µg of cross-linked HSF was separated on a 4–6% SDS polyacrylamide gel, and silver stained. The minor polypeptides below the 105 kD HSF protein probably represent degradation products. The marker lane contain cross-linked phosphorylase b (Sigma); cross-linked thyroglobulin was also used as a marker. (D) Therefor EGS cross-linking of cloned HSF. Lanes 1–5: purified HSF (2 µg/10 µl) was treated for 10 min at room temperature with EGS as indicated. Lanes 6,7: similar EGS treatment of HSF diluted to 2 µg/ml. The cross-linked products were precipitated with 15% TCA, washed twice with ice-cold acetone, and dissolved in Laemmli sample buffer. Cross-linked products were analyzed by SDS gel electrophoresis as above. Introduction of ovalbumin into the cross-linking reaction revealed no interaction between HSF and the monomeric ovalbumin protein.

EXAMPLE 5
Recombinant Drosophila HSF Expressed in *E. coli*. Associates as a Hexamer in Solution The apparent molecular mass of recombinant HSF, purified from *E. coli* extracts, was determined to be about 105 KD by SDS polyacrylamide gel electrophoresis (see FIG. 6). This size is in agreement with the apparent mass (110 kD) of the natural protein purified from Drosophila cells (Wu et al, 1987, *Science*, 238, 1247–1253); the 5 kD difference could be due to gel mobility fluctuations or to post-translational modification of the natural protein. The native size of recombinant HSF was estimated by pore exclusion limit analysis (Anderson et al, 1972, *FEBS Letters*, 20, 199–201). In this procedure, proteins are electrophoresed for extended periods (about 24 hr) on nondenaturing polyacrylamide gradient gels; each protein migrates until it reaches the pore exclusion limit, which is dependent, to a first approximation, on the size of the protein. A native HSF molecule that migrates with an estimated size of 690 kD is observed (FIG. 6A). Minor aggregates migrate above and below the 690 kD species and very large aggregates are also visible near the origin of electrophoresis.

Figure 6B:
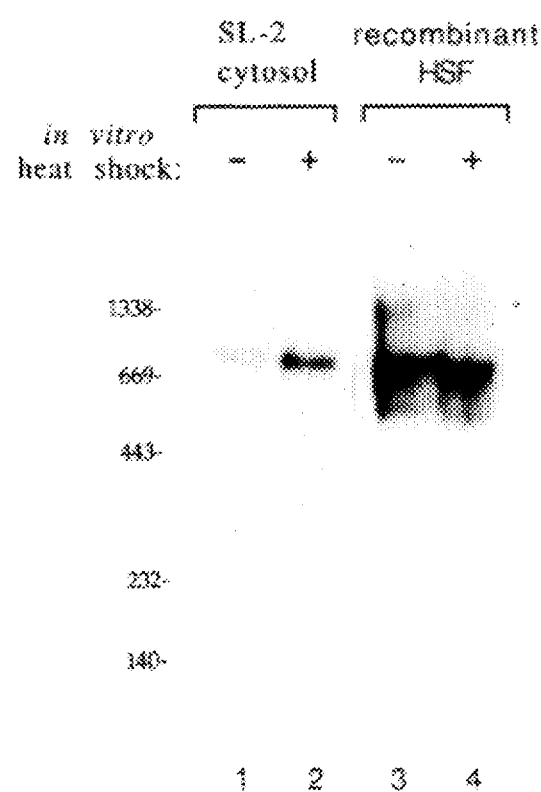

The native size of cloned Drosophila HSF bound to the HSE was estimated by pore exclusion limit analysis of the protein-DNA complex (Huet and Sentenac, 1987, *Proc. Nat. Acad. Sci. U.S.A.*, 84, 3648–3652; Hooft et al, 1987, *Nucleic Acids Res.*, 15, 7265–7282). Using recombinant HSF expressed in *E. coli*, a HSF: $^{32}$P-labeled HSF complex which migrates with a size of 690 kD was observed, similar to the HSF hexamer free in solution (FIG. 6B, lanes 3,4). Since the HSE contribution to the overall protein-DNA complex is negligible (assuming one native HSF molecule binds to one or several HSEs), this result suggests that the hexamer is the active, DNA binding form of HSF. HSF-HSE complexes are not detected in the vicinity of the origin of electrophoresis, suggesting that the very large HSF complexes observed in FIG. 6A are aggregates which lack biological activity. The complex of HSE bound to naturally occurring HSF in crude Drosophila cell cytosol after in vitro heat activation was also sized. The mobility of the natural Drosophila HSF:HSE complex was found to be similar to the mobility of the recombinant HSF:HSE complex (FIG. 6B, lanes 1,2). Together, these results suggest that the active form of natural Drosophila HSF free in solution and when bound to DNA may be a hexamer of the 110 kD subunit.

Figure 6C:
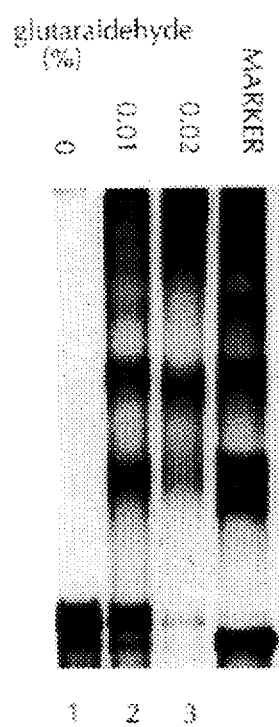
Figure 6D:
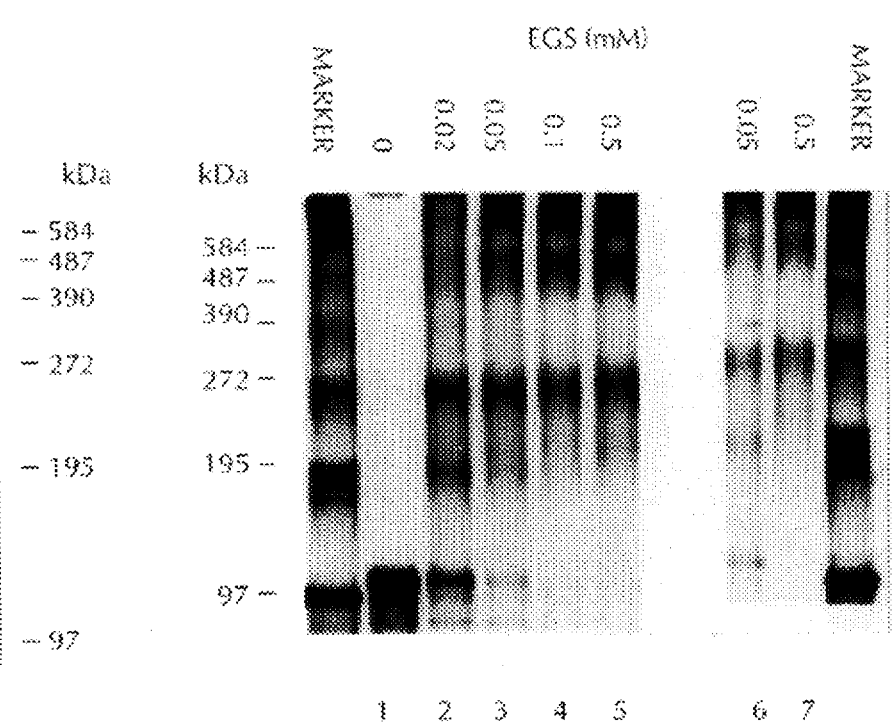

The multimeric state of cloned Drosophila HSF was confirmed by chemical cross-linking. Cloned Drosophila HSF protein cross-linked with limiting amounts of glutaraldehyde (Landschulz et al., 1989, *Science*, 243, 1681–1688) and analyzed on an SDS gel displayed a ladder of cross-linked products whose apparent sizes are approximate multiples (up to six) of the 105 kD HSF monomer (FIG. 6C, lane 2). HSF oligomers were sized relative to cross-linked phosphorylase b markers (97 kD monomer). Increasing the glutaraldehyde concentration enhanced the abundance of HSF trimer and hexamer, in addition to larger species at the limiting mobility of the gel. Similar results were obtained with the bifunctional reagent BGS (Abdella et al, 1979, *Biochem. Biophys. Res. Com.* 87, 734–742) (FIG. 6D, lanes 1–5). More importantly, a 100-fold dilution of cloned HSF protein (to 2 μg/ml) gave essentially the same abundance of HSF oligomers (FIG. 6D, lanes 6, 7), suggesting that the multimerization of HSF is not due to an artifically high concentration of the cloned protein.

Figure 7A:
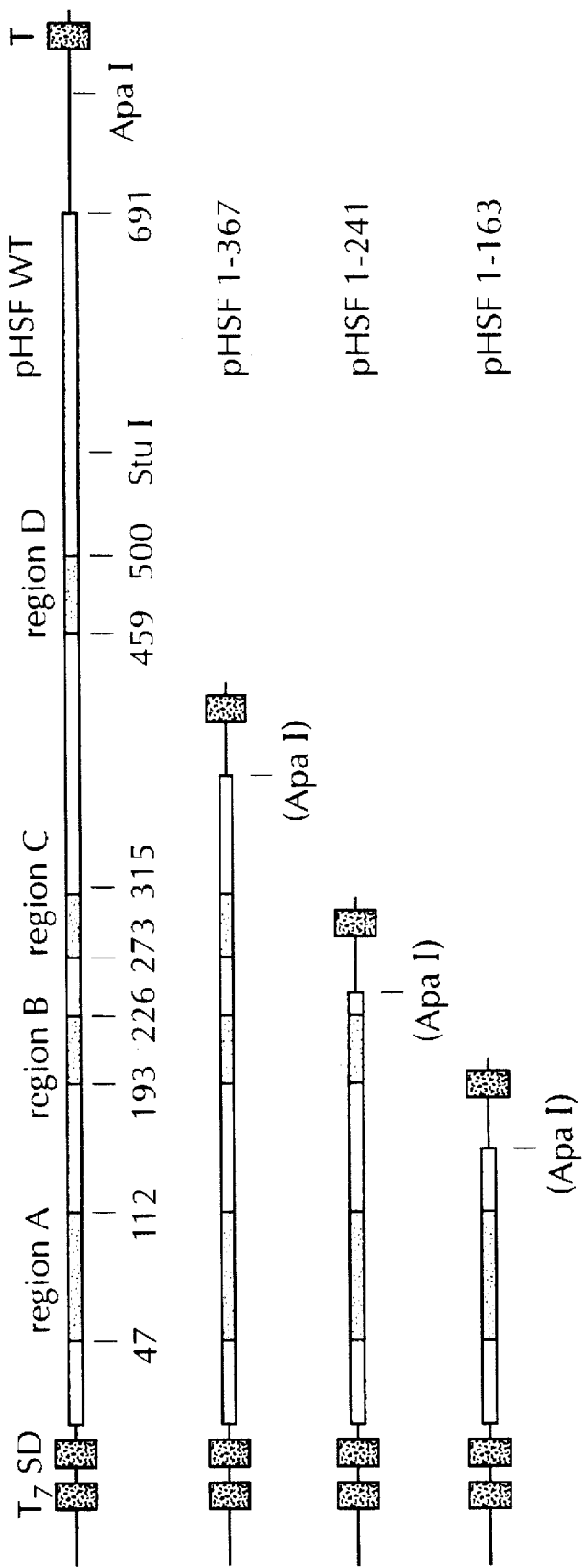
FIGS. 7A, 7B, and 7C represent the deletion analysis of HSF. (A) Schematic drawing of full-length HSF open reading frame (pHSF WT) and three deletion mutants PHSF 1-367, 1-241, and 1-163. All numbers refer to amino acid positions. The open bars represent HSF coding sequences; the shaded regions A–D represent sequences conserved between Drosophila and yeast HSF. The solid boxes indicate the φ10 promoter ($T_7$), the Shine-Delgarno (SD) sequence, and the transcription terminator (T) of the expression vector. (B) SDS polyacrylamide gel analysis of wild-type and mutant HSF polypeptides. Mutants were expressed in BL21 (DE3) in the presence of $^{35}$S-methionine (20 µCi/ml). 0.1 ml of culture was precipitated and the pellet was denatured at 100° C. in 10 µl of Laemmli sample buffer. Samples were electrophoresed on a 15% polyacrylamide gel and visualized by fluorography. The arrows pointing left indicate HSF polypeptides. A 26 kD protein (arrowhead) was also labeled in all samples, including *E. coli* transformed with the expression vector alone. (C) DNase I protection analysis of HSF mutants. A labeled fragment from the hsp70 promoter was incubated with the indicated amounts of wild-type or mutant HSF proteins. Footprinting reactions were performed essentially as described in FIG. 3C.
Figure 7B:
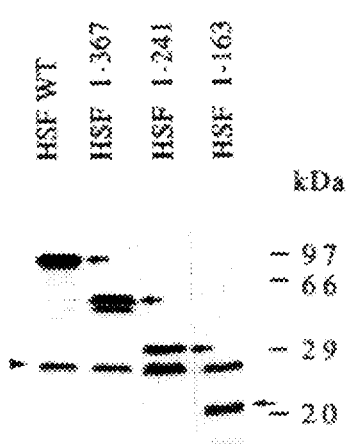
Figure 7C:
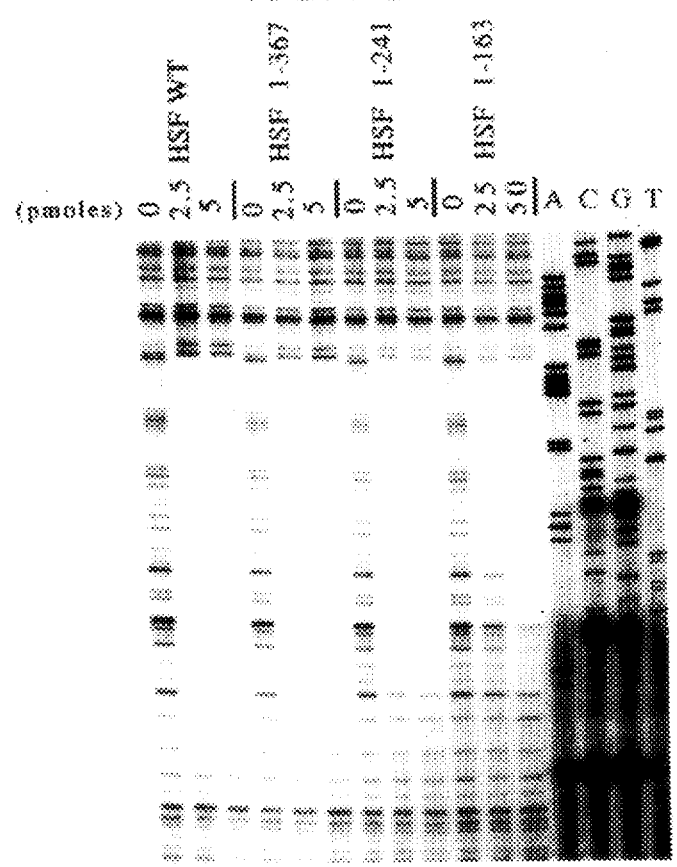

EXAMPLE 6
Drosophila HSF Regions Important for Specific and High Affinity Binding to DNA As a first step towards a molecular dissection of the structure of HSF protein, progressive 3'terminal portions of the HSF coding sequence were deleted (FIG. 7A), and the mutant genes were expressed in *E. coli* (Figure B). C-terminal truncations of HSF protein, up to residue 163 (HSF 1-163), are still capable of binding to DNA (FIG. 7B). However, HSF 1-163 shows a distinctly lower affinity for the hsp70 promoter compared to the affinity of full-length HSF. From the HSF protein concentrations required to achieve roughly 50% binding to DNA, it is estimated that HSF 1-163 binds with about 50-fold lower affinity relative to the binding of full-length HSF. The binding of HSF 1-241 and HSF 1-367 differ from full-length HSF by no more than 2-fold. These results show that HSF 1-163 is sufficient for binding specifically to HSEs; while an adjacent region, from residues 164 to 241, is important for high-affinity binding.

EXAMPLE 7
Conserved Sequences Between Drosoiphila and Yeast HSF

Figure 8A:
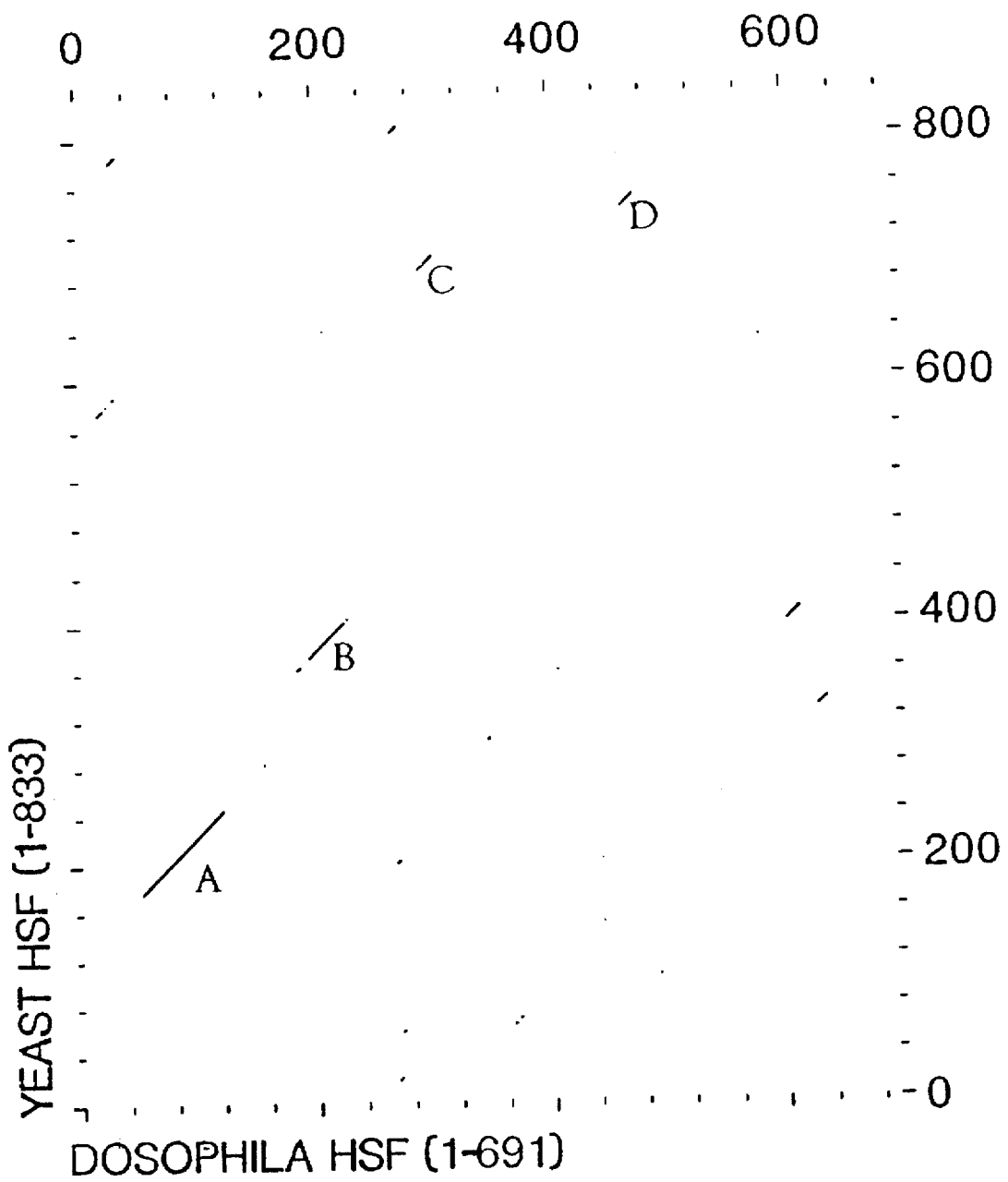

A comparison was made between the primary amino acid sequence of Drosophila HSF with the published sequence of yeast HSF (Wiederrecht (et al. 1988, *Cell,* 54, 841-853; Sorger and Pelham, 1988). It is striking that despite the high degree of homology among heat shock proteins between species as diverse as *E. coli* and Drosophila (about 50% identity, for hsp70; Bardwell and Craig, 1984, *Proc. Natl. Acad. Sci. U.S.A.,* 81, 848-852), the sequences of Drosophila and yeast HSF have diverged over a large portion of the proteins. A dot matrix plot of sequence similarities revealed two major and two minor regions of local conservation (FIG. 8A). Among the four regions, region A is most conserved between Drosophila and yeast HSF. Out of 66 amino acids, 33 are identical (50% identity; 73% similarity, allowing for conserved substitutions) (FIG. 8B).

Conserved region B shows 44% identity and 67% similarity in 33 amino acids. Region B is contained within a larger region of yeast HSF that is required for trimerization of the yeast factor (Sorger and Nelson, 1989, *Cell,* 59, 807-813). Regions C and D show 27% identity, 41% similarity, and 28% identity, 51% similarity, respectively. These regions are not involved with DNA recognition, since they can be deleted without affecting the DNA-binding function. Regions C and D are notably represented by polar amino acids, and among the 23 identical residues combined for both regions, 10 are serines or threonines, potential candidates for phosphorylation. Four of the identical residues are acidic.

Among the four regions conserved between Drosophila and yeast HSF, the 66 amino acid region A is most conserved (50% identity). This region is included within the DNA binding domains of both Drosophila and yeast HSF (this example and Wiederrecht et al, 1988, *Cell,* 54, 841-853), and may therefore organize a structural domain for specific DNA recognition. In *E. coli,* heat shock genes are positively regulated by a special sigma subunit of RNA polymerase, $\sigma^{32}$ (Gross et al, 1990, The function and regulation of heat shock proteins in *Escherichia coli.* In: Stress proteins in biology and medicine. Cold Spring Harbor Laboratory Press, 167-190.) The DNA binding domains of Drosophila HSF and yeast HSF with the $\sigma^{32}$ protein sequence were compared and a short conserved region was found which is also represented in the major *E. coli* sigma subunit, $\sigma^{70}$ (FIG. 9A). Intriguingly, many of the conserved amino acids are located in the putative DNA recognition helix of the sigma factors (Gribskov and Burgess, 1986, *Nucl. Acids Res.,* 14, 6745-6763; Helmann and Chamberlin, 1988, *Ann. Rev. Biochem.,* 57, 839-872). These results suggest that the homology to the putative recognition helix of sigma factors may define an element of the HSF DNA binding domain that is important for DNA binding.

EXAMPLE 8
Heptad Repeats of Hydrophobic Amino Acids

Two lines of evidence implicate sequences within and surrounding conserved region B in the self-association of Drosophila HSF. First, C-terminal deletions that remove 78 residues between amino acids 163 and 241 reduce the affinity for DNA, but not the specificity, by as much as 50-fold. Second, region B of yeast HSF has been shown directly to mediate trimerization of a truncated yeast HSF protein (Sorger and Nelson, 1989, *Cell,* 59, 807-813). These workers first noted an array of heptad repeats of hydrophobic residues in the yeast HSF oligomerization domain, and proposed a triple-stranded coiled-coil model for the yeast HSF trimer. A second, heptad array of hydrophobic residues located 18 amino acids C-terminal to the first array was suggested to contribute to the stability of the trimeric interface.

In this example, the first and second array of hydrophobic amino acid repeats in Drosophila HSF (FIG. 9B, large diamonds) were found. In addition, a third array of hydrophobic residues, positioned one residue out of register with the second array (FIG. 9B, small diamonds) was discovered. When the second and third array of heptad are viewed in a backbone model of an α-helix, it becomes evident that the helix has hydrophobic residues juxtaposed at four positions on one helical face. Such a helix would have the potential to associate with two neighboring helices of the same type by hydrophobic interactions characteristic of leucine zipper coiled-coils (Landschulz et al 1988, *Science,* 240, 1759-1764; O'Shea et al, 1989, *Science,* 245, 646-648). It is likely that these three assays of hybridization repeats direct assembly of the HSF hexamer.

The conserved amino acids in the oligomerization domain are not limited to hydrophobic residues. Identical residues include polar amino acids (three glutamines in a row [QQQ] ), hydrophobic [W,F,I,L], basic [R,K] and acidic [E] amino acids. Although hydrophobic interactions are the major stabilizing force between coiled-coils, additional specificity may be conferred by charged or polar interactions, mediated by residues outside the heptad repeat (Cohen and Parry, 1990, *Proteins,* 7, 1-15). The conserved residues may also be involved with interactions of the HSF subunit with other proteins (see example 9).

Figure 10A:
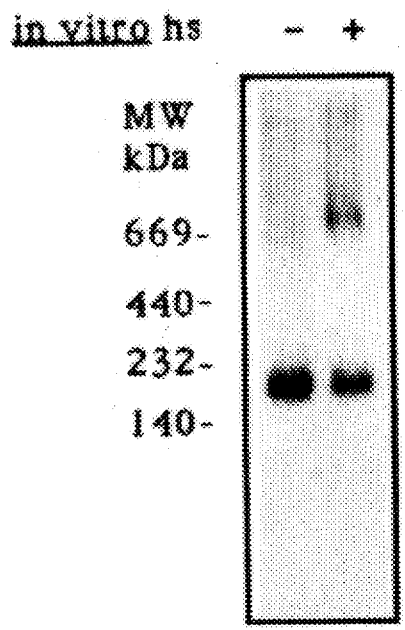
FIGS. 10A and 10B show a Western blot analysis of the molecular size of natural HSF present in cytoplasmic extracts of unshocked Drosophila cells. (A). Nondenaturing gel electrophoresis of cytoplasmic extracts prepared from Drosophila Schneider line-2 (SL-2) cells according to the method of Dignam (A. D. Dignam et al., Methods Enzymol. 1983 101, 582). 1.5 µl of nonshocked (0° C., [−]) or in vitro heat shocked (34° C. for 10 min. [+] cytoplasmic extract was diluted to 5 µl and subjected to non-denaturing gel electrophoresis followed by Western blotting. The position of high molecular weight protein standards (Pharmacia) run on the same gel are indicated. The membrane was processed for immunostaining with 1:1000 dilution of rabbit anti-Drosophila HSF polyclonal antibodies and 1:40,000 dilution of goat anti-rabbit antibody conjugated with alkaline phosphate, according to manufacturer's instructions (Tropix). A chemiluminescent substrate (Tropix) was employed to visualize the presence of secondary antibody. The membrane was wrapped in saran wrap and exposed to X-ray film. If the primary antiserum was omitted or pre-incubated with 1 µg/ml recombinant Drosophila HSF protein, the specific reaction with HSF was not observed. (B). SDS-PAGE of SL-2 cell cytoplasmic extracts, followed by Western blotting and immunostaining with anti-Drosophila HSF antibodies, as described above.
Figure 10B:
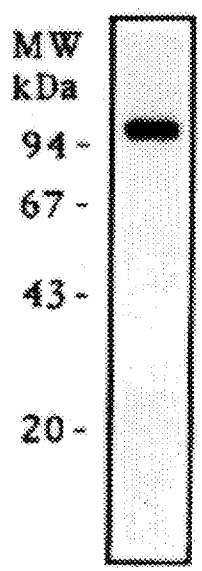
Figure 11:
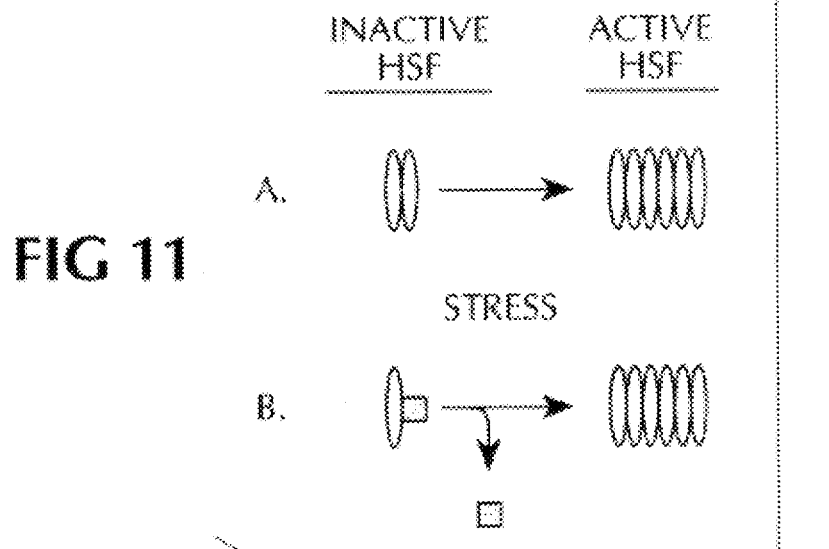
FIG. 11 represents a model for HSF regulation. Heat shock or stress conditions destabilize the inactive form of HSF symbolized by (A) a homodimer of HSF (oval) or (B) a heterodimer composed of HSF and an inhibiting protein (square), leading to the assembly of HSF hexamers, which binds to HSEs with high affinity and activates transcription of heatshock genes.

EXAMPLE 9
The Native Heat Shock Factor From Nonshocked Drosophila Cell Cytosol is a Homo- or Hetero-Dimer Using Western blots stained with Drosophila HSF-specific antibodies, the size c)f the inactive HSF present in nonshocked Drosophila cell cytosol was measured by pore exclusion limit electrophoresis on a nondenaturing polyacrylamide gradient gel. As shown in (FIG. 10A), the inactive form of Drosophila HSF migrates with a native size of approximately 220 kDa. In vitro activation of this HSF causes some of the 220 kDa species to be converted to 690 kDa, the native size of the active recombinant HSF protein from Drosophila. The specificity of the anti-HSF serum shown by the staining of the 110 kDa HSF subunit from crude Drosophila cell cytosol after SDS-PAGE and Western blot analysis (FIG. 10(B)). These results suggest that the native HSF protein increases from a dimeric state (2×110 kDa) to a hexameric state (6×110 kDa) upon heat stress activation. Alternatively, the inactive state of the HSF could be composed of a HSF monomer complexed to an inhibitor protein of similar size, and it is this HSF inhibitor complex which is disrupted upon heat stress, leading to the assembly of the active HSF hexamer (FIG. 11).

EXAMPLE 10
A Model for Heat Shock Regulation in Higher Eukaryotes

The naturally occurring form of HSF in Drosophila cells binds to DNA with high affinity only under stress conditions. Recombinant HSF synthesized in *E. coli* or in a rabbit reticulocyte lysate shows maximal affinity for DNA without a heat shock; this affinity is suppressed when HSF is synthesized in *Xenopus oocytes.* The results herein suggest that HSF protein has an intrinsic tendency to fold to the active conformation, which is suppressed in higher eukaryotic cells. Since the inactive HSF molecule appears to be dimeric, suppression of the intrinsic HSF activity therefore occurs by a block in the assembly of the HSF hexamer. This block in assembly could be due to the preferred association under normal conditions of HSF as a homodimer or a heterodimer composed of one subunit of HSF and an inhibiting molecule. (FIG. 11). The inactive HSF dimer is thus the target for the multiplicity of stress inducers, besides heat, which include drugs affecting energy metabolism, oxidizing agents, sulfhydryl reagents, chelating agents, heavy metals, ionophores, amino acid analogues, etc. (Ashburner and Bonner, 1979, Cell 17, 241–254; Nover, 1984, Biol. Zentr, 103, 357–435). Applicants and others cited herein have shown that the inactive state of HSF is easily altered in vitro by physical and chemical changes in environment. If the inactive HSF dimer is maintained in a metastable state by a diverse combination of molecular forces, for example, by hydrophobic, charged, and polar interactions, then the disruption of a subset of these forces by any one inducer of the stress response could be sufficient to trigger a charge of state, and lead to the formation of HSF hexamer.

EXAMPLE 11
Isolation of cDNA Clones for Human HSF (HuHSF)

Figure 12:
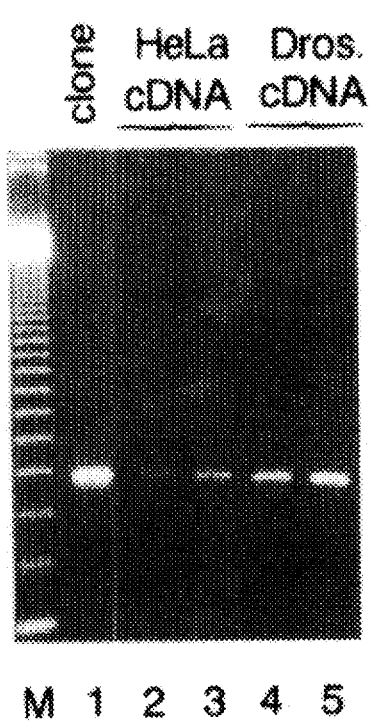
FIG. 12 shows the polymerase chain reaction using cDNA prepared from HeLa (lanes 2,3) and Drosophila (lanes 4,5) poly A+ RNA. Reaction products were analyzed on a 1% agarose gel and visualized by ethidium bromide staining. Lane 1 contains a control reaction using a Drosophila HSF control (Clos et al. 1990). The PCR reaction was carried out according to the manufacturer's instructions (Perkin Elmer Cetus). 2 µl (lanes 2,4) or 9 µl (lanes 3,5) of the cDNA reaction was used for PCR amplification in a final volume of 50 µl, with 0.5 µl (0.7 µg/µl) each of primer I: 5' GCCGGC [N]TT[C/T]CTGGCCAA[A/G]CT[N]TGG and primer ii: 5' CTGGAGCCA[N]AC[C/T]TC[A/G]TT[C/T]TC. The reaction was programmed for 1.5 minutes at 94° C., 2 minutes at 60° C., 3 minutes at 72° C. repeated 27 times with a change of the melting step to 1 minute at 94° C. for cycles 2 to 28 and the last extension step was for 6 minutes at 72° C. 20 µl of the reaction was applied to each gel lanes. The reverse transcription reaction contained in 50 µl: 5 µl 10× PCR reaction buffer, 20 µl 10 mM dNTP (each 2.5 mM), 2.5 µl of 0.2 µg/µl pdN$_6$, 1 µl (20 units) placental ribonuclease inhibitor, 1.25 µl MgCl$_2$, 2.5 µl Murine Leukemia Virus reverse transcriptase, and 5 µg (HeLa) or 2 µg (Drosophila) poly A+ RNA. The reaction was incubated at room temperature for 10 minutes and at 42° C. for 45 minutes. The reaction was terminated by heating to 95° C. for 5 minutes, diluted with 1 volume water and stored at −20° C. The PCR reaction with cloned Drosophila HSF (lane 1) contained 0.1 ng plasmid DNA. The marker lane contains 123 bp ladder (BRL).
Figure 14:
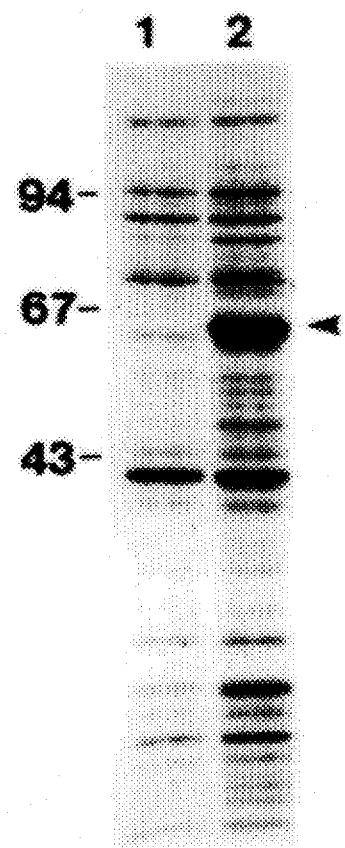
FIG. 14 shows expression of cloned human HSF in E. coli. The open reading frame of 529 amino acids was transferred to the expression vector pJC20 by introducing a site for the restriction endonuclease, NdeI, by site-directed mutagenesis at the initiating AUG codon. The plasmid was then restricted with NdeI and EcoRI and the fragment corresponding to the entire open reading frame was isolated from the gel and ligated into pJC20 previously restricted with the two enzymes. No extra amino acids are added to the expressed protein using this system. BL21(DE3) bacterial cells carrying the T7 polymerase gene under the control of a lac uv5 promoter were transformed with the plasmid. As a control, cells were transformed with the vector pJC20 alone. A single colony was picked from the plate and cells were grown in LB broth containing 0.4% glucose and 200 µg/ml ampicillin to an OD600 of 0.5. Isopropyl-β-D thiogalactoside (IPTG) was added to a concentration of 0.4 mM and incubation continued at 37° C. for 3 hours. Cells were harvested by centrifugation and resuspended in HEMGN (25 mM HEPES, pH 7.9, 0.1 mM EDTA, 12.5 mM MgCl$_2$, 10% glycerol, 0.1% NP-40, 1 mM DTT) containing 300 mM KCl. The cells were disrupted by sonication using 6 pulses of 20 seconds each at 25 to 30 W power. Cells were placed in ice-water for 30 seconds between pulses. Extracts were clarified by centrifugation at 10,000 g for 10 minutes and flash-frozen in liquid nitrogen.

Heat shock transcriptional activation, heat shock factor has been cloned from human. The cloning of human heat shock factor (HuHSF) was achieved by using short stretches of homologous sequences between Drosophila and yeast heat shock factors as primers in the polymerase chain reaction (PCR). (FIG. 12). The human HSF length clone was obtained by screening human cDNA libraries with the amplified sequence. The HuHSF cDNA clone includes an open reading frame of 529 amino acids with a calculated molecular weight of 58,000. (FIG. 13). The size of HuHSF as measured by SDS-polyacrylamide gel electrophoresis is 60,000 which is in close agreement with the calculated size. (FIG. 34).

EXAMPLE 12
Expression of Recombination Human HSF in E. coli

Figures 2, 15B:
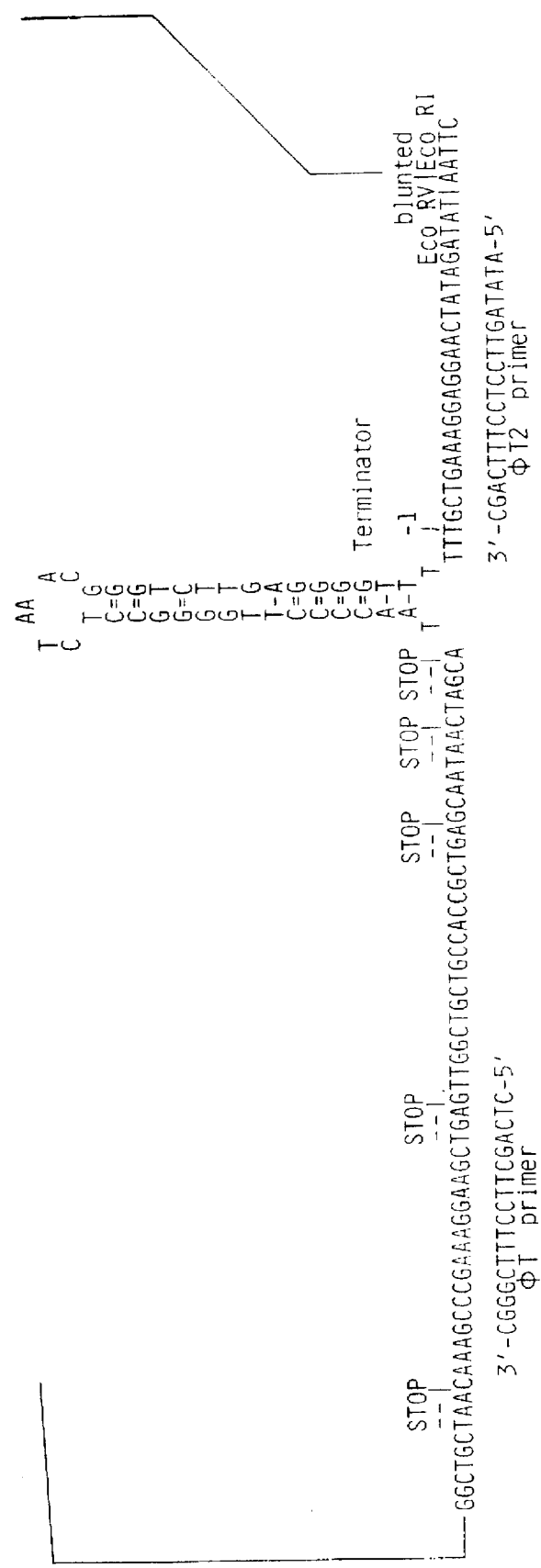

The open reading frame of 529 amino acids was inserted into the expression vector pJC20 by introducing a site for the restriction endonuclease, NdeI, by site-directed mutagenesis at the initiating AUG codon. The plasmid was then restricted with NdeI and ECoRI and the fragment corresponding to the entire open reading frame was isolated from the gel and ligated into pJC20 previously restricted with the two enzymes (FIG. 15). No extra amino acids are added to the expressed protein using this system. BL21(DE3) cells carrying the T7 polymerase gene under the control of a lac uv5 promoter were transformed with the plasmid. As a control, cells were transformed with the vector pJC20 alone. A single colony was picked from the plate and cells were grown in LB broth containing 0.4% glucose and 20 µg/ml ampicillin to an OD600 of 0.5. IsopropylB-D thiogalactoside (IPTG) was added to a concentration of 0.4 mM and incubation continued at 37° C. for 3 hours. Cells were harvested by centrifugation and resuspended in HEMGN (25 mM HEPES, pH 7.9, 0.1 mM EDTA, 12.5 mM $MgCl_2$, 10% glycerol, 0.1% NP-40, 1 mM DTT) containing 300 mM KCl. The cells were disrupted by sonication using 6 pulses of 20 seconds each at 25 to 30 W power. Cells were placed in ice-water for 30 seconds between pulses. Extracts were clarified by centrifugation at 10,000 g for 10 minutes and flash-frozen in liquid nitrogen. Extract proteins were analyzed by SDS-PAGE and stained with Coomassie Blue.

EXAMPLE 13
DNA Binding Transcription Factor Activity by Recombinant Human HSF in the Absence of Heat Shock HUHSF expressed in E. coli under non-shock conditions was shown to be capable of binding specifically to the heat shock regulatory elements in vitro as determined by the gel mobility shift assay (FIG. 16) and by nuclease protection experiments (FIG. 17) essentially as described for the Drosophila HSF protein in Example 3.

EXAMPLE 14
Transcriptional Activity of Recombinant HUHSF

The ability of the cloned human HSF protein to function as a transcription factor in vitro was demonstrated using a heat shock plasmid template and a cell-free transcription system derived from Drosophila embryos, essentially as described in Example 4 for the recombinant Drosophila HSF protein. In this example, addition of extracts from E. coli expressing cloned human HSF to the assay caused a ~6-fold stimulation of transcription in vitro (FIG. 18). This increase, similar to that observed with cloned Drosophila HSF protein, is dependent on protein binding to HSEs, since no stimulation was observed on a template with the HSEs deleted. The ability of the 529 amino acid ORF encoding human HSF to function as a HSE-dependent transcription factor indicates that this ORF encodes most or all of a human HISF protein.

For purposes of completing this disclosure, all documents cited herein are hereby incorporated by reference.

While the foregoing invention has been described in some detail for purposes of clarity and understanding, it will be appreciated by one skilled in the art from a reading of this disclosure that various changes in form and detail can be made without departing from the true scope of the invention.

---

SEQUENCE LISTING ( 1 ) GENERAL INFORMATION:

( i i i ) NUMBER OF SEQUENCES: 42

( 2 ) INFORMATION FOR SEQ ID NO:1:

( i ) SEQUENCE CHARACTERISTICS:
        ( A ) LENGTH: 54
        ( B ) TYPE: nucleic acid
        ( C ) STRANDEDNESS: single
        ( D ) TOPOLOGY: linear ( i i ) MOLECULE TYPE: oligonucleotide ( x i ) SEQUENCE DESCRIPTION: SEQ ID NO:1:

GATGTTCTCA AGGAGCTGCT CCTGGCCACG CAGGAAGCAT     40

```
GGTGCTGGAA CTCC                                                            5 4
```

( 2 ) INFORMATION FOR SEQ ID NO:2:

( i ) SEQUENCE CHARACTERISTICS:
    ( A ) LENGTH: 691
    ( B ) TYPE: amino acid
    ( C ) STRANDEDNESS: unknown
    ( D ) TOPOLOGY: unknown ( i i ) MOLECULE TYPE: protein ( x i ) SEQUENCE DESCRIPTION: SEQ ID NO:2:

```
Met Ser Arg Ser Arg Ser Ser Ala Lys Ala Val Gln
1               5                   10

Phe Lys His Glu Ser Glu Glu Glu Glu Asp Glu
        15                  20

Glu Glu Gln Leu Pro Ser Arg Arg Met His Ser Tyr
25                  30                  35

Gly Asp Ala Ala Ala Ile Gly Ser Gly Val Pro Ala
            40                  45

Phe Leu Ala Lys Leu Trp Arg Leu Val Asp Asp Ala
    50                  55                  60

Asp Thr Asn Arg Leu Ile Cys Trp Thr Lys Asp Gly
                65                  70

Gln Ser Phe Val Ile Gln Asn Gln Ala Gln Phe Ala
        75                  80

Lys Glu Leu Leu Pro Leu Asn Tyr Lys His Asn Asn
85                  90                  95

Met Ala Ser Phe Ile Arg Gln Leu Asn Met Tyr Gly
            100                 105

Phe His Lys Ile Thr Ser Ile Asp Asn Gly Gly Leu
    110                 115                 120

Arg Phe Asp Arg Asp Glu Ile Glu Phe Ser His Pro
                125                 130

Phe Phe Lys Arg Asn Ser Pro Phe Leu Leu Asp Gln
        135                 140

Ile Lys Arg Lys Ile Ser Asn Asn Lys Asn Gly Asp
145                 150                 155

Asp Lys Gly Val Leu Lys Pro Glu Ala Met Ser Lys
            160                 165

Ile Leu Thr Asp Val Lys Val Met Arg Gly Arg Gln
    170                 175                 180

Asp Asn Leu Asp Ser Arg Phe Ser Ala Met Lys Gln
                185                 190

Glu Asn Glu Val Leu Trp Arg Glu Ile Ala Ser Leu
        195                 200

Arg Gln Lys His Ala Lys Gln Gln Gln Ile Val Asn
205                 210                 215

Lys Leu Ile Gln Phe Leu Ile Thr Ile Val Gln Pro
            220                 225

Ser Arg Asn Met Ser Gly Val Lys Arg His Val Gln
    230                 235                 240

Leu Met Ile Asn Asn Thr Pro Glu Ile Asp Arg Ala
                245                 250

Arg Thr Thr Ser Glu Thr Glu Ser Glu Ser Gly Gly
        255                 260
```

```
Gly  Pro  Val  Ile  His  Glu  Leu  Arg  Glu  Leu  Leu
265                 270                 275

Asp  Glu  Val  Met  Asn  Pro  Ser  Pro  Ala  Gly  Tyr  Thr
               280                 285

Ala  Ala  Ser  His  Tyr  Asp  Gln  Glu  Ser  Val  Ser  Pro
          290            295                           300

Pro  Ala  Val  Glu  Arg  Pro  Arg  Ser  Asn  Met  Ser  Ile
                    305                      310

Ser  Ser  His  Asn  Val  Asp  Tyr  Ser  Asn  Gln  Ser  Val
          315                 320

Glu  Asp  Leu  Leu  Leu  Gln  Gly  Asn  Gly  Thr  Ala  Gly
325                      330                      335

Gly  Asn  Ile  Leu  Val  Gly  Gly  Ala  Ala  Ser  Pro  Met
               340                      345

Ala  Gln  Ser  Val  Ser  Gln  Ser  Pro  Ala  Gln  His  Asp
          350                 355                      360

Val  Tyr  Thr  Val  Thr  Glu  Ala  Pro  Asp  Ser  His  Val
                    365                      370

Gln  Glu  Val  Pro  Asn  Ser  Pro  Pro  Tyr  Tyr  Glu  Glu
          375                      380

Gln  Asn  Val  Leu  Thr  Thr  Pro  Met  Val  Arg  Glu  Gln
385                      390                      395

Glu  Gln  Gln  Lys  Arg  Gln  Gln  Leu  Lys  Glu  Asn  Asn
               400                 405

Lys  Leu  Arg  Arg  Gln  Ala  Gly  Asp  Val  Ile  Leu  Asp
     410                 415                           420

Ala  Gly  Asp  Ile  Leu  Val  Asp  Ser  Ser  Ser  Pro  Lys
               425                      430

Ala  Gln  Arg  Thr  Ser  Ile  Gln  His  Ser  Thr  Gln  Pro
          435                 440

Asp  Val  Met  Val  Gln  Pro  Met  Ile  Ile  Lys  Ser  Glu
445                      450                 455

Pro  Glu  Asn  Ser  Ser  Gly  Leu  Met  Asp  Leu  Met  Thr
               460                 465

Pro  Ala  Asn  Asp  Leu  Tyr  Ser  Val  Asn  Phe  Ile  Ser
     470                      475                      480

Glu  Asp  Met  Pro  Thr  Asp  Ile  Phe  Glu  Asp  Ala  Leu
               485                      490

Leu  Pro  Asp  Gly  Val  Glu  Glu  Ala  Ala  Lys  Leu  Asp
          495                 500

Gln  Gln  Gln  Lys  Phe  Gly  Gln  Ser  Thr  Val  Ser  Ser
505                      510                      515

Gly  Lys  Phe  Ala  Ser  Asn  Phe  Asp  Val  Pro  Thr  Asn
               520                 525

Ser  Thr  Leu  Leu  Asp  Ala  Asn  Gln  Ala  Ser  Thr  Ser
     530                      535                      540

Lys  Ala  Ala  Ala  Lys  Ala  Gln  Ala  Ser  Glu  Glu  Glu
               545                      550

Gly  Met  Ala  Val  Ala  Lys  Tyr  Ser  Gly  Ala  Glu  Asn
          555                 560

Gly  Asn  Asn  Arg  Asp  Thr  Asn  Asn  Ser  Gln  Leu  Leu
565                      570                      575

Arg  Met  Ala  Ser  Val  Asp  Glu  Leu  His  Gly  His  Leu
```

|     | 580 |     |     |     |     | 585 |     |     |     |
| --- | --- | --- | --- | --- | --- | --- | --- | --- | --- |
| Glu | Ser | Met | Gln | Asp | Glu | Leu | Glu | Thr | Leu | Lys | Asp |
| 590 |     |     |     |     |     | 595 |     |     |     |     | 600 |

Leu Leu Arg Gly Asp Gly Val Ala Ile Asp Gln Asn
                605              610

Met Leu Met Gly Leu Phe Asn Asp Ser Asp Leu Met
        615                  620

Asp Asn Tyr Gly Leu Ser Phe Pro Asn Asp Ser Ile
625                 630                  635

Ser Ser Glu Lys Lys Ala Pro Ser Gly Ser Glu Leu
            640                  645

Ile Ser Tyr Gln Pro Met Tyr Asp Leu Ser Asp Ile
    650                  655                  660

Leu Asp Thr Asp Asp Gly Asn Asn Asp Gln Glu Ala
            665                  670

Ser Arg Arg Gln Met Gln Thr Gln Ser Ser Val Leu
        675                  680

Asn Thr Pro Arg His Glu Leu
685                 690

( 2 ) INFORMATION FOR SEQ ID NO:3:

( i ) SEQUENCE CHARACTERISTICS:
        ( A ) LENGTH: 204
        ( B ) TYPE: nucleic acid
        ( C ) STRANDEDNESS: double
        ( D ) TOPOLOGY: linear ( i i ) MOLECULE TYPE: genomic DNA ( x i ) SEQUENCE DESCRIPTION: SEQ ID NO:3:

| | | | | |
|---|---|---|---|---|
| CTCGAGGTCT | CGAGAAATTT | CTCTGGCCGT | TATTCTCTAT | 40 |
| TCGTTTTGTG | ACTCTCCCTC | TCTGTACTAT | TGCTCTCTCA | 80 |
| CTCTGTCGCA | CAGTAAACGG | CACACTGTTC | TCGTTGCTTC | 120 |
| GAGAGAGCGC | GCCTCGAATG | TTCGCGAAAA | GAGCGCCGGA | 160 |
| GTATAAATAG | AGGCGCTTCG | TCGACGGAGC | GTCAATTCAA | 200 |
| TTCA | | | | 204 |

( 2 ) INFORMATION FOR SEQ ID NO:4:

( i ) SEQUENCE CHARACTERISTICS:
        ( A ) LENGTH: 50
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

Gly Val Pro Ala Phe Leu Ala Lys Leu Trp Arg Leu
1               5                   10

Val Asp Asp Ala Asp Thr Asn Arg Leu Ile Cys Trp
        15                  20

Thr Lys Asp Gly Gln Ser Phe Val Ile Gln Asn Gln
25                  30                  35

Ala Gln Phe Ala Lys Glu Leu Leu Pro Leu Asn Tyr
            40                  45

Lys His ( 2 ) INFORMATION FOR SEQ ID NO:5:

( i ) SEQUENCE CHARACTERISTICS:
    ( A ) LENGTH: 50
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:5:

```
Ser  Arg  Pro  Ala  Phe  Val  Asn  Lys  Leu  Trp  Ser  Met
1                   5                        10

Leu  Asn  Asp  Asp  Ser  Asn  Thr  Lys  Leu  Ile  Gln  Trp
               15                  20

Ala  Glu  Asp  Gly  Lys  Ser  Phe  Ile  Val  Thr  Asn  Arg
25                       30                       35

Glu  Glu  Phe  Val  His  Gln  Ile  Leu  Pro  Lys  Tyr  Phe
                40                 45

Lys  His
     50
```

( 2 ) INFORMATION FOR SEQ ID NO:6:

( i ) SEQUENCE CHARACTERISTICS:
    ( A ) LENGTH: 49
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:6:

```
Asn  Asn  Met  Ala  Ser  Phe  Ile  Arg  Gln  Leu  Asn  Met
1                   5                        10

Tyr  Gly  Phe  His  Lys  Ile  Thr  Ser  Ile  Asp  Asn  Gly
               15                  20

Gly  Leu  Arg  Phe  Asp  Arg  Asp  Glu  Ile  Glu  Phe  Ser
25                       30                       35

His  Pro  Phe  Phe  Lys  Arg  Asn  Ser  Pro  Phe  Leu  Leu  Asp
                40                 45
```

( 2 ) INFORMATION FOR SEQ ID NO:7:

( i ) SEQUENCE CHARACTERISTICS:
    ( A ) LENGTH: 25
    ( B ) TYPE: nucleic acid
    ( C ) STRANDEDNESS: single
    ( D ) TOPOLOGY: linear ( i i ) MOLECULE TYPE: oligonucleotide ( i x ) FEATURE:
    ( D ) OTHER INFORMATION: N is either C or T ( x i ) SEQUENCE DESCRIPTION: SEQ ID NO:7:

AAGCACAACA ACATGGCCAG NTTCA    25

( 2 ) INFORMATION FOR SEQ ID NO:8:

( i ) SEQUENCE CHARACTERISTICS:
    ( A ) LENGTH: 5
    ( B ) TYPE: amino acid
    ( C ) STRANDEDNESS: single (D) TOPOLOGY: linear (ii) MOLECULE TYPE: peptide (xi) SEQUENCE DESCRIPTION: SEQ ID NO:8:

Ala Val Gln Phe Lys
1               5

(2) INFORMATION FOR SEQ ID NO:9:

(i) SEQUENCE CHARACTERISTICS:
              (A) LENGTH: 14
              (B) TYPE: amino acid
              (C) STRANDEDNESS: single
              (D) TOPOLOGY: linear (ii) MOLECULE TYPE: peptide (xi) SEQUENCE DESCRIPTION: SEQ ID NO:9:

Asp Gly Gln Ser Met Phe Val Ile Gln Asn Ala Gln
1               5                   10

Phe Ala (2) INFORMATION FOR SEQ ID NO:10:

(i) SEQUENCE CHARACTERISTICS:
              (A) LENGTH: 14
              (B) TYPE: amino acid
              (C) STRANDEDNESS: single
              (D) TOPOLOGY: linear (ii) MOLECULE TYPE: peptide (xi) SEQUENCE DESCRIPTION: SEQ ID NO:10:

Lys Val Gln Leu Met Ile Asn Asn Thr Pro Glu Ile
1               5                   10

Asp Arg (2) INFORMATION FOR SEQ ID NO:11:

(i) SEQUENCE CHARACTERISTICS:
              (A) LENGTH: 11
              (B) TYPE: amino acid
              (C) STRANDEDNESS: single
              (D) TOPOLOGY: linear (ii) MOLECULE TYPE: peptide (xi) SEQUENCE DESCRIPTION: SEQ ID NO:11:

Phe Ser Ala Met Lys Gln Glu Asn Glu Val Leu
1               5                   10

(2) INFORMATION FOR SEQ ID NO:12:

(i) SEQUENCE CHARACTERISTICS:
              (A) LENGTH: 19
              (B) TYPE: amino acid
              (C) STRANDEDNESS: single
              (D) TOPOLOGY: linear (ii) MOLECULE TYPE: peptide (xi) SEQUENCE DESCRIPTION: SEQ ID NO:12:

Phe Ala Xaa Asn Phe Asp Val Pro Thr Asn Ser Xaa
1               5                   10

Leu Leu Asp Ala Asn Gln Ala
            15

(2) INFORMATION FOR SEQ ID NO:13:

(i) SEQUENCE CHARACTERISTICS:
        (A) LENGTH: 8
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:13:

```
Ile Thr Ser Ile Asp Asn Gly Gly
 1               5
```

(2) INFORMATION FOR SEQ ID NO:14:

(i) SEQUENCE CHARACTERISTICS:
        (A) LENGTH: 50
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:14:

```
Ser Asn Phe Ala Ser Phe Val Arg Gln Leu Asn Met
 1               5                          10
Tyr Gly Trp His Lys Val Gln Asp Val Lys Ser Gly
                15               20
Ser Ile Gln Ser Ser Ser Asp Asp Lys Trp Gln Phe
25               30                          35
Glu Asn Glu Asn Phe Ile Arg Gly Arg Glu Asp Leu
                40               45
Leu Glu
50
```

(2) INFORMATION FOR SEQ ID NO:15:

(i) SEQUENCE CHARACTERISTICS:
        (A) LENGTH: 26
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

```
Gln Ile Lys Arg Lys Ile Ser Asn Asn Lys Asn Gly
 1               5                          10
Asp Asp Lys Gly Val Leu Lys Pro Glu Ala Met Ser
                15               20
Lys Ile
25
```

(2) INFORMATION FOR SEQ ID NO:16:

(i) SEQUENCE CHARACTERISTICS:
        (A) LENGTH: 50
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

```
Lys Ile Ile Arg Gln Lys Gly Ser Ser Asn Asn His
```

```
  1                    5                        10
Asn  Ser  Pro  Ser  Gly  Asn  Gly  Asn  Pro  Ala  Asn  Gly
               15                    20

Ser  Asn  Ile  Pro  Leu  Asp  Asn  Ala  Ala  Gly  Ser  Asn
25                       30                          35

Asn  Ser  Asn  Asn  Asn  Ile  Ser  Ser  Ser  Asn  Ser  Phe
                40                       45

Phe  Asn
     50
```

( 2 ) INFORMATION FOR SEQ ID NO:17:

( i ) SEQUENCE CHARACTERISTICS:
        ( A ) LENGTH: 23
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:17:

```
Leu  Thr  Asp  Val  Lys  Val  Met  Arg  Gly  Arg  Gln  Asp
1                    5                        10

Asn  Leu  Asp  Ser  Arg  Phe  Ser  Ala  Met  Lys  Gln
               15                    20
```

( 2 ) INFORMATION FOR SEQ ID NO:18:

( i ) SEQUENCE CHARACTERISTICS:
        ( A ) LENGTH: 50
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:18:

```
His  Gly  His  Leu  Leu  Gln  Gly  Lys  Thr  Leu  Arg  Leu
1                    5                        10

Met  Asn  Glu  Ala  Asn  Leu  Gly  Asp  Lys  Asn  Asp  Val
               15                    20

Thr  Ala  Ile  Leu  Gly  Glu  Leu  Glu  Gln  Ile  Lys  Tyr
25                       30                          35

Asn  Gln  Leu  Ala  Ile  Ser  Lys  Asp  Leu  Leu  Arg  Ile
                40                       45

Asn  Lys
     50
```

( 2 ) INFORMATION FOR SEQ ID NO:19:

( i ) SEQUENCE CHARACTERISTICS:
        ( A ) LENGTH: 43
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:19:

```
Glu  Asn  Glu  Val  Leu  Trp  Arg  Glu  Ile  Ala  Ser  Leu
1                    5                        10

Arg  Gln  Lys  His  Ala  Lys  Gln  Gln  Ile  Val  Asn
               15                    20
```

```
Lys  Leu  Ile  Gln  Phe  Leu  Ile  Thr  Ile  Val  Gln  Pro
 25                      30                      35

Ser  Arg  Asn  Met  Ser  Gly  Val
                 40
```

( 2 ) INFORMATION FOR SEQ ID NO:20:

( i ) SEQUENCE CHARACTERISTICS:
        ( A ) LENGTH: 46
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:20:

```
Asp  Asn  Glu  Leu  Leu  Trp  Gln  Glu  Asn  Met  Met  Ala
 1                    5                      10

Arg  Glu  Arg  His  Arg  Thr  Gln  Gln  Gln  Ala  Leu  Glu
          15                      20

Lys  Met  Phe  Arg  Phe  Leu  Thr  Ser  Ile  Val  Pro  His
 25                      30                      35

Leu  Asp  Pro  Lys  Met  Ile  Met  Asp  Gly  Leu
                 40                      45
```

( 2 ) INFORMATION FOR SEQ ID NO:21:

( i ) SEQUENCE CHARACTERISTICS:
        ( A ) LENGTH: 43
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:21:

```
Glu  Glu  Leu  Leu  Asp  Glu  Val  Met  Asn  Pro  Ser  Pro
 1                    5                      10

Ala  Gly  Tyr  Thr  Ala  Ala  Ser  His  Tyr  Asp  Gln  Glu
          15                      20

Ser  Val  Ser  Pro  Pro  Ala  Val  Glu  Arg  Pro  Arg  Ser
 25                      30                      35

Asn  Met  Ser  Ile  Ser  Ser  His
                 40
```

( 2 ) INFORMATION FOR SEQ ID NO:22:

( i ) SEQUENCE CHARACTERISTICS:
        ( A ) LENGTH: 43
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:22:

```
Asn  Ser  Asn  Met  Glu  Ser  Ala  Val  Asn  Val  Asn  Ser
 1                    5                      10

Pro  Gly  Phe  Asn  Leu  Gln  Asp  Tyr  Leu  Thr  Gly  Glu
          15                      20

Ser  Asn  Ser  Pro  Asn  Ser  Val  His  Ser  Val  Pro  Ser
 25                      30                      35

Asn  Gly  Ser  Gly  Ser  Thr  Pro
                 40
```

( 2 ) INFORMATION FOR SEQ ID NO:23:

( i ) SEQUENCE CHARACTERISTICS:
        ( A ) LENGTH: 50
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:23:

```
Glu Pro Glu Asn Ser Ser Gly Leu Met Asp Leu Met
1               5                   10
Thr Pro Ala Asn Asp Leu Tyr Ser Val Asn Glu Ile
            15                  20
Ser Glu Asp Met Pro Thr Asp Ile Phe Glu Asp Ala
25                  30                      35
Leu Leu Pro Asp Gly Val Glu Glu Ala Ala Lys Leu
            40                  45
Asp Gln
    50
```

( 2 ) INFORMATION FOR SEQ ID NO:24:

( i ) SEQUENCE CHARACTERISTICS:
        ( A ) LENGTH: 47
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:24:

```
Gln Gly Glu Asn Gly Ser Gly Leu Thr Pro Phe Leu
1               5                   10
Thr Val Asp Asp His Thr Leu Asn Asp Asn Thr
            15                  20
Ser Glu Gly Ser Thr Arg Val Ser Pro Asp Ile Lys
25                  30                      35
Phe Ser Ala Ser Glu Asn Thr Lys Val Ser Asp
            40                  45
```

( 2 ) INFORMATION FOR SEQ ID NO:25:

( i ) SEQUENCE CHARACTERISTICS:
        ( A ) LENGTH: 34
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:25:

```
Leu Leu Pro Leu Asn Tyr Lys His Asn Asn Met Ala
1               5                   10
Ser Phe Ile Arg Gln Leu Asn Met Tyr Gly Phe His
            15                  20
Lys Ile Thr Ser Ile Asp Asn Gly Gly Leu
25                  30
```

( 2 ) INFORMATION FOR SEQ ID NO:26:

( i ) SEQUENCE CHARACTERISTICS:

(A) LENGTH: 34
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:26:

```
Ile Leu Pro Lys Tyr Phe Lys His Ser Asn Phe Ala
1               5                   10
Ser Phe Val Arg Gln Leu Asn Met Tyr Gly Trp His
            15                  20
Lys Val Gln Asp Val Lys Ser Gly Ser Ile
25                  30
```

(2) INFORMATION FOR SEQ ID NO:27:

(i) SEQUENCE CHARACTERISTICS:
(A) LENGTH: 32
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:27:

```
Leu Gln Glu Leu Ala Asp Arg Tyr Gly Val Ser Ala
1               5                   10
Glu Arg Val Arg Gln Leu Glu Lys Asn Ala Met Lys
            15                  20
Lys Leu Arg Ala Ala Ile Glu Ala
25                  30
```

(2) INFORMATION FOR SEQ ID NO:28:

(i) SEQUENCE CHARACTERISTICS:
(A) LENGTH: 34
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:28:

```
Leu Glu Glu Val Gly Lys Gln Phe Asp Val Thr Arg
1               5                   10
Glu Arg Ile Arg Gln Ile Glu Ala Lys Ala Leu Arg
            15                  20
Lys Leu Arg His Pro Ser Arg Ser Glu Val
25                  30
```

(2) INFORMATION FOR SEQ ID NO:29:

(i) SEQUENCE CHARACTERISTICS:
(A) LENGTH: 77
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:29:

```
Met Ser Lys Ile Leu Thr Asp Val Lys Val Met Arg
1               5                   10
Gly Arg Gln Asp Asn Leu Asp Ser Arg Phe Ser Ala
            15                  20
```

Met Lys Gln Glu Asn Glu Val Leu Trp Arg Glu Ile
25                  30                  35

Ala Ser Leu Arg Gln Lys His Ala Lys Gln Gln Gln
            40              45

Ile Val Asn Lys Leu Ile Gln Phe Leu Ile Thr Ile
        50              55                  60

Val Gln Pro Ser Arg Asn Met Ser Gly Val Lys Arg
                65              70

His Val Gln Leu Met
        75

( 2 ) INFORMATION FOR SEQ ID NO:30:

( i ) SEQUENCE CHARACTERISTICS:
　　　　( A ) LENGTH: 77
　　　　( B ) TYPE: amino acid
　　　　( C ) STRANDEDNESS: single
　　　　( D ) TOPOLOGY: linear ( i i ) MOLECULE TYPE: peptide ( x i ) SEQUENCE DESCRIPTION: SEQ ID NO:30:

Val Thr Ala Ile Leu Gly Glu Leu Glu Gln Ile Lys
1               5                   10

Tyr Asn Gln Leu Ala Ile Ser Lys Asp Leu Leu Arg
            15              20

Ile Asn Lys Asp Asn Glu Leu Leu Trp Gln Glu Asn
25                  30                  35

Met Met Ala Arg Glu Arg His Arg Thr Gln Gln Gln
            40              45

Ala Leu Glu Lys Met Phe Arg Phe Leu Thr Ser Ile
    50              55                  60

Val Pro His Leu Asp Pro Lys Met Ile Met Asp Gly
                65              70

Leu Gly Asp Pro Lys
        75

( 2 ) INFORMATION FOR SEQ ID NO:31:

( i ) SEQUENCE CHARACTERISTICS:
　　　　( A ) LENGTH: 2156
　　　　( B ) TYPE: nucleic acid
　　　　( C ) STRANDEDNESS: double
　　　　( D ) TOPOLOGY: linear ( i i ) MOLECULE TYPE: (DNA) genomic ( x i ) SEQUENCE DESCRIPTION: SEQ ID NO:31:

| | | | | |
|---|---|---|---|---|
| CGGGCCCGTT | GCAAGATGGC | GGCGGCCATG | CTGGGCCCCG | 40 |
| GGGCTGTGTG | TGCGCAGCGG | GCGGCGGCGC | GGCCCGGAAG | 80 |
| GCTGGCGCGG | CGACGGCGTT | AGCCCGGCCC | TCGGCCCCTC | 120 |
| TTTGCGGCCG | CTCCCTCCGC | CTATTCCCTC | CTTGCTCGAG | 160 |
| ATGGATCTGC | CCGTGGGCCC | CGGCGCGGCG | GGGCCCAGCA | 200 |
| ACGTCCCGGC | CTTCCTGACC | AAGCTGTGGA | CCCTCGTGAG | 240 |
| CGACCCGGAC | ACCGACGCGC | TCATCTGCTG | GAGCCCGAGC | 280 |
| GGGAACAGCT | TCCACGTGTT | CGACCAGGGC | CAGTTTGCCA | 320 |
| AGGAGGTGCT | GCCCAAGTAC | TTCAAGCACA | ACAACATGGC | 360 |

-continued

| | | | | |
|---|---|---|---|---|
| CAGCTTCGTG | CGGCAGCTCA | ACATGTATGG | CTTCCGGAAA | 400 |
| GTGGTCCACA | TCGAGCAGGG | CGGCCTGGTC | AAGCCAGAGA | 440 |
| GAGACGACAC | GGAGTTCCAG | CACCCATGCT | TCCTGCGTGG | 480 |
| CCAGGAGCAG | CTCCTTGAGA | ACATCAAGAG | GAAAGTGACC | 520 |
| AGTGTGTCCA | CCCTGAAGAG | TGAAGACATA | AAGATCCGCC | 560 |
| AGGACAGCGT | CACCAAGCTG | CTGACGGACG | TGCAGCTGAT | 600 |
| GAAGGGGAAG | CAGGAGTGCA | TGGACTCCAA | GCTCCTGGCC | 640 |
| ATGAAGCATG | AGAATGAGGC | TCTGTGGCGG | GAGGTGGCCA | 680 |
| GCCTTCGGCA | GAAGCATGCC | CAGCAACAGA | AAGTCGTCAA | 720 |
| CAAGCTCATT | CAGTTCCTGA | TCTCACTGGT | GCAGTCAAAC | 760 |
| CGGATCCTGG | GGGTGAAGAG | AAAGATCCCC | CTGATGCTGA | 800 |
| ACGACAGTGG | CTCAGCACAT | TCCATGCCCA | AGTATAGCCG | 840 |
| GCAGTTCTCC | CTGGAGCACG | TCCACGGCTC | GGGCCCCTAC | 880 |
| TCGGCCCCCT | CCCCAGCCTA | CAGCAGCTCC | AGCCTCTACG | 920 |
| CCCCTGATGC | TGTGGCCAGC | TCTGGACCCA | TCATCTCCGA | 960 |
| CATCACCGAG | CTGGCTCCTG | CCAGCCCCAT | GGCCTCCCCC | 1000 |
| GGCGGGAGCA | TAGACGAGAG | GCCCCTATCC | AGCAGCCCCC | 1040 |
| TGGTGCGTGT | CAAGGAGGAG | CCCCCCAGCC | CGCCTCAGAG | 1080 |
| CCCCGGGTA | GAGGAGGCGA | GTCCCGGGCG | CCCATCTTCC | 1120 |
| GTGGACACCC | TCTTGTCCCC | GACCGCCCTC | ATTGACTCCA | 1160 |
| TCCTGCGGGA | GAGTGAACCT | GCCCCCGCCT | CCGTCACAGC | 1200 |
| CCTCACGGAC | GCCAGGGGCC | ACACGGACAC | CGAGGGCCGG | 1240 |
| CCTCCCTCCC | CCCCGCCCAC | CTCCACCCCT | GAAAAGTGCC | 1280 |
| TCAGCGTAGC | CTGCCTGGAC | AAGAATGAGC | TCAGTGACCA | 1320 |
| CTTGGATGCT | ATGGACTCCA | ACCTGGATAA | CCTGCAGACC | 1360 |
| ATGCTGAGCA | GCCACGGCTT | CAGCGTGGAC | ACCAGTGCCC | 1400 |
| TGCTGGACCT | GTTCAGCCCC | TCGGTGACCG | TGCCCGACAT | 1440 |
| GAGCCTGCCT | GACCTTGACA | GCAGCCTGGC | CAGTATCCAA | 1480 |
| GAGCTCCTGT | CTCCCCAGGA | GCCCCCCAGG | CCTCCCGAGG | 1520 |
| CAGAGAACAG | CAGCCCGGAT | TCAGGGAAGC | AGCTGGTGCA | 1560 |
| CTACACAGCG | CAGCCGCTGT | TCCTGCTGGA | CCCCGGCTCC | 1600 |
| GTGGACACCG | GGAGCAACGA | CCTGCCGGTG | CTGTTTGAGC | 1640 |
| TGGGAGAGGG | CTCCTACTTC | TCCGAAGGGG | ACGGCTTCGC | 1680 |
| CGAGGACCCC | ACCATCTCCC | TGCTGACAGG | CTCGGAGCCT | 1720 |
| CCCAAAGCCA | AGGACCCCAC | TGTCTCCTAG | AGGCCCCGGA | 1760 |
| GGAGCTGGGC | CAGCCGCCCA | CCCCACCCC | CAGTGCAGGG | 1800 |
| CTGGTCTTGG | GGAGGCAGGG | CAGCCTCGCG | GTCTTGGGCA | 1840 |
| CTGGTGGGTC | GGCCGCCATA | GCCCCAGTAG | GACAAACGGG | 1880 |
| CTCGGGTCTG | GGCAGCACCT | CTGGTCAGGA | GGGTCACCCT | 1920 |
| GGCCTGCCAG | TCTGCCTTCC | CCCAACCCCG | TGTCCTGTGG | 1960 |

| | | | | | | | | | | |
|---|---|---|---|---|---|---|---|---|---|---|
|TTTGGTTGGG|GCTTCACAGC|CACACCTGGA|CTGACCCTGC| | | | | | |2000|
|AGGTTGTTCA|TAGTCAGAAT|TGTATTTTGG|ATTTTTACAC| | | | | | |2040|
|AACTGTCCCG|TTCCCCGCTC|CACAGAGATA|CACAGATATA| | | | | | |2080|
|TACACACAGT|GGATGGACGG|ACAAGACAGG|CAGAGATCTA| | | | | | |2120|
|TAAACAGACA|GGCTCTAAAA|AAAAAAAAAA|AAAAAA| | | | | | |2156|

( 2 ) INFORMATION FOR SEQ ID NO:32:

( i ) SEQUENCE CHARACTERISTICS:
        ( A ) LENGTH: 529
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:32:

```
Met Asp Leu Pro Val Gly Pro Gly Ala Ala Gly Pro
  1               5                  10

Ser Asn Val Pro Ala Phe Leu Thr Lys Leu Trp Thr
             15                  20

Leu Val Ser Asp Pro Asp Thr Asp Ala Leu Ile Cys
 25                  30                      35

Trp Ser Pro Ser Gly Asn Ser Phe His Val Phe Asp
             40                  45

Gln Gly Gln Phe Ala Lys Glu Val Leu Pro Lys Tyr
     50                  55                  60

Phe Lys His Asn Asn Met Ala Ser Phe Val Arg Gln
                 65                  70

Leu Asn Met Tyr Gly Phe Arg Lys Val Val His Ile
             75                  80

Glu Gln Gly Gly Leu Val Lys Pro Glu Arg Asp Asp
 85                  90                      95

Thr Glu Phe Gln His Pro Cys Phe Leu Arg Gly Gln
                100                 105

Glu Gln Leu Leu Glu Asn Ile Lys Arg Lys Val Thr
        110                 115                 120

Ser Val Ser Thr Leu Lys Ser Glu Asp Ile Lys Ile
                125                 130

Arg Gln Asp Ser Val Thr Lys Leu Leu Thr Asp Val
        135                 140

Gln Leu Met Lys Gly Lys Gln Glu Cys Met Asp Ser
145                 150                 155

Lys Leu Leu Ala Met Lys His Glu Asn Glu Ala Leu
             160                 165

Trp Arg Glu Val Ala Ser Leu Arg Gln Lys His Ala
    170                 175                 180

Gln Gln Gln Lys Val Val Asn Lys Leu Ile Gln Phe
                185                 190

Leu Ile Ser Leu Val Gln Ser Asn Arg Ile Leu Gly
            195                 200

Val Lys Arg Lys Ile Pro Leu Met Leu Asn Asp Ser
205                 210                 215

Gly Ser Ala His Ser Met Pro Lys Tyr Ser Arg Gln
             220                 225
```

```
Phe  Ser  Leu  Glu  His  Val  His  Gly  Ser  Gly  Pro  Tyr
     230                      235                      240

Ser  Ala  Pro  Ser  Pro  Ala  Tyr  Ser  Ser  Ser  Ser  Leu
                    245                      250

Tyr  Ala  Pro  Asp  Ala  Val  Ala  Ser  Ser  Gly  Pro  Ile
               255                 260

Ile  Ser  Asp  Ile  Thr  Glu  Leu  Ala  Pro  Ala  Ser  Pro
265                      270                 275

Met  Ala  Ser  Pro  Gly  Gly  Ser  Ile  Asp  Glu  Arg  Pro
               280                      285

Leu  Ser  Ser  Ser  Pro  Leu  Val  Arg  Val  Lys  Glu  Glu
     290                      295                      300

Pro  Pro  Ser  Pro  Pro  Gln  Ser  Pro  Arg  Val  Glu  Glu
                    305                      310

Ala  Ser  Pro  Gly  Arg  Pro  Ser  Ser  Val  Asp  Thr  Leu
               315                 320

Leu  Ser  Pro  Thr  Ala  Leu  Ile  Asp  Ser  Ile  Leu  Arg
325                      330                      335

Glu  Ser  Glu  Pro  Ala  Pro  Ala  Ser  Val  Thr  Ala  Leu
               340                      345

Thr  Asp  Ala  Arg  Gly  His  Thr  Asp  Thr  Glu  Gly  Arg
     350                      355                      360

Pro  Pro  Ser  Pro  Pro  Pro  Thr  Ser  Thr  Pro  Glu  Lys
                    365                      370

Cys  Leu  Ser  Val  Ala  Cys  Leu  Asp  Lys  Asn  Glu  Leu
               375                 380

Ser  Asp  His  Leu  Asp  Ala  Met  Asp  Ser  Asn  Leu  Asp
385                      390                      395

Asn  Leu  Gln  Thr  Met  Leu  Ser  Ser  His  Gly  Phe  Ser
               400                      405

Val  Asp  Thr  Ser  Ala  Leu  Leu  Asp  Leu  Phe  Ser  Pro
     410                      415                      420

Ser  Val  Thr  Val  Pro  Asp  Met  Ser  Leu  Pro  Asp  Leu
                    425                      430

Asp  Ser  Ser  Leu  Ala  Ser  Ile  Gln  Glu  Leu  Leu  Ser
               435                 440

Pro  Gln  Glu  Pro  Pro  Arg  Pro  Pro  Glu  Ala  Glu  Asn
445                      450                      455

Ser  Ser  Pro  Asp  Ser  Gly  Lys  Gln  Leu  Val  His  Tyr
               460                      465

Thr  Ala  Gln  Pro  Leu  Phe  Leu  Leu  Asp  Pro  Gly  Ser
     470                      475                      480

Val  Asp  Thr  Gly  Ser  Asn  Asp  Leu  Pro  Val  Leu  Phe
                    485                      490

Glu  Leu  Gly  Glu  Gly  Ser  Tyr  Phe  Ser  Glu  Gly  Asp
          495                 500

Gly  Phe  Ala  Glu  Asp  Pro  Thr  Ile  Ser  Leu  Leu  Thr
505                      510                      515

Gly  Ser  Glu  Pro  Pro  Lys  Ala  Lys  Asp  Pro  Thr  Val
               520                      525

Ser
```

( 2 ) INFORMATION FOR SEQ ID NO:33:

(i) SEQUENCE CHARACTERISTICS:
    (A) LENGTH: 278
    (B) TYPE: nucleic acid
    (C) STRANDEDNESS: single
    (D) TOPOLOGY: linear (ii) MOLECULE TYPE: (DNA) genomic (xi) SEQUENCE DESCRIPTION: SEQ ID NO:33:

| | | | | |
|---|---|---|---|---|
| CAGGATCTCG | ATCCGCGAA | ATTAATACGA | CTCACTATAG | 40 |
| GGAGACCACA | ACGGTTTCCC | TCTAGAAATA | ATTTTGTTTA | 80 |
| ACTTTAAGGA | GATATACATA | TGAAGCTTGA | ATTCTCGAGG | 120 |
| ATCCCGGGCC | CTAGCTAACT | GATCCGGCTG | CTAACAAAGC | 160 |
| CCGAAAGGAA | GCTGAGTTGG | CTGCTGCCAC | CGCTGAGCAA | 200 |
| TAACTAGCAT | AACCCCTTGG | GGCCTCTAAA | CGGGTCTTGA | 240 |
| GGGGTTTTTT | GCTGAAAGGA | GGAACTATAG | ATATATTC | 278 |

(2) INFORMATION FOR SEQ ID NO:34:

(i) SEQUENCE CHARACTERISTICS:
    (A) LENGTH: 20
    (B) TYPE: nucleic acid
    (C) STRANDEDNESS: single
    (D) TOPOLOGY: linear (ii) MOLECULE TYPE: (DNA) genomic (xi) SEQUENCE DESCRIPTION: SEQ ID NO:34:

CGTAATACGA CTCACTATAG                    20

(2) INFORMATION FOR SEQ ID NO:35:

(i) SEQUENCE CHARACTERISTICS:
    (A) LENGTH: 18
    (B) TYPE: nucleic acid
    (C) STRANDEDNESS: single
    (D) TOPOLOGY: linear (ii) MOLECULE TYPE: (DNA) genomic (xi) SEQUENCE DESCRIPTION: SEQ ID NO:35:

CTCAGCTTCC TTTCGGGC                      18

(2) INFORMATION FOR SEQ ID NO:36:

(i) SEQUENCE CHARACTERISTICS:
    (A) LENGTH: 20
    (B) TYPE: nucleic acid
    (C) STRANDEDNESS: single
    (D) TOPOLOGY: linear (ii) MOLECULE TYPE: (DNA) genomic (xi) SEQUENCE DESCRIPTION: SEQ ID NO:36:

ATATAGTTCC TCCTTTCAGC                    20

(2) INFORMATION FOR SEQ ID NO:37:

(i) SEQUENCE CHARACTERISTICS:
    (A) LENGTH: 110
    (B) TYPE: nucleic acid
    (C) STRANDEDNESS: double
    (D) TOPOLOGY: linear (ii) MOLECULE TYPE: genomic DNA ( x i ) SEQUENCE DESCRIPTION: SEQ ID NO:37:

AAACGGCACA CTGTTCTCGT TGCTTCGAGA GAGCGCGCCT            40

CGAATGTTCG CGAAAAGAGC GCCGGAGTAT AAATAGAGGC            80

GCTTCGTCGA CGGAGCGTCA ATTCAATTCA                       110

( 2 ) INFORMATION FOR SEQ ID NO:38:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: oligonucleotide ( i x ) FEATURE:
        ( D ) OTHER INFORMATION: The first and third N
        can be cort, the second and fourth N can
        be G or C and the fifth N can be G or A ( x i ) SEQUENCE DESCRIPTION: SEQ ID NO:38:

TTNCANGTNG ANTANTANTT                                  20

( 2 ) INFORMATION FOR SEQ ID NO:39:

( i ) SEQUENCE CHARACTERISTICS:
        ( A ) LENGTH: 20
        ( B ) TYPE: nucleic acid
        ( C ) STRANDEDNESS: single
        ( D ) TOPOLOGY: linear ( i i ) MOLECULE TYPE: oligonucleotide ( i x ) FEATURE:
        ( D ) OTHER INFORMATION: The first, second,
        third and fifth N can be C or T and the
        fourth N can be G or A ( x i ) SEQUENCE DESCRIPTION: SEQ ID NO:39:

TACTTNGTNC TNTTNCTNCA                                  20

( 2 ) INFORMATION FOR SEQ ID NO:40:

( i ) SEQUENCE CHARACTERISTICS:
        ( A ) LENGTH: 110
        ( B ) TYPE: nucleic acid
        ( C ) STRANDEDNESS: double
        ( D ) TOPOLOGY: linear ( i i ) MOLECULE TYPE: genomic DNA ( x i ) SEQUENCE DESCRIPTION: SEQ ID NO:40:

TGAATTGAAT TGACGCTCCG TCGACGAAGC GCCTCTATTT            40

ATACTCCGGC GCTCTTTTCG CGAACATTCG AGGCGCGCTC            80

TCTCGAAGCA ACGAGAACAG TGTGCCGTTT                       110

( 2 ) INFORMATION FOR SEQ ID NO:41:

( i ) SEQUENCE CHARACTERISTICS:
        ( A ) LENGTH: 204
        ( B ) TYPE: nucleic acid
        ( C ) STRANDEDNESS: double
        ( D ) TOPOLOGY: linear ( i i ) MOLECULE TYPE: (DNA) genomic ( x i ) SEQUENCE DESCRIPTION: SEQ ID NO:41:

```
TGAATTGAAT  TGACGCTCCG  TCGACGAAGC  GCCTCTATTT                40

ATACTCCGGC  GCTCTTTTCG  CGAACATTCG  AGGCGCGCTC                80

TCTCGAAGCA  ACGAGAACAG  TGTGCCGTTT  ACTGTGCGAC               120

AGAGTGAGAG  AGCAATAGTA  CAGAGAGGGA  GAGTCACAAA               160

ACGAATAGAG  AATAACGGCC  AGAGAAATTT  CTCGAGACCT               200

CGAG                                                          204
```

( 2 ) INFORMATION FOR SEQ ID NO:42:

( i ) SEQUENCE CHARACTERISTICS:
        ( A ) LENGTH: 2781
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:42:

```
AATTGGTCAC  GCTGCGAACA  GAAGCAAATT  TACTTGACGG                40

AGGTTTCATT  AAATTTTCAC  TTGTGAATAA  AACGCGAAAA                80

AGCACTTAAA  AACCGAAGAA  CTGTGTAAAA  CAAAAGCGGT               120

ACGCCAAGAA  AGTGAAGTGT  AATAACTAAA  CTAAACAAGT               160

AAAACGCGAG  TTTTCACTT   CGCGAAAGGT  TTGTGAGCTG               200

CAAAATTGTT  AAGGCTGCTG  GTCACTTTAT  GTCCAGGTCG               240

CGTTCATCCG  CTAAAGCCGT  GCAGTTCAAG  CACGAATCGG               280

AGGAAGAGGA  AGAAGACGAG  GAGGAGCAGC  TGCCTTCCAG               320

GAGAATGCAC  TCTTACGGAG  ACGCCGCGGC  CATCGGAAGC               360

GGGGTGCCGG  CCTTTTTGGC  CAAATTGTGG  CGCCTGGTGG               400

ACGATGCCGA  TACCAATCGC  TTGATTTGCT  GGACCAAGGA               440

TGGCCAAAGT  TTCGTTATTC  AAAATCAAGC  GCAATTTGCC               480

AAGGAACTAT  TGCCACTAAA  CTACAAGCAC  AACAACATGG               520

CCAGTTTCAT  AAGGCAATTG  AATATGTATG  GATTCCACAA               560

GATCACCTCT  ATTGACAATG  GCGGACTACG  TTTTGATCGC               600

GACGAGATTG  AATTTCGCA   CCCATTTTTT  AAGCGCAACT               640

CGCCTTTTCT  ACTTGACCAA  ATCAAAAGGA  AAATATCGAA               680

CAACAAAAAT  GGTGACGACA  AAGGTGTCCT  GAAGCCGGAG               720

GCCATGTCGA  AGATTCTCAC  CGATGTGAAA  GTCATGCGGG               760

GTCGTCAGGA  CAATCTGGAT  TCGCGCTTCT  CCGCCATGAA               800

ACAGGAGAAC  GAAGTGCTGT  GGCGCGAGAT  AGCCAGCCTG               840

CGCCAAAAGC  ACGCTAAGCA  GCAACAAATA  GTCAACAAAC               880

TGATCCAGTT  CCTCATTACC  ATTGTGCAAC  CGTCGCGCAA               920

CATGTCTGGC  GTGAAACGCC  ATGTGCAGCT  GATGATCAAC               960

AATACGCCGG  AAATTGATCG  TGCACGGACC  ACCAGTGAGA              1000

CCGAGAGCGA  GAGTGGCGGC  GGACCGGTTA  TCCACGAGCT              1040

TAGGGAGGAG  CTTCTTGATG  AGGTGATGAA  TCCATCACCG              1080
```

| | | | | |
|---|---|---|---|---|
| GCTGGCTACA | CCGCAGCCTC | ACATTATGAC | CAAGAGAGCG | 1120 |
| TCTCTCCGCC | TGCCGTTGAG | CGTCCGCGAT | CTAACATGAG | 1160 |
| CATTAGCTCG | CACAACGTCG | ATTATTCGAA | TCAGAGTGTG | 1200 |
| GAGGACTTGC | TGCTCCAGGG | AAATGGAACC | GCTGGCGGTA | 1240 |
| ATATTCTAGT | AGGCGGAGCC | GCTTCTCCCA | TGGCCCAAAG | 1280 |
| TGTGAGTCAA | TCGCCGGCCC | AACATGATGT | CTACACAGTC | 1320 |
| ACCGAGGCGC | CCGATTCTCA | TGTCCAGGAG | GTGCCAAACA | 1360 |
| GTCCGCCTTA | TTACGAGGAG | CAGAATGTGC | TTACCACGCC | 1400 |
| CATGGTGCGG | GAGCAGGAGC | AGCAGAAGCG | TCAGCAGCTT | 1440 |
| AAGGAGAACA | ACAAGCTACG | ACGACAGGCA | GGAGATGTTA | 1480 |
| TACTTGATGC | TGGAGATATT | CTCGTAGATA | GTTCGTCGCC | 1520 |
| CAAGGCGCAA | CGGACAAGCA | TCCAGCATAG | TACGCAACCT | 1560 |
| GATGTGATGG | TCCAGCCAAT | GATTATAAAG | TCTGAGCCGG | 1600 |
| AGAACAGTTC | CGGACTGATG | GATCTAATGA | CTCCCGCGAA | 1640 |
| CGATCTGTAC | AGTGTCAACT | TCATCAGTGA | GGATATGCCG | 1680 |
| ACGGATATTT | TTGAAGACGC | TCTGCTTCCC | GACGGCGTGG | 1720 |
| AAGAGGCAGC | CAAACTGGAC | CAGCAGCAAA | AATTTGGGCA | 1760 |
| ATCGACAGTG | AGCAGCGGCA | AGTTTGCCAG | CAACTTCGAT | 1800 |
| GTGCCCACCA | ACAGTACGCT | GCTGGATGCC | AATCAGGCCT | 1840 |
| CGACATCGAA | GGCAGCGGCC | AAGGCGCAAG | CATCTGAGGA | 1880 |
| AGAGGGCATG | GCTGTGGCCA | ATACAGTGG | CGCTGAGAAC | 1920 |
| GGAAACAACC | GCGATACCAA | CAACAGTCAA | CTCCTCAGGA | 1960 |
| TGGCCTCAGT | TGACGAACTC | CACGGGCACT | TGGAAAGCAT | 2000 |
| GCAAGATGAG | TTGGAAACAC | TGAAGGATCT | GCTGCGCGGC | 2040 |
| GATGGGGTGG | CCATTGATCA | GAACATGCTC | ATGGGTCTGT | 2080 |
| TTAACGACTC | TGATCTAATG | GACAACTATG | GCCTATCGTT | 2120 |
| TCCCAATGAC | AGCATAAGCA | GTGAAAAGAA | AGCACCCAGT | 2160 |
| GGCTCTGAAC | TGATTTCCTA | TCAGCCCATG | TATGATCTGT | 2200 |
| CCGACATTTT | GGACACGGAC | GATGGCAACA | ATGACCAGGA | 2240 |
| GGCCAGCAGG | CGCCAGATGC | AGACGCAAAG | TTCGGTTTTA | 2280 |
| AATACGCCAC | GTCACGAGTT | GTAACTTATA | TTAAGTAGCA | 2320 |
| GCAGCTCAGC | CGTTAAATTG | GCGAACAAAT | CGTTTTTAGT | 2360 |
| GTTAAATGCA | AATCTTGACA | CGTTAATTTT | CATCACCTAC | 2400 |
| TCTGTCTAAC | CATTTAGTTG | ATTCATACGA | TAATCACATT | 2440 |
| AATAACCACT | ATAATCATAT | GAATGATCTG | TATATGCCTT | 2480 |
| ATGCACTATA | TATATGATAT | ATAGACTAAC | CAGTTCTTGT | 2520 |
| TGTAGAAAGA | CTCGAAGAAT | CAGTAAAGAT | TTAGATTTAT | 2560 |
| TTTGTATCGC | GGGATTTTGC | GGGCCCCAGC | TCAGCAGGTA | 2600 |
| GAAGATTTTT | AGTTTGCACT | AACCGATCGA | GAGTACAGTG | 2640 |
| AAAGCTGATC | GCATCGTATA | CGATTTAAGA | TCGCACGCTT | 2680 |

| | | | | |
|---|---|---|---|---|
| CAGTTTATAC | ATTTTACACA | CTACTCTTAT | CATTATTTCA | 2720 |
| AAATAAATTG | TTTAATGTCG | CGTTGAGCTG | CAAATGAAAA | 2760 |
| AAAAAAAAAA | AAAAAAAAA | A | | 2781 |

What is claimed is:

1. An isolated polynucleotide encoding a human heat shock factor (HSF), wherein said HSF has a nucleotide sequence selected from the group consisting of (a) the nucleotide sequence as shown in FIG. 13 (SEQ ID NO: 31); (b) an allele of the nucleotide sequence shown in FIG. 13 (SEQ ID NO:31) which encodes a protein which retains the HSF function of the amino acid sequence shown in FIG. 13 (SEQ ID NO: 32); and (c) a fragment of the nucleotide sequence shown in FIG. 13 (SEQ ID NO: 31) which encodes a protein which retains the HSF function of the amino acid sequence shown in FIG. 13 (SEQ ID NO: 32).

2. An isolated polynucleotide according to claim 1, wherein said polynucleotide has the nucleotide sequence as shown in FIG. 13 (SEQ ID NO: 31).

3. An isolated polynucleotide according to claim 1, wherein said polynucleotide is an allele of the nucleotide sequence shown in FIG. 13 (SEQ ID NO: 31) which encodes a protein which retains the HSF function of the amino acid sequence shown in FIG. 13 (SEQ ID NO: 32).

4. An isolated polynucleotide according to claim 1, wherein said polynucleotide is a fragment of the nucleotide sequence shown in FIG. 13 (SEQ ID NO: 31) which encodes a protein which retains the HSF function of the amino acid sequence shown in FIG. 13 (SEQ ID NO: 32).

5. A vector comprising an isolated polynucleotide sequence encoding a human heat shock factor (HSF), wherein said nucleotide sequence is selected from the group consisting of (a) the nucleotide sequence as shown in FIG. 13 (SEQ ID NO: 31); (b) an allele of the nucleotide sequence shown in FIG. 13 (SEQ ID NO: 31) which encodes a protein which retains the HSF function of the amino acid sequence shown in FIG. 13 (SEQ ID NO: 32); and (c) a fragment of the nucleotide sequence shown in FIG. 13 (SEQ ID NO: 31) which encodes a protein which retains the HSF function of the amino acid sequence shown in FIG. 13 (SEQ ID NO: 32).

6. A vector comprising an isolated polynucleotide according to claim 5, wherein said polynucleotide is the nucleotide sequence shown in FIG. 13 (SEQ ID NO: 31).

7. A vector comprising an isolated polynucleotide according to claim 5, wherein said polynucleotide is an allele of the nucleotide sequence shown in FIG. 13 (SEQ ID NO: 31) which encodes a protein which retains the HSF function of the amino acid sequence shown in FIG. 13 (SEQ ID NO: 32).

8. A vector comprising an isolated polynucleotide according to claim 5, wherein said polynucleotide is a fragment of the nucleotide sequence shown in FIG. 13 (SEQ ID NO: 31) encodes a protein which retains the HSF function of the amino acid sequence shown in FIG. 13 (SEQ ID NO:32).

9. A host cell transformed with a vector molecule according to claim 5.

10. A host cell transformed with the vector according to claim 6.

11. A host cell transformed with the vector molecule according to claim 7.

12. A host cell transformed with the vector molecule according to claim 8.

13. The host cell according to claim 10 wherein the host cell is selected from the group consisting of prokaryotic and eukaryotic cells.

14. The host cell according to claim 11 wherein the host cell is selected from the group consisting of prokaryotic and eukaryotic cells.

15. The host cell according to claim 12 wherein the host cell is selected from the group consisting of prokaryotic and eukaryotic cells.

* * * * *